(12) United States Patent
Pollack et al.

(10) Patent No.: US 8,852,952 B2
(45) Date of Patent: Oct. 7, 2014

(54) METHOD OF LOADING A DROPLET ACTUATOR

(75) Inventors: Michael G. Pollack, Durham, NC (US); Prasanna Thwar, Morrisville, NC (US); Vamsee K. Pamula, Durham, NC (US); Allen Eckhardt, Durham, NC (US); Alexander Shenderov, Raleigh, NC (US); Dwayne Allen, Durham, NC (US); Vijay Srinivasan, Durham, NC (US)

(73) Assignee: Advanced Liquid Logic, Inc., Research Triangle Park, NC (US)

( * ) Notice: Subject to any disclaimer, the term of this patent is extended or adjusted under 35 U.S.C. 154(b) by 776 days.

(21) Appl. No.: 12/990,815

(22) PCT Filed: May 4, 2009

(86) PCT No.: PCT/US2009/042731
§ 371 (c)(1),
(2), (4) Date: Jan. 6, 2011

(87) PCT Pub. No.: WO2009/137415
PCT Pub. Date: Nov. 12, 2009

(65) Prior Publication Data
US 2011/0104816 A1 May 5, 2011

Related U.S. Application Data

(60) Provisional application No. 61/050,207, filed on May 3, 2008, provisional application No. 61/052,215, filed on May 11, 2008, provisional application No. 61/052,224, filed on May 11, 2008, provisional application No. 61/075,616, filed on Jun. 25, 2008, provisional application No. 61/085,032, filed on Jul. 31, 2008, provisional application No. 61/088,555, filed on Aug. 13, 2008, provisional application No. 61/093,462, filed on Sep. 2, 2008, provisional application No. 61/157,302, filed on Mar. 4, 2009.

(51) Int. Cl.
*G01N 1/00* (2006.01)

(52) U.S. Cl.
USPC .......................................... 436/180; 436/174

(58) Field of Classification Search
USPC .......... 422/500, 501, 502, 503, 504; 436/174, 436/180; 347/19; 204/403.01, 400, 452; 435/287.2, 287.1, 6.11, 288.7
See application file for complete search history.

(56) References Cited

U.S. PATENT DOCUMENTS

| | | |
|---|---|---|
| 4,636,785 A | 1/1987 | Le Pesant |
| 5,181,016 A | 1/1993 | Lee et al. |

(Continued)

FOREIGN PATENT DOCUMENTS

| | | |
|---|---|---|
| WO | 0069565 A1 | 11/2000 |
| WO | 0073655 A1 | 12/2000 |

(Continued)

OTHER PUBLICATIONS

Hirano, M. et al. "Protein crystallization device using electrostatic micromanipulation." 7th Int. Conf. on Miniturized Chem. and Biochem. Analy. Systems (2003) p. 473-476.*

(Continued)

*Primary Examiner* — Christopher A Hixson
(74) *Attorney, Agent, or Firm* — William A. Barrett; Ward & Smith, P.A.

(57) ABSTRACT

The invention provides droplet actuators and droplet actuator cassettes including reagent storage capabilities, as well as methods of making and using the droplet actuators and cassettes. The invention also provides continuous flow channel elements and techniques for using electrodes to manipulate droplets in flowing streams. The invention also discloses methods of separating compounds on a droplet actuator. Various other aspects of the invention are also disclosed.

22 Claims, 39 Drawing Sheets

(56) References Cited

U.S. PATENT DOCUMENTS

| | | |
|---|---|---|
| 5,486,337 A | 1/1996 | Ohkawa et al. |
| 6,063,339 A | 5/2000 | Tisone et al. |
| 6,130,098 A | 10/2000 | Handique et al. |
| 6,294,063 B1 | 9/2001 | Becker et al. |
| 6,565,727 B1 | 5/2003 | Shenderov |
| 6,773,566 B2 | 8/2004 | Shenderov |
| 6,790,011 B1 | 9/2004 | Le Pesant et al. |
| 6,911,132 B2 | 6/2005 | Pamula et al. |
| 6,924,792 B1 | 8/2005 | Jessop |
| 6,977,033 B2 | 12/2005 | Becker et al. |
| 6,989,234 B2 | 1/2006 | Kolar et al. |
| 7,052,244 B2 | 5/2006 | Fouillet et al. |
| 7,163,612 B2 | 1/2007 | Sterling et al. |
| 7,211,223 B2 | 5/2007 | Fouillet et al. |
| 7,255,780 B2 | 8/2007 | Shenderov |
| 7,328,979 B2 | 2/2008 | Decre et al. |
| 7,329,545 B2 | 2/2008 | Pamula et al. |
| 7,439,014 B2 | 10/2008 | Pamula et al. |
| 7,458,661 B2 | 12/2008 | Kim et al. |
| 7,531,072 B2 | 5/2009 | Roux et al. |
| 7,547,380 B2 | 6/2009 | Velev |
| 7,569,129 B2 | 8/2009 | Pamula et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonnier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 | 1/2012 | Winger et al. |
| 8,093,064 B2 | 1/2012 | Shah et al. |
| 8,137,917 B2 | 3/2012 | Pollack et al. |
| 8,147,668 B2 | 4/2012 | Pollack et al. |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,304,253 B2 | 11/2012 | Yi et al. |
| 8,313,698 B2 | 11/2012 | Pollack et al. |
| 8,317,990 B2 | 11/2012 | Pamula et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0143437 A1 | 10/2002 | Handique et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2004/0031688 A1 | 2/2004 | Shenderov |
| 2004/0055891 A1 | 3/2004 | Pamula et al. |
| 2004/0058450 A1 | 3/2004 | Pamula et al. |
| 2004/0231987 A1 | 11/2004 | Sterling et al. |
| 2006/0021875 A1 | 2/2006 | Griffith et al. |
| 2006/0054503 A1 | 3/2006 | Pamula et al. |
| 2006/0164490 A1 | 7/2006 | Kim et al. |
| 2006/0194331 A1 | 8/2006 | Pamula et al. |
| 2006/0231398 A1 | 10/2006 | Sarrut et al. |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1* | 10/2007 | Pamula et al. ................ 436/518 |
| 2007/0267294 A1 | 11/2007 | Shenderov |
| 2007/0275415 A1 | 11/2007 | Srinivasan et al. |
| 2008/0006535 A1 | 1/2008 | Paik et al. |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0210558 A1 | 9/2008 | Sauter-Starace et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |

(56) References Cited

U.S. PATENT DOCUMENTS

| | | |
|---|---|---|
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0132528 A1 | 5/2012 | Shenderov et al. |
| 2012/0165238 A1 | 6/2012 | Pamula et al. |

FOREIGN PATENT DOCUMENTS

| | | |
|---|---|---|
| WO | 2004029585 A1 | 4/2004 |
| WO | 2004030820 | 4/2004 |
| WO | 2005047696 A1 | 5/2005 |
| WO | 2006013303 A1 | 2/2006 |
| WO | 2006070162 A1 | 7/2006 |
| WO | 2006081558 | 8/2006 |
| WO | 2006124458 A2 | 11/2006 |
| WO | 2006127451 A2 | 11/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007120240 A2 | 10/2007 |
| WO | 2007120241 A2 | 10/2007 |
| WO | 2007123908 A2 | 11/2007 |
| WO | 2008051310 A2 | 5/2008 |
| WO | 2008055256 A3 | 5/2008 |
| WO | 2008068229 A1 | 6/2008 |
| WO | 2008091848 A2 | 7/2008 |
| WO | 2008098236 A2 | 8/2008 |
| WO | 2008101194 A2 | 8/2008 |
| WO | 2008106678 A1 | 9/2008 |
| WO | 2008109664 A1 | 9/2008 |
| WO | 2008112856 A1 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 2008134153 A1 | 11/2008 |
| WO | 2009002920 A1 | 12/2008 |
| WO | 2009003184 A1 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 2009029561 A2 | 3/2009 |
| WO | 2009032863 A2 | 3/2009 |
| WO | 2009052095 A1 | 4/2009 |
| WO | 2009052123 A2 | 4/2009 |
| WO | 2009052321 A2 | 4/2009 |
| WO | 2009052345 | 4/2009 |
| WO | 2009052348 A2 | 4/2009 |
| WO | 2009076414 | 6/2009 |
| WO | 2009086403 A2 | 7/2009 |
| WO | 2009111769 A2 | 9/2009 |
| WO | 2009135205 A2 | 11/2009 |
| WO | 2009137415 A2 | 11/2009 |
| WO | 2009140373 A2 | 11/2009 |
| WO | 2009140671 A2 | 11/2009 |
| WO | 2010006166 A2 | 1/2010 |
| WO | 2010009463 A2 | 1/2010 |
| WO | 2010019782 A2 | 2/2010 |
| WO | 2010027894 A2 | 3/2010 |
| WO | 2010042637 A2 | 4/2010 |
| WO | 2010077859 A3 | 7/2010 |

OTHER PUBLICATIONS

Nisisako, Takasi et al. "Formation of droplets using branch channels in a microfluidic circuit." SICE 2002 p. 1262-1264.*

Wu, Chao-Hsiang et al. "Micro sequential injection: Fermentation monitoring of ammonia, glycerol, glucose, and free iron using the novel lab-on-valve system." Analyst (2001) 126 291-297.*

Ren, H. et al., Automated on-chip droplet dispensing with volume control by electro-wetting actuation and capacitance metering., Sensors and Actuators B., 2004, vol. 98, pp. 319-327.

Srinivasan, et al., "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems , 1(3), Oct. 2005, 186-223.

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

Cotten et al., "Digital Microfluidics: a novel platform for multiplexed detection of lysosomal storage diseases", Abstract # 3747.9. Pediatric Academic Society Conference, 2008.

Delattre, Movie in news on TF1 (at 12'45"Cyril Delattre), http://videos.tf1.fr/jt-we/zoom-sur-grenoble-6071525.html, 2009.

Delattre, Movie in talk show "C Dans l'air" (at 24"Cyril Delattre), http://www.france5.fr/c-dans-l-air/sante/bientot-vous-ne-serez-plus-malade-31721, 2009.

Delattre, Movie on Web TV—Cite des sciences (at 3'26"Cyril Delattre), http://www.universcience.tv/video-laboratoire-de-poche-793.html, 2009.

Delattre et al., "Towards an industrial fabrication process for electrowetting chip using standard MEMS Technology", µTAS2008, San Diego; poster presented, Oct. 15, 2008.

Delattre et al., "Towards an industrial fabrication process for electrowetting chip using standard MEMS Technology", µTAS2008, San Diego; Abstract in proceedings, Oct. 13-16, 2008, 1696-1698.

Dewey, "Towards a Visual Modeling Approach to Designing Microelectromechanical System Transducers", Journal of Micromechanics and Microengineering, vol. 9, Dec. 1999, 332-340.

(56) References Cited

OTHER PUBLICATIONS

Dewey et al., "Visual modeling and design of microelectromechanical system tansducers", Microelectronics Journal, vol. 32, Apr. 2001, 373-381.

Fair et al., "A Micro-Watt Metal-Insulator-Solution-Transport (MIST) Device for Scalable Digital Bio-Microfluidic Systems", IEEE IEDM Technical Digest, 2001, 16.4.1-4.

Fair et al., "Advances in droplet-based bio lab-on-a-chip", BioChips 2003, Boston, 2003.

Fair et al., "Bead-Based and Solution-Based Assays Performed on a Digital Microfluidic Platform", Biomedical Engineering Society (BMES) Fall Meeting, Baltimore, MD, Oct. 1, 2005.

Fair, "Biomedical Applications of Electrowetting Systems", 5th International Electrowetting Workshop, Rochester, NY, May 31, 2006.

Fair et al., "Chemical and Biological Applications of Digital-Microfluidic Devices", IEEE Design & Test of Computers, vol. 24(1), Jan.-Feb. 2007, 10-24.

Fair et al., "Chemical and biological pathogen detection in a digital microfluidic platform", DARPA Workshop on Microfluidic Analyzers for DoD and National Security Applications, Keystone, CO, 2006.

Fair, "Digital microfluidics: is a true lab-on-a-chip possible?", Microfluid Nanofluid, vol. 3, Mar. 8, 2007, 245-281.

Fair, "Droplet-based microfluidic Genome sequencing", NHGRI PI's meeting, Boston, 2005.

Fair et al., "Electrowetting-based On-Chip Sample Processing for Integrated Microfluidics", IEEE Inter. Electron Devices Meeting (IEDM), 2003, 32.5.1-32.5.4.

Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.

Fair, "Scaling of Digital Microfluidic Devices for Picoliter Applications", The 6th International Electrowetting Meeting, Aug. 20-22, 2008, p. 14.

Fouillet, "Bio-Protocol Integration in Digital Microfluidic Chips", The 6th International Electrowetting Meeting, Aug. 20-22, 2008, p. 15.

Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Fouillet et al., "Digital microfluidic design and optimization of classic and new fluidic functions for lab on a chip systems", Microfluid Nanofluid, vol. 4, 2008, 159-165.

Hua et al., "Rapid Detection of Methicillin-Resistant *Staphylococcus aureus* (MRSA) Using Digital Microfluidics", 12th Intl Conference on Miniaturized Systems for Chemistry and Life Sciences, Proc. µTAS, Oct. 12-16, 2008.

Jun et al., "Valveless Pumping using Traversing Vapor Bubbles in Microchannels", J. Applied Physics, vol. 83, No. 11, Jun. 1998, pp. 5658-5664.

Kim et al., "MEMS Devices Based on the Use of Surface Tension", Proc. Int. Semiconductor Device Research Symposium (ISDRS'99), Charlottesville, VA, Dec. 1999, pp. 481-484.

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim et al., "Micromachines Driven by Surface Tension", AIAA 99-3800, 30th AIAA Fluid Dynamics Conference, Norfolk, VA, (Invited lecture), Jun. 1999, pp. 1-6.

Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.

Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.

Lee et al., "Liquid Micromotor Driven by Continuous Electrowetting", Proc. IEEE Micro Electro Mechanical Systems Workshop, Heidelberg, Germany, Jan. 1998, pp. 538-543.

Lee et al., "Theory and Modeling of Continuous Electrowetting Microactuation", Proc. MEMS (MEMS-vol. 1), ASME Int. Mechanical Engineering Congress and Exposition, Nashville, TN, Nov. 1999, pp. 397-403.

Marchand et al., "Organic Synthesis in Soft Wall-Free Microreactors: Real-Time Monitoring of Fluorogenic Reactions", Analytical Chemistry, vol. 80, Jul. 2, 2008, 6051-6055.

Millington et al., "Digital Microfluidics: a novel platform for multiplexed detection of LSDs with potential for newborn screening", Association of Public Health Laboratories Annual Conference, San Antonio, TX, Nov 4, 2008,.

Millington et al., "Digital Microfluidics: A Novel Platform for Multiplexing Assays Used in Newborn Screening", Proceedings of the 7th International and Latin American Congress. Oral Presentations. Rev Invest Clin; vol. 61 (Supl. 1), 2009, 21-33.

Paik et al., "A digital-microfluidic approach to chip cooling", IEEE Design & Test of Computers, vol. 25, Jul. 2008, 372-381.

Paik et al., "Adaptive Cooling of Integrated Circuits Using Digital Microfluidics", IEEE Transactions on VLSI, vol. 16, No. 4, 2008, 432-443.

Paik et al., "Adaptive Cooling of Integrated Circuits Using Digital Microfluidics", accepted for publication in IEEE Transactions on VLSI Systems, 2007, and Artech House, Norwood, MA, 2007.

Paik, "Adaptive Hot-Spot Cooling of Integrated Circuits Using Digital Microfluidics", Dissertation, Dept. of Electrical and Computer Engineering, Duke University, Apr. 25, 2006, 1-188.

Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; POSTER, 2005.

Paik et al., "Coplanar Digital Microfluidics Using Standard Printed Circuit Board Processes", 9th Intl Conf. on Miniaturized Systems for Chemistry and Life Sciences, Boston, MA, Oct. 9-13, 2005, 566-68.

Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.

Paik et al., "Electrowetting-based droplet mixers for microfluidic systems", Lab on a Chip (LOC), vol. 3. (more mixing videos available, along with the article, at LOC's website), 2003, 28-33.

Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.

Paik et al., "Programmable flow-through real-time PCR using digital microfluidics", Proc. Micro Total Analysis Systems (µTAS), Handout, 2007.

Paik et al., "Programmable flow-through real-time PCR using digital microfluidics", Proc. Micro Total Analysis Systems (µTAS), Poster, 2007.

Paik et al., "Rapid Droplet Mixers for Digital Microfluidic Systems", Masters Thesis, Duke Graduate School., 2002, 1-82.

Paik et al., "Rapid droplet mixers for digital microfluidic systems", Lab on a Chip, vol. 3. (More mixing videos available, along with the article, at LOC's website.), 2003, 253-259.

Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.

(56) References Cited

OTHER PUBLICATIONS

Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pamula et al. (CO-CHAIR, "Digital Microfluidics for Lab-on-a-Chip Applications", "Emerging CAD Challenges for Biochip Design" Workshop, Conference on Design, Automation, and Test in Europe (DATE), Munich, Germany, Advance Programme, 2006, pp. 85-87.
Pollack, et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Pollack, "Lab-on-a-chip platform based digital microfluidics", The 6th International Electrowetting Meeting, Aug. 20-22, 2008, 16.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Rival et al., "Towards Single Cells Gene Expression on EWOD Lab on Chip", ESONN 2008, Grenoble, France; Poster presented, Aug. 26, 2008.
Rival et al., "Towards single cells gene expression on EWOD lab on chip", ESONN, Grenoble, France, abstract in proceedings, Aug. 2008.
Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Sista et al., "96-Immunoassay Digital Microfluidic Multiwell Plate", Proc. μTAS, Oct. 12-16, 2008.

Sista, "Development of a Digital Microfluidic Lab-on-a-Chip for Automated Immunoassays with Magnetically Responsive Beads", PhD Thesis, Department of Chemical Engineering, Florida State University, 2007.
Sista et al., "Development of a digital microfluidic platform for point of care testing", Lab on a chip, vol. 8, Dec. 2008, First published as an Advance Article on the web, Nov. 5, 2008, 2091-2104.
Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.
Sista et al., "Spatial multiplexing of immunoassays for small-volume samples", 10th PI Meeting IMAT, Bethesda, 2009.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Digital Microfluidic Lab-on-a-Chip for Protein Crystallization", The 82nd ACS Colloid and Surface Science Symposium, 2008.
Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.
Srinivasan et al., "Droplet-based microfluidic lab-on-a-chip for glucose detection", Analytica Chimica Acta, vol. 507, No. 1, 2004, 145-150.
Srinivasan et al., "Low cost digital microfluidic platform for protein crystallization", Enabling Technologies for Structural Biology, NIGMS Workshop, Bethesda, MD., Mar. 4-6, 2009, J-23.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 72-75.
Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published online, May 2004, 3229-3235.
Thwar et al., "DNA sequencing using digital microfluidics", Poster 42, 41st AACC's Annual Oak Ridge Conference Abstracts, Clinical Chemistry vol. 55, 2009, 1891.
Wang et al., "Droplet-based micro oscillating-flow PCR chip", J. Micromechanics and Microengineering, vol. 15, 2005, 1369-1377.
Wang et al., "Efficient in-droplet separation of magnetic particles for digital microfluidics", Journal of Micromechanics and Microengineering, vol. 17, 2007, 2148-2156.
Xu et al., "A Cross-Referencing-Based Droplet Manipulation Method for High-Throughput and Pin-Constrained Digital Microfluidic Arrays", Proceedings of conference on Design, Automation and Test in Europe (DATE), Apr. 2007.
Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.

(56) References Cited

OTHER PUBLICATIONS

Xu et al., "Automated solution preparation on a digital microfluidic lab-on-chip", PSI Bottlenecks Workshop, 2008.

Xu et al., "Automated, Accurate and Inexpensive Solution-Preparation on a Digital Microfluidic Biochip", Proc. IEEE Biomedical Circuits and Systems Conference (BioCAS), 2008, 301-304.

Xu et al., "Defect-Aware Synthesis of Droplet-Based Microfluidic Biochips", IEEE, 20th International Conference on VLSI Design, 2007.

Xu et al., "Design and Optimization of a Digital Microfluidic Biochip for Protein Crystallization", Proc. IEEE/ACM International Conference on Computer-Aided Design (ICCAD), Nov. 2008, 297-301.

Xu et al., "Digital Microfluidic Biochip Design for Protein Crystallization", IEEE-NIH Life Science Systems and Applications Workshop, LISA, Bethesda, MD, Nov. 8-9, 2007, 140-143.

Xu et al., "Droplet-Trace-Based Array Partitioning and a Pin Assignment Algorithm for the Automated Design of Digital Microfluidic Biochips", CODES, 2006, 112-117.

Xu et al., "Integrated Droplet Routing in the Synthesis of Microfluidic Biochips", IEEE, 2007, 948-953.

Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.

Yao et al., "Spot Cooling Using Thermoelectric Microcooler", Proc. 18th Int. Thermoelectric Conf, Baltimore, VA, pp. 256-259, Aug. 1999.

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi et al., "Characterization of electrowetting actuation on addressable single-side coplanar electrodes", Journal of Micromechanics and Microengineering, vol. 16., Oct. 2006, 2053-2059.

Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "Droplet Manipulation and Microparticle Sampling on Perforated Microfilter Membranes", J. Micromech. Microeng., vol. 18, 2008, 1-11.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

Zhao et al., "Microparticle Concentration and Separation by Traveling-Wave Dielectrophoresis (twDEP) for Digital Microfluidics", J. Microelectromechanical Systems, vol. 16, No. 6, Dec. 2007, 1472-1481.

\* cited by examiner

Dispensing from Preloaded Capillary - Step 1

METHOD OF LOADING A DROPLET ACTUATOR

GOVERNMENT SUPPORT

This invention was made with government support under grant number AI066590-02 awarded by the National Institutes of Health. The United States Government has certain rights in the invention.

RELATED APPLICATIONS

This application claims priority to the following U.S. Patent Applications 61/050,207, entitled "Sample collection devices with sample processing and data storage capability," filed on May 3, 2008; 61/052,215, entitled "Processing Non-liquid Samples on a Droplet Actuator," filed on May 11, 2008; 61/052,224, entitled "Reagent Storage for Field-based Detection," filed on May 11, 2008; 61/075,616, entitled "Rapid Detection of Methicillin Resistant *Staphylococcus aureus* (MRSA) Using Digital Microfluidics," filed on Jun. 25, 2008; 61/085,032, entitled "Rapid Pathogen Detection on a Droplet Actuator," filed on Jul. 31, 2008; 61/088,555, entitled "Fluidic Systems for and Methods of Loading a Droplet actuator," filed on Aug. 13, 2008; 61/093,462, entitled Nucleic Acid Sample Preparation and Analysis on a Droplet Actuator," filed on Sep. 2, 2008; and 61/157,302, entitled "Droplet Actuator Techniques Using Non-liquid Fluids," filed on Mar. 4, 2009.

The foregoing statement applies only to those aspects of the invention described and claimed in this application arising out of U.S. Patent Application Nos. 61/075,616, entitled "Rapid Detection of Methicillin Resistant *Staphylococcus aureus* (MRSA) Using Digital Microfluidics," filed on Jun. 25, 2008; 61/085,032, entitled "Rapid Pathogen Detection on a Droplet Actuator," filed on Jul. 31, 2008; and 61/093,462, entitled "Nucleic Acid Sample Preparation and Analysis on a Droplet Actuator filed on Sep. 2, 2008.

BACKGROUND

Droplet actuators are used to conduct a wide variety of droplet operations. A droplet actuator typically includes two substrates separated to form a droplet operations gap. The substrates include electrodes for conducting droplet operations. The gap between the substrates is typically filled with a filler fluid that is immiscible with the liquid that is to be subjected to droplet operations. Droplet operations are controlled by electrodes associated with one or both of the substrates. There is a need for droplet actuator devices, techniques and systems for making and using droplet actuators. There is a need for devices, techniques and systems for preparing samples and/or reagents for loading onto a droplet actuator; for loading samples and/or reagents onto a droplet actuator; for storing samples and/or reagents on a droplet actuator and/or for use on a droplet actuator; and/or for conducting droplet operations using samples and/or reagents on a droplet actuator. There is a need for devices, techniques and systems for conducting flow through bead handling and washing. For example, there is a need for techniques for splitting droplets in a flow-through system, compartmentalizing beads in droplets in a flow-through system, and washing droplets in a flow-through system. There is a need for droplet actuator devices, techniques and systems for making and using droplet actuators to process viscous, solid or semi-solid samples. For example, there is a need for a techniques for processing process viscous, semisolid, and/or solid samples. There is a need for droplet actuator devices including a gel for use in gel electrophoresis, along with techniques and systems for conducting gel electrophoresis on a droplet actuator. There is a need for a fluidics system and technique for using the system for loading liquids onto a droplet actuator. There is a need for droplet actuators loaded using the fluidics system and method of the invention and methods of using such droplet actuators to conduct droplet operations. There is a need for droplet actuator devices, techniques and systems for processing samples for use on a droplet actuator device. There is a need for droplet actuator devices, techniques and systems for capturing, concentrating and/or eluting nucleic acids; and sensitively isolating nucleic acids using one or more droplet operations to perform separation protocols. There is a need for kits including droplet actuators of the invention along with various other components suitable for executing the techniques of the invention, such as reagents, sample collection devices, and/or instructions.

SUMMARY OF THE INVENTION

The invention provides a droplet actuator, and methods of making and using the droplet actuator. The droplet actuator may include two substrates separated to provide a droplet operations gap. One or more electrodes may be associated with one or both substrates and arranged for conducting one or more droplet operations in the droplet operations gap. The droplet actuator may include a reagent storage cassette with one or more reservoirs including one or more liquids. One or more fluid paths may be provided from the one or more reservoirs into the droplet operations gap. The fluid paths may be blocked by a film or other breakable, removable or puncturable material. A plunger may be associated with the reservoir and arranged to force liquid from the reservoir into the fluid path when depressed into the reservoir. A series of the reservoirs and a series of the plungers may be included. Each of the reservoirs may be associated with a corresponding plunger arranged to force liquid from the reservoir into the fluid path. The plungers may be coupled to a common plunger depressor. The film may be selected with physical and/or chemical characteristics which permit it to break upon application of pressure to liquid in the reservoir or reservoirs when the plunger or plungers are depressed. For example, film may be scored or include a thin or weakened region that breaks upon application of pressure to liquid in the reservoir or reservoirs by depressing the plunger or plungers. The reagent storage cassette may include an awl, scribe or other puncturing device arranged to puncture the film and thereby permit liquid to flow through the fluid path. The device may include an awl, point, scribe or other puncturing device slideably inserted within a slot in the plunger and arranged to puncture the film and thereby permit liquid to flow through the fluid path. The droplet actuator may include a series of reservoirs, wherein each reservoir in the series of the reservoirs may be associated with a connecting fluid path extending from the reservoir and into a channel of the fluid path, such that upon depression of the plungers, a series of droplets may be forced through the connecting fluid path and into the channel. The channel may include a liquid filler fluid which may be immiscible with the series of droplets. The channel may be coupled to a pressure or vacuum source for flowing droplets through the channel and into the droplet operations gap. The channel may be associated with one or more electrodes configured for transporting droplets through the channel and into the droplet operations gap. The droplet actuator may include a series of reservoirs, wherein each reservoir in the series of reservoirs is associated with a fluid path from the reservoir into the droplet operations gap. Liquid forced through the fluid path into the droplet operations gap may be subject to one or more droplet operations in the droplet operations gap. In some embodiments, the fluid path from the reservoir into the droplet operations gap passes through an opening in an electrode. The electrode may, for example, be a droplet operations electrode, such as a reservoir electrode. In some embodiments, the fluid path may be fluidly coupled with one or more filler fluid channels arranged for flowing filler fluid around droplets in the fluid path.

The invention provides a method of conducting a droplet operation including providing a channel; flowing an immiscible liquid including a droplet through the channel and into proximity with a set of one or more electrodes; using the set of one or more electrodes with the droplet to conduct a droplet operation; and continuing to flow the droplet or one or more daughter droplets formed during the droplet operation through the channel. The droplet operation may be effected without stopping flow of the immiscible liquid through the channel. The droplet operation may include splitting the droplet into two or more daughter droplets. The droplet operation may include interrupting the flow of the droplet through the channel. In some embodiments, the channel splits into first and second branches, and the droplet operation may include splitting the droplet into two or more droplets, one or more droplets flowing into a first of the two or more branches and a second of the two or more droplets flowing into a second of the two or more branches. In some embodiments, the channel splits into first and second branches, and the droplet operation causes the droplet to flow down one or the other of the first and second branches.

The invention also provides a method of manipulating a droplet, the method comprising providing a channel; flowing a liquid filler fluid including a magnetically-responsive, bead-containing droplet through the channel and into proximity with a magnetic field to substantially immobilize the magnetically responsive bead and thereby capture the bead-containing droplet; releasing the magnetically responsive bead from the magnetic field, thereby permitting it to continue to flow through the channel. In some cases, substantially all of the liquid volume of the bead-containing droplet remains with the magnetically responsive bead when it may be substantially immobilized by the magnetic field. In other cases, at least a portion of the liquid volume of the bead-containing droplet breaks away from the magnetically responsive bead when it may be substantially immobilized by the magnetic field and continues to flow with the liquid filler fluid through the channel. The method may also include flowing a second droplet in the flowing filler fluid into contact with the captured bead-containing droplet, wherein the second droplet merges with the bead-containing droplet. In some embodiments the flowing filler fluid causes a bead-free droplet to break away from the bead-containing droplet and continue to flow with the liquid filler fluid through the channel. The second droplet may, for example, include a wash buffer. The method may also include repeating the flowing of a second droplet in the flowing filler fluid into contact with the captured bead-containing droplet using a series of two or more of such second droplets to reduce the concentration and/or quantity of a substance present in the liquid volume of the bead-containing droplet. The method may also include repeating the flowing of a second droplet in the flowing filler fluid into contact with the captured bead-containing droplet until the liquid volume of the bead-containing droplet may be substantially replaced. The second droplet may include a sample droplet having a target for which the bead may have affinity. The method may also include repeating the flowing of a second droplet in the flowing filler fluid into contact with the captured bead-containing droplet using a series of two or more of such second droplets to concentrate a target substance on the bead of the bead-containing droplet. The target substance may, for example, include organic molecules, inorganic molecules, peptides, proteins, macromolecules, subcellular components of a biological cell, cells, group of cells, single celled organisms, multicellular organisms. The method may also include flowing a third droplet in the flowing filler fluid into contact with the captured bead-containing droplet, wherein the third droplet merges with the bead-containing droplet; the flowing filler fluid causes a bead-free droplet to break away from the bead-containing droplet and continue to flow with the liquid filler fluid through the channel. The third droplet may, for example, include a wash buffer. The method may also include repeating the flowing of a third droplet in the flowing filler fluid into contact with the captured bead-containing droplet using a series of two or more of such third droplets sufficient to reduce the concentration and/or quantity of a substance present in the liquid volume of the bead-containing droplet. The method may also include repeating the flowing of a third droplet in the flowing filler fluid into contact with the captured bead-containing droplet until the liquid volume of the bead-containing droplet may be substantially replaced. The method may also include releasing the magnetically responsive bead from the magnetic field, e.g., to permit a reconstituted magnetically responsive bead containing droplet to flow in the filler fluid through the channel. In some embodiments the magnetic field may be in proximity with a set of one or more electrodes and the method may include using the set of one or more electrodes with the bead-containing droplet to conduct a droplet operation. The method may include continuing to flow the droplet or one or more daughter droplets formed during the droplet operation through the channel. The method may include flowing the reconstituted magnetically responsive bead containing droplet into a droplet actuator reservoir and/or into a droplet operations gap of a droplet actuator, where the magnetically responsive bead containing droplet may be subjected to one or more droplet operations. The one or more droplet operations may include steps in an assay protocol to analyze a target substance on the magnetically responsive bead. The droplet operation may be effected without stopping flow of the immiscible liquid through the channel. The droplet operation may include splitting the droplet into two or more daughter droplets: one or more of such daughter droplets including the magnetically responsive bead; and one or more of such daughter droplets substantially lacking in magnetically responsive beads. The droplet operation may include interrupting the flow of the droplet through the channel. In some cases, the channel splits into first and second branches; and the droplet operation includes splitting the droplet into two or more droplets, including one or more daughter droplets flowing into a first of the two or more branches and including the magnetically responsive bead; and one or more daughter droplets flowing into a second of the two or more branches and substantially lacking in magnetically responsive beads.

The invention also provides a method of encapsulating a magnetically responsive bead in a droplet, the method may include providing a channel; flowing an immiscible liquid including a magnetically responsive bead through the channel and into proximity with a magnetic field; capturing the magnetically responsive bead in the magnetic field; flowing an immiscible liquid including a droplet into contact with the magnetically responsive bead to encapsulate the magnetically responsive bead in the droplet, thereby yielding a bead-containing droplet. The magnetically responsive bead may have affinity for an aqueous medium, the droplet may include an aqueous medium, and the filler fluid may include a non-aqueous liquid. The method may also include releasing the magnetically responsive bead from the magnetic field, thereby permitting the bead-containing droplet to continue to flow with the filler fluid through the channel.

The invention provides a method of sampling a non-liquid sample on a droplet actuator, the method may include providing a droplet actuator including a droplet operations and electrodes configured to conduct one or more droplet operations on the droplet operations surface; supplying a non-liquid sample in proximity to or in contact with the droplet operations surface; effecting one or more droplet operations to contact a droplet on the droplet operations surface into contact with the non-liquid sample to dissolve into the droplet one or more components of the non-liquid sample; effecting one or more droplet operations to conduct the droplet away from the non-liquid sample. The non-liquid sample may include a solid sample, a semi-solid sample and/or a viscous sample. The droplet may include one or more beads having affinity for one or more of the components of the non-liquid sample. The droplet may include an enzyme having affinity for a component of the non-liquid sample. The droplet may have pH selected to dissolve the non-liquid sample. The sample may include cells and the droplet may include a lysis buffer solution selected to lyse the cells. The one or more droplet operations may include an electrode-mediated droplet operation. The one or more droplet operations may include an electrowetting-mediated droplet operation. The one or more droplet operations may include a dielectrophoresis-mediated droplet operation. The non-liquid sample sufficiently viscous, semi-solid or solid to permit a droplet to contact the sample and be transported away from the sample without being substantially combined with the sample. The non-liquid sample may be selected from the group consisting of sputum, coagulated blood, animal tissue samples, plant tissue samples, soil samples, and rock samples. The non-liquid sample may include a matrix used to collect the sample. The droplet may include an aqueous droplet. The droplet may include a non-aqueous droplet. The method may include using the droplet to conduct an assay analyzing a component of the sample. In some cases, the assay analyzes a protein or peptide present in the sample. In some cases, the assay may include amplifying a nucleic acid present in the sample. The method may include removing the droplet from the droplet actuator.

The invention provides a method of providing a polymerized material on a droplet operations surface. The method may include providing a droplet actuator including a substrate including electrodes arranged for conducting droplet operations on a droplet operations surface of the substrate. The method may include providing on the droplet operations substrate a polymerizable droplet on the droplet operations substrate and a catalyst droplet including a catalyst selected to accelerate polymerization of the polymerizable droplet. The method may also include conducting droplet operations mediated by the electrodes to combine the polymerizable droplet with the catalyst droplet to yield a polymerizing droplet. Further, the method may include permitting the polymerizing droplet to polymerize, thereby yielding a polymerized material on the droplet operations surface. The droplet actuator may include a second substrate separated from the droplet operations surface to provide a droplet operations gap in which the droplet operations may be conducted. In some embodiments the droplet operations may be conducted in a liquid filler fluid which may be immiscible with the polymerizable droplet and the catalyst droplet. In some embodiments the polymerized material may include a gel selected for conducting gel electrophoresis. The polymerized material may, for example, be a polyacrylamide gel or an agarose gel. The method may include activating a series of two or more electrodes underlying the polymerizable droplet to elongate the droplet prior to combining the polymerizable droplet with the catalyst droplet. The method may include activating a series of two or more electrodes underlying the polymerizing droplet to elongate the droplet prior to permitting the polymerizing droplet to polymerize.

The invention also provides a method of causing separation of one or more substances. The method may include providing a sample droplet including substances for separation on the droplet operations surface or in a reservoir associated with a fluid path arranged to flow liquid from the reservoir into contact with the polymerized material. The method may include contacting the sample droplet with the polymerized material. The method may include applying current to the polymerized material to cause separation of one or more of the substances provided in the sample droplet. In some cases, the droplet actuator may include a second substrate separated from the droplet operations surface to provide a droplet operations gap, the second substrate including an opening providing a fluid path from an exterior locus into the droplet operations gap; and providing a sample droplet may include supplying a sample droplet through the opening in the second substrate into contact with the polymerized material. The method may include marking one or more target substances for detection. For example, in some cases, the one or more substances for separation may include one or more nucleic acids, and the marking may include staining the one or more nucleic acids. In some embodiments the marking may include providing a marker droplet on the droplet operations surface, and using one or more droplet operations to transport the marker droplet into contact with the polymerized material.

The invention also provides a droplet actuator including a substrate including electrodes arranged for conducting droplet operations on a droplet operations surface of the substrate; a polymerized material for conducting gel electrophoresis; negative and positive electrodes in contact with the polymerized material. The droplet actuator may include a second substrate separated from the droplet operations surface to provide a droplet operations gap in which the droplet operations may be conducted. The droplet actuator may include a liquid filler fluid in contact with the droplet operations surface. The polymerized material may, for example, include a gel selected from the group consisting of polyacrylamide gels and agarose gels. The droplet actuator may include a sample droplet including substances for separation on the droplet operations surface or in a reservoir associated with a fluid path arranged to flow liquid from the reservoir into contact with the polymerized material. The substances for separation may, for example, include proteins, peptides and/or nucleic acids. The droplet actuator may include a second substrate separated from the droplet operations surface to provide a droplet operations gap. In some cases, the second substrate including an opening providing a fluid path from an exterior locus into the droplet operations gap. The droplet actuator may include including a marker droplet including reagents for marking one or more target substances in the polymerized material for detection.

The invention provides a droplet actuator loading circuit including a primary fluid circuit arranged to flow fluid through a fluid path including a droplet operations gap of a droplet actuator and a an external fluid circuit. The droplet actuator loading circuit may include a reagent fluid path branching from the primary fluid circuit and fluidly connecting the primary fluid path to one or more reservoirs including reagents and/or filler fluid. The droplet actuator loading circuit may include a mechanism for switching the reagent fluid path from one reservoir to another reservoir. The mechanism for switching the reagent fluid path between reagent reservoirs may include a robotic device for moving a terminus of the reagent fluid path from one reservoir to another reservoir. The droplet actuator loading circuit may include one or more valves configured in the primary fluid circuit and/or the reagent fluid path to permit switching between circulating liquid in the primary fluid circuit, and flowing liquid from the one or more reservoirs including reagents and/or filler fluid into the primary fluid circuit. The droplet actuator loading circuit may include a reagent fluid path branching from the primary fluid circuit and fluidly connecting the primary fluid path to one or more reservoirs including reagents, and a filler fluid path branching from the primary fluid circuit and fluidly connecting the primary fluid path to one or more reservoirs including a liquid filler fluid. The droplet actuator loading circuit may include one or more valves configured in the primary fluid circuit and/or the reagent fluid path to permit switching between circulating liquid in the primary fluid circuit, and flowing liquid reagent from the one or more reservoirs including reagents into the primary fluid circuit, flowing filler fluid from the one or more reservoirs including liquid filler fluid into the primary fluid circuit. The droplet actuator loading circuit, wherein the reagent fluid path and/or the filler fluid path branches from the primary fluid circuit at a locus which may be in the external fluid circuit. The droplet actuator loading circuit including a pump disposed to pump liquid through the primary fluid circuit. The pump may, for example, include a reversible pump. The pump may include a peristaltic pump. The pump may be disposed to pump liquid through the primary fluid circuit, wherein the pump may be disposed in the primary fluid circuit at a locus which lies between a locus in the primary fluid circuit at which the reagent fluid path branches from the primary fluid circuit, and a locus in the primary fluid circuit at which the filler fluid path branches from the primary fluid circuit. The droplet actuator loading circuit may also include an overflow fluid path fluidly coupled into the droplet operations gap. The droplet actuator loading circuit may also include a reservoir and a pump disposed to pump liquid from the droplet operations gap through the overflow fluid path and into a reservoir. The reservoir and pump together may comprise a syringe pump.

The invention provides a method of loading a droplet actuator. The method may include providing a droplet actuator loading circuit including a primary fluid circuit arranged to flow fluid through a fluid path including a droplet operations gap of a droplet actuator and a an external fluid circuit. The method may include filling the loading circuit, including the droplet operations gap, with a liquid filler fluid and thereby purging the loading circuit of air. The method may include flowing reagent liquid into the external fluid circuit to form droplets in the liquid filler fluid contained therein. The method may include flowing contents of the external fluid circuit into the droplet operations gap of the droplet actuator. Filling the loading circuit, including the droplet operations gap, with a liquid filler fluid may include flowing filler fluid into the primary fluid circuit via a filler fluid branch in the primary fluid circuit. The filler fluid branch in the primary fluid circuit may be situated in the external fluid circuit. Flowing reagent liquid into the external fluid circuit may include flowing reagent into the primary fluid circuit via a reagent branch in the primary fluid circuit. The reagent branch in the primary fluid circuit may be situated in the external fluid circuit. Different kinds of reagent droplets may be loaded into the external fluid circuit. Reagent types may be selected by switching the reagent branch from one reservoir to another reservoir. The switching may be effected by a robotic device configured to move a terminus of the reagent fluid path from one reservoir to another reservoir. Valves configured in the primary fluid circuit and/or the reagent fluid path to switch between circulating liquid in the primary fluid circuit, and flowing liquid from the one or more reservoirs including reagents and/or filler fluid into the primary fluid circuit. The method further may include flowing liquid from the droplet operations gap through an overflow fluid path fluidly coupled into the droplet operations gap. Flowing liquid from the droplet operations gap through an overflow fluid path may include pumping the liquid through the overflow path into a reservoir. The reservoir and pump together may include a syringe pump.

The invention provides a method of preparing a sample droplet. The method may include providing a droplet actuator substrate including a droplet operations surface and electrodes configured to conduct droplet operations on the droplet operations surface. The method may include providing a sample droplet including cells including a target substance on the droplet operations surface. The method may include providing a lysis droplet including a lysis buffer on the droplet operations surface. The method may include using one or more droplet operations mediated by the electrodes to combine the lysis droplet with the sample droplet to yield a lysed droplet including lysed cells. The method may include providing in the lysed droplet beads having affinity for the target substance. The sample droplet may include beads. Beads may be added to the sample droplet buffer prior to providing the sample droplet on the droplet operations surface. The sample droplet may be merged with a bead droplet including the beads on the droplet operations surface. The lysis droplet may be provided with the beads. Beads may be added to the lysis buffer prior to providing the lysis droplet on the droplet operations surface. The lysis droplet may be merged with a bead droplet including the beads on the droplet operations surface. The method may include washing the beads to yield a washed bead droplet substantially lacking in unbound material from the sample. The method may include providing an elution droplet on the droplet operations surface, and using one or more droplet operations to combine the elution droplet with the washed bead droplet to yield an eluted droplet in which the target substance may be eluted from the beads. The method may include heating the combined elution droplet and washed bead droplet to accelerate elution of target substance from the beads. The method may include trapping the beads and using one or more droplet operations to transport away from the beads a substantially bead-free droplet on the droplet operations surface. The target substance may include a target protein or target peptide. The target substance may include a target nucleic acid. The method may include supplying the substantially bead-free droplet or the washed bead droplet with reagents for conducting nucleic acid amplification to yield an amplification-ready droplet. One or more droplet operations may be used to combine the substantially bead-free droplet or the washed bead droplet with an amplification reagent droplet including reagents for conducting nucleic acid amplification. The method may include thermal cycling the amplification-ready droplet to amplify the target nucleic acid. The cells may include eukaryotic cells or prokaryotic cells. The cells may include bacterial cells. In some embodiments, the bacterial cells may include cells from *Staphylococcus* species, *Streptococcus* species, *Enterococcus* species, *Pseudomonas* species, *Clostridium* species, and/or *Acinetobacter* species. In some embodiments, the bacterial cells may include cells from *Staphylococcus aureus, Pseudomonas aeruginosa, Clostridium difficile, Acinetobacter baumannii, Bacillus anthracia, Franciscella tularensis, Mycoplasma pneumoniae*, and *Eschericia coli*.

The invention provides a droplet actuator device including a droplet actuator including a electronic storage and/or transmission element. The electronic storage and/or transmission element may be affixed to or incorporated in a droplet actuator. The electronic storage and/or transmission element may be affixed to or incorporated in a droplet actuator cartridge including a droplet actuator. The electronic storage and/or transmission element may include a computer readable data storage element. The computer readable data storage element may include semiconductor memory, magnetic storage, optical storage, volatile memory, non-volatile memory, a radiofrequency identification tag, read-only memory, random access memory, electrically erasable programmable read-only memory, flash memory, and/or a magnetic stripe. The magnetic stripe may be provided on a magnetic stripe card, and the droplet actuator may be mounted on the magnetic stripe card. The droplet actuator mounted on the magnetic stripe card may include electrical contacts arranged to couple with electrical contacts on a droplet actuator instrument when the magnetic stripe card may be inserted in a magnetic card slot of a magnetic card reading instrument. The droplet actuator may be electrically connected to wires on the card. The wires on the card may terminate in contacts arranged to be electrically coupled to electrical contacts on an instrument so that the droplet actuator may be controlled by the instrument. The card may have a shape and size of a standard credit card. The electronic storage and/or transmission element may include a unique identifier for the droplet actuator. The droplet actuator device may be configured with a connect device for connecting the droplet actuator device to a computer as a peripheral device. The connect device may, for example, include a universal serial bus connector. The droplet actuator device may also include a positioning device, such as a global positioning device.

The invention also includes a networked system including the droplet actuator device distributed in a target geographical region with communications capabilities for transmitting data to one or more data aggregation centers. The droplet actuators may be installed on fixed bases. The fixed bases may be selected from the group consisting of: buildings, farms, water supply sources, buoys, and weather balloons. The droplet actuators may be installed on fixed bases. The mobile bases may be selected from the group consisting of: mobile robotic devices, airplanes, unmanned drones, vehicles in vehicle fleets. The mobile bases may be selected from the group consisting of: police cars, school buses, ambulances, military vehicles, oceangoing vessels, postal vehicles, and vehicles in commercial vehicle fleets.

The invention provides a system including the droplet actuator device and a global position sensor. The invention provides a system including one or more kiosks including a dispenser for dispensing a droplet actuator device. The invention provides a system including one or more kiosks including a receptacle for receiving a droplet actuator device. The kiosk may also include an input device for inputting information associated with a droplet actuator device.

DEFINITIONS

As used herein, the following terms have the meanings indicated.

"Activate" with reference to one or more electrodes means effecting a change in the electrical state of the one or more electrodes which, in the presence of a droplet, results in a droplet operation.

"Bead," with respect to beads on a droplet actuator, means any bead or particle capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The fluids may include one or more magnetically responsive and/or non-magnetically responsive beads. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic liquid, serum, plasma, sweat, tear, saliva, sputum, cerebrospinal liquid, amniotic liquid, seminal liquid, vaginal excretion, serous liquid, synovial liquid, pericardial liquid, peritoneal liquid, pleural liquid, transudates, exudates, cystic liquid, bile, urine, gastric liquid, intestinal liquid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006; and Roux et al., U.S. Patent Pub. No. 20050179746, entitled "Device for Controlling the Displacement of a Drop Between two or Several Solid Substrates," published on Aug. 18, 2005; the disclosures of which are incorporated herein by reference. Certain droplet actuators will include a substrate, droplet operations electrodes associated with the substrate, one or more dielectric and/or hydrophobic layers atop the substrate and/or electrodes forming a droplet operations surface, and optionally, a top substrate separated from the droplet operations surface by a gap. One or more reference electrodes may be provided on the top and/or bottom substrates and/or in the gap. In various embodiments, the manipulation of droplets by a droplet actuator may be electrode mediated, e.g., electrowetting mediated or dielectrophoresis mediated or Coulombic force mediated. Examples of other methods of controlling liquid flow that may be used in the droplet actuators of the invention include devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles.

"Filler fluid" means a liquid associated with a droplet operations substrate of a droplet actuator, which liquid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; International Patent Application No. PCT/US2008/072604, entitled "Use of additives for enhancing droplet actuation," filed on Aug. 8, 2008; and U.S. Patent Publication No. 20080283414, entitled "Electrowetting Devices," filed on May 17, 2007; the entire disclosures of which are incorporated herein by reference. The filler fluid may fill the entire gap of the droplet actuator or may coat one or more surfaces of the droplet actuator. Filler fluid may be conductive or non-conductive.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

BRIEF DESCRIPTION OF THE DRAWINGS

FIG. 1A shows the reagent storage cassette and an open position. FIG. 1B shows the reagent storage cassette in a closed position.

FIG. 2A shows the reagent storage cassette and an open position. FIG. 2B shows an alternative embodiment of the reagent storage cassette in a closed position where the film includes a pull tab.

FIG. 3A illustrates a segment of the bottom member with the protective film in place. FIG. 3B illustrates the segment of the bottom member with plungers fully inserted to force droplets from storage reservoirs. FIGS. 3C and 3D illustrate a corresponding segment of a top member of a reagent storage cassette juxtaposed with the cross sectional view of a segment of the bottom member of the reagent storage cassette. In FIG. 3C, the droplets are present in the reservoirs. In FIG. 3D, plungers are fully inserted to force droplets from storage reservoirs. FIG. 3E illustrates an end-wise cross-sectional view of the reagent storage cassette showing a section of the top member juxtaposed with a corresponding section of the bottom member.

FIG. 6A shows liquid in a reservoir outside the droplet operations gap, prior to being forced into the droplet operations gap. FIG. 6B shows a top view of a reservoir electrode through which liquid is supplied into the droplet operations gap of the droplet actuator. FIG. 6C illustrates puncturing the dielectric layer so that liquid may flow into the droplet operations gap. FIG. 6D illustrates the plunger fully inserted and liquid having been forced into the droplet operations gap. FIG. 6E shows an alternative embodiment in which a single electrode is provided on a top substrate of the droplet actuator. FIG. 6F illustrates an alternative embodiment in which a reservoir electrode and droplet operations electrodes are provide on the top substrate and a ground or reference electrode is provided on the bottom substrate.

FIG. 13A illustrates the system generally, while FIGS. 13B-13I each illustrate a specific step in a loading process.

FIG. 14A illustrates the system generally, while FIGS. 14B-14F each illustrate a specific step in a loading process.

DESCRIPTION

Figure 1A:
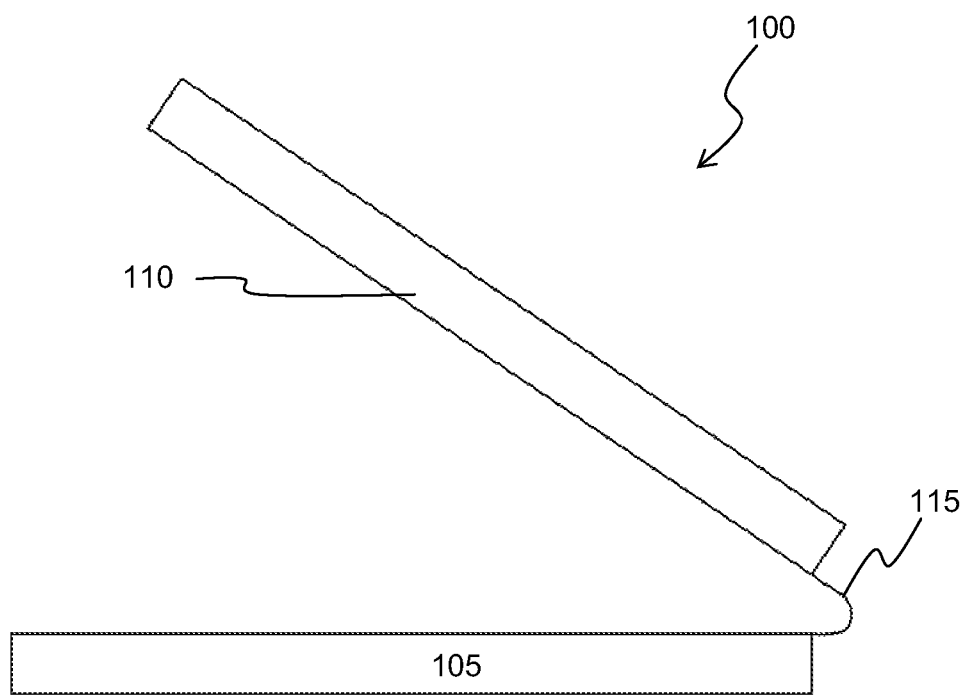
FIGS. 1A and 1B illustrate a reagent storage cassette of the invention.

The invention provides droplet actuator devices, techniques and systems for making and using droplet actuators. The invention provides devices, techniques and systems for preparing samples and/or reagents for loading onto a droplet actuator; for loading samples and/or reagents onto a droplet actuator; for storing samples and/or reagents on a droplet actuator and/or for use on a droplet actuator; and/or for conducting droplet operations using samples and/or reagents on a droplet actuator. The invention also provides devices, techniques and systems for conducting flow through bead handling and washing. For example, the invention provides techniques for splitting droplets in a flow-through system, compartmentalizing beads in droplets in a flow-through system, and washing droplets in a flow-through system. The invention provides droplet actuator devices, techniques and systems for making and using droplet actuators to process viscous, solid or semi-solid samples. For example, the invention provides techniques for processing viscous, semisolid, and/or solid samples. The invention provides droplet actuator devices including a gel for use in gel electrophoresis, along with techniques and systems for conducting gel electrophoresis on a droplet actuator. The invention provides a fluidics system and technique for using the system for loading liquids onto a droplet actuator. The invention also provides droplet actuators loaded using the fluidics system and method of the invention and methods of using such droplet actuators to conduct droplet operations. The invention provides droplet actuator devices, techniques and systems for processing samples for use on a droplet actuator device. In some cases, the processing includes pre-processing steps conducted prior to introduction of the samples onto a droplet actuator. The invention provides droplet actuator devices, techniques and systems for capturing, concentrating and/or eluting nucleic acids; and sensitively isolating nucleic acids using one or more droplet operations to perform separation protocols. The invention also provides kits including droplet actuators of the invention along with various other components suitable for executing the techniques of the invention, such as reagents, sample collection devices, and/or instructions.

7.1 Liquid Storage and Loading

The invention provides devices, techniques and systems for preparing samples and/or reagents for loading onto a droplet actuator; for loading samples and/or reagents onto a droplet actuator; for storing samples and/or reagents on a droplet actuator and/or for use on a droplet actuator; and/or for conducting droplet operations using samples and/or reagents on a droplet actuator. The reagents may be stored on the droplet actuator itself, and/or in reagent storage containers that are provided with a droplet actuator cartridge. In some cases, the droplet actuator cartridge may be provided in a kit along with reagents stored and storage containers.

Reagents selected for storage in accordance with the invention may be reagents which are useful in conducting an assay. For example, the reagents may be useful in an assay for assessing the presence or absence of, and/or quantify the amount of, a chemical or a biochemical substance. Examples of suitable assay types include immunoassays, nucleic acid amplification assays, nucleic acid sequencing assays, enzymatic assays, and other forms of assays. Assays may be conducted with various purposes; examples include medical diagnostics, veterinary diagnostics, weapons or explosives detection, chemical weapons detection, biological weapons detection, environmental testing, water testing, air testing, soil testing, food quality testing, forensics, species identification etc.

Samples may be collected and tested at a point of sample collection. For example, the point of sample collection may be in a medical care facility, at a subject's bedside, in a laboratory, or in the field. A sample may be collected, loaded onto the droplet actuator cartridge; the cartridge may be inserted into an instrument, an assay may be run, and results may be provided, all at the point of sample collection. In other embodiments, one or more of these steps may be accomplished remotely from the point of sample collection, e.g., in a central laboratory. A sample may be collected in the field, and transported to a laboratory, where it is loaded into a cartridge which is mounted on an instrument; the assay may be run, and results provided. A sample may be collected in the field and loaded into a cartridge in the field, e.g., loaded into a sample reservoir in a droplet actuator cartridge; the cartridge may be returned to a laboratory, where it is mounted on an instrument, an assay is run, and results are provided. Various other combinations are also possible within the scope the invention. The instrument may include electronic and detection components, as well as a means for mounting the cartridge on the instrument, or otherwise coupling the cartridge to the instrument, in a manner in which aligns electronic and detection components with corresponding components or regions of the droplet actuator. The cartridge may include a droplet actuator, electrical components which correspond to the electrical components of the instrument, and one or more detection regions, which are aligned with detection components on the instrument. In various embodiments, the reagent storage and loading techniques described in this specification may also be used for loading sample, e.g., sample may be collected and loaded into a reservoir, where it is stored. Sample may be loaded from the reservoir into the droplet operations gap of the droplet actuator cartridge in preparation for conducting an assay using the droplet actuator cartridge.

The reagent storage and reconstitution techniques of the invention may be useful in a variety of fluidics devices, such as droplet actuator devices. In some cases, the devices of the invention are packaged with or include reagents. The reagents may be provided in a format that is suitable for use in the field. In certain embodiments, the devices are suitable for use without requiring refrigeration and/or specialized dispensing equipment. Reagents may be rapidly reconstituted and used in express testing. Assay results, currently available by in-laboratory testing, may be made available substantially in 'real-time.' Decisions made using assay results can be made more quickly.

Figure 1B:
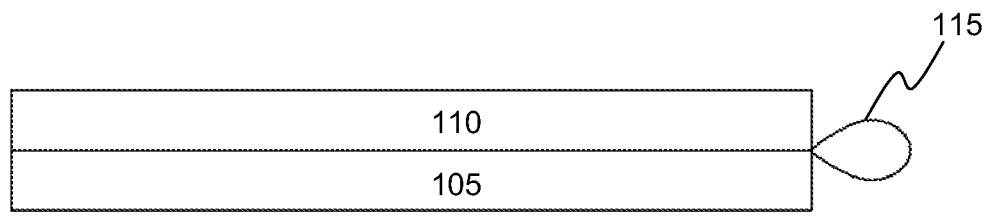

FIG. 1 illustrates a reagent storage cassette 100 of the invention. Cassette 100 includes a bottom member 105 and a top member 110. Bottom member 105 and a top member 110 may be coupled by a flexible hinge portion or member 115. FIG. 1A shows bottom member 105 and a top member 110 in an open position. FIG. 1B shows bottom member 105 and a top member 110 in a closed position. In one embodiment, the storage cassette is provided with bottom member 105 and a top member 110 in an open position, and the cassette is manipulated by a user into the closed position shown in FIG. 1B. The flexible member 115 may have different electrical and physical properties in the regions overlying bottom member 105, overlying top member 110, and at the hinge and thus can comprise of multiple materials or a same material with different properties or a same material with substantially similar properties. The flexible member 115 may be an insulating material that serves dual purpose of insulating the electrodes on substrate 105 that are used for effecting droplet operations and also serve as a tether to the top plate. The flexible member 115 may have different properties in the portions overlying members 105 and 110 so that it is insulating on bottom member 105 but substantially conductive on top member 110 or vice versa. In other embodiments, the flexible member 115 may be rigid over members 105 and 110 but flexible only at the hinge connecting both the members. In another embodiment, the flexible member may also comprise a gasket or standoff material that forms a gap between the members 105 and 110 so that droplets can reside between members 105 and 110. The flexible member may also be hydrophobized so that it is ready for droplet operations.

Figure 2A:
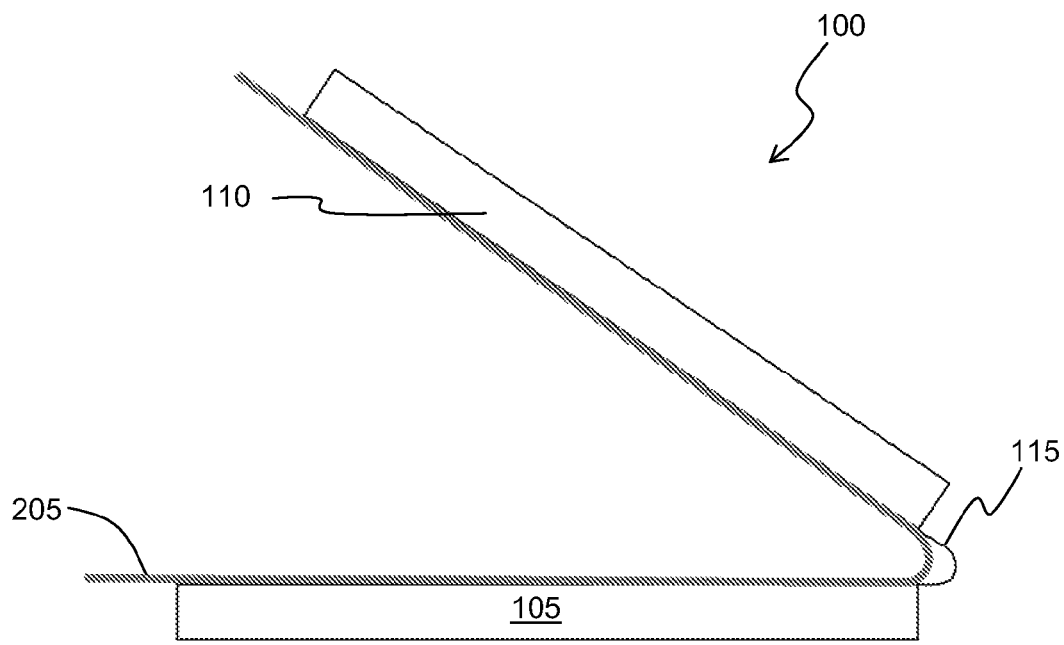
FIGS. 2A and 2B illustrate a reagent storage cassette of the invention including a protective film configured to protect reagents from contamination and/or prevent leaking of reagents.
Figure 2B:
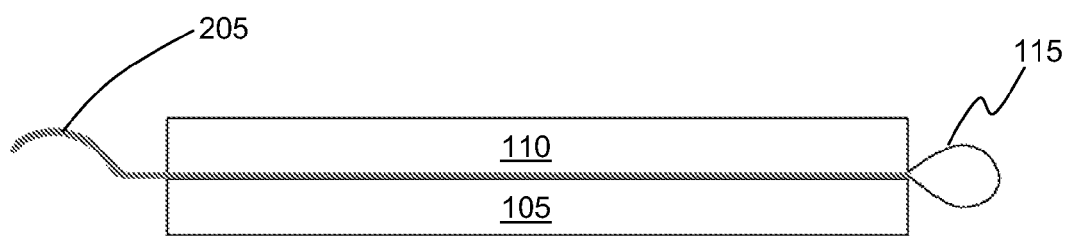

FIG. 2 illustrates a reagent storage cassette 100 of the invention with protective film 205. Protective film 205 may be included to provide a seal, enclosing reagent components to protect them from the environment and/or separating reagent components from one another. One embodiment, shown in FIG. 2A illustrates a protective film 205 covering facing surfaces of the bottom member 105 and a top member 110 of cassette 100. In operation, protective film 205 is removed to expose reagent components, and then bottom member 105 and a top member 110 of cassette 100 are sealed together. FIG. 2B illustrates a protective film inserted between facing surfaces of the bottom member 105 and a top member 110 of cassette 100. In operation, protective film 205 is removed to expose reagent components in bottom member 105 to reagent components in top member 110 of cassette 100. The protective film can also serve as a removable insulating or hydrophobic material. After droplet operations are performed, the members 110 and 105 may be separated and a new film 205 may be attached so that the surfaces of the droplet actuator are clean and can be reused without any concern for cross contamination.

FIG. 3 illustrates cross-sectional views 300 of a segment of bottom member 105. Bottom member 105 includes reservoir 305 formed therein, which serve as reservoirs for droplets 315 of liquid reagents or samples. Openings 310 provide a liquid path for forcing droplets 315 onto a surface of bottom member 105. During storage, protective film 205, illustrated in FIG. 3A, may be maintained in place to seal droplets 315 in reservoirs 310. Droplets 315 may be pre-metered; however, in some cases, exact premetering is not required, since the droplets will be subject to dispensing operations on the droplet actuator in which dispensed subdroplets will have precise volumes suitable for conducting assays.

Figure 3A:
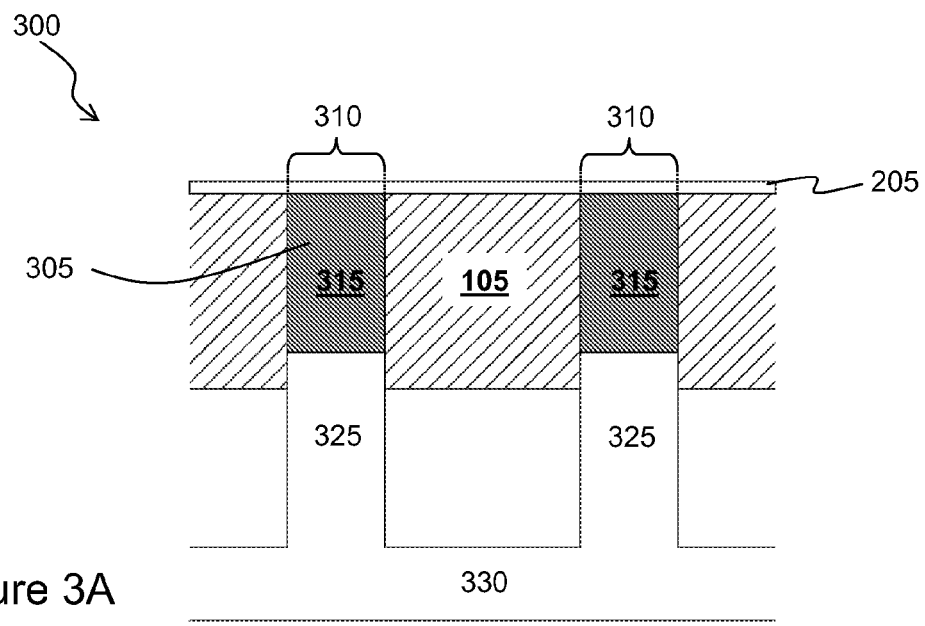
FIGS. 3A, 3B, 3C, 3D, and 3E show cross-sectional views of segments of top and bottom members of a reagent storage cassette of the invention that makes use of plungers to force droplets from storage reservoirs.

Reservoir 305 is associated with plungers 325 and plunger depressor 330. Plunger depressor 330 is configured to force plungers 325 into openings 310, thereby forcing droplets 315 out of openings 310. Plunger depressor 330 may be manually operated, such that an operator may, by applying pressure to plunger depressor 330, force plungers 325 into openings 310, thereby forcing droplets 315 out of openings 310. Plunger depressor 330 may be automatically operated, for example, so that when an operator inserts the droplet actuator cartridge into an instrument, the active insertion also forces plunger depressor 330 to move plungers through 25 into openings 310. While reservoir/plunger assemblies are illustrated in FIGS. 3A/3B, it will be appreciated that in some cases only a single such reservoir/plunger assembly is required. In other cases, more than two reservoir/plunger assemblies may be provided.

Prior to forcing plungers 325 into openings 310, protective film 205 may be removed. Alternatively, protective film 205 may be scored or otherwise weakened in regions atop openings 310 so that by applying pressure to plunger depressor 330, droplets 315 may be forced out of openings 310 and through protective film 205. In yet another embodiment, an awl, scribe, needle, or other puncturing component may be used to puncture or weaken protective film 205. For example, top member 110 may be equipped with an awl, scribe or other component configured to puncture or weaken protective film 205 when bottom member 105 and top member 110 are fitted together.

One or more of droplets 315 may be a fully constituted reagent. One or more of droplets 315 may, when forced out of opening 310, contact and combine with one or more reagents on surface of bottom member 105 and/or top member 110 of cassette 100 to yield a fully constituted reagent. In another embodiment, droplet 315 constitutes a sample. For example, a sample may be loaded in reservoir 305 at a point of sample collection, and may later be loaded in accordance with the reagent loading techniques described herein. In another embodiment, droplet 315 constitutes a standard solution with known amount of material that can either be used as a calibrant or can be diluted using droplet operations to setup a standard curve using multiple concentrations derived from performing dilutions.

In some embodiments, protective film 205 also serves as an adhesive and/or dielectric layer. For example, a droplet actuator substrate 105 may include electrodes (not shown) associated with substrate 105. Protective film 205 may be a dielectric layer atop the electrodes, arranged such that the electrodes may be used to conduct droplet operations atop protective film 205. Protective film 205 may or may not be bound to substrate 105 using an adhesive layer. A hydrophilic coating (not shown) may, in some cases, be provided atop protective film 205.

Substrate 105 may be any rigid substrate, such as a silicon, PCB, plastic, or other polymeric substrate. Electrodes may be any material which is suitably conductive to permit electrodes to mediate droplet operations atop protective film 205. Examples include copper, chrome, aluminum, gold, silver, indium tin oxide, and other conductive materials. The adhesive layer, when present, may be any adhesive which is suitable for binding protective film 205 to the underlying layers of substrate 105. In alternative embodiments, the adhesive layer may be absent. Protective film 205 may be any dielectric material, and hydrophobic coating may be any hydrophobic coating that binds to the underlying layers in a manner which is sufficient to permit one or more droplet operations to be conducted atop droplet actuator substrate 105. The protective film 205 may be coated with a hydrophobic layer. Examples of suitable hydrophobic coatings include fluoropolymers and perfluoroploymers, such as polytetrafluoroethylenes; perfluoroalkoxy polymer resins; fluorinated ethylene-propylenes; polyethylenetetrafluoroethylenes; polyvinylfluorides; polyethylenechlorotrifluoroethylenes; polyvinylidene fluorides; polychlorotrifluoroethylenes; and perfluoropolyethers. In one embodiment, the hydrophobic coating includes an amorphous Teflon fluoropolymer or a TEFLON® fluoropolymer. In another embodiment, the hydrophobic coating includes a CYTOP™ perfluoropolymer.

In one embodiment, an adhesive layer binds protective film 205 to electrodes and substrate 105. In one example, protective film 205 is a polyimide film. In yet another example, the adhesive layer includes an acrylic adhesive. In still another example, an adhesive-backed polyimide film provides adhesive layer and protective film 205. For example, adhesive-backed polyimide film may be a PYRALUX® LF flexible composite (DuPont). PYRALUX® LF7013, for example is an approximately 13 μM viscous, solid or semi-solid DuPont KAPTON® polyimide film and 25 μM viscous, solid or semi-solid acrylic adhesive. Other examples of suitable adhesive-backed films include PYRALUX® LF LF0110, LF0120, LF0130, LF0150, LF0210, LF0220, LF0230, LF0250, LF0310, LF7001, LF7082, LF1510, and LF7034.

In some embodiments, the adhesive is selected to be releasable, so that the adhesive-backed film may be removed following use and replaced with a fresh adhesive-backed film. In some embodiments, the adhesive may serve as the protective film and the backing may serve as a hydrophobic coating. In other embodiments, the dielectric may be formed as a permanent part of the substrate, and a protective film having a hydrophilic backing may be applied to the permanent dielectric. In yet another embodiment, multiple films may be used and replaced together or separately. For example, a hydrophobic film may be used atop a protective film, and both films may be applied atop a droplet actuator substrate including electrodes. Each of the hydrophobic film and protective film may be replaced together or separately, as needed.

In one embodiment, the protective film includes a dielectric film, and the droplet actuator substrate includes the substrate, electrodes and a dielectric atop the substrate. The protective film is placed atop the dielectric, and an adhesive may optionally be included between the dielectric and the protective film.

In another embodiment, the protective film includes a dielectric film, and the droplet actuator substrate includes the substrate, electrodes and a dielectric atop the substrate. The protective film may be placed atop the dielectric, and an adhesive may optionally be included between the dielectric and the protective film. Alternatively, the droplet actuator substrate may include the substrate and electrodes with no dielectric atop the substrate. The protective film may be placed atop the substrate and electrodes, and an adhesive may optionally be included between the substrate and electrodes and the film.

Top member 110 may be equipped with an awl, scribe or other component configured to puncture or weaken protective film 205 when bottom member 105 and top member 110 are fitted together. Plungers 325 may be equipped with an awl, scribe or other component configured to puncture or weaken protective film 205 when plungers 325 are inserted in reservoirs 305. Once liquid 315 is forced atop substrate 105, electrodes associated with top member 110 and/or bottom member 105 may be used to effect droplet operations using droplets 315. In certain embodiments, the awl, scribe or other component configured to puncture or weaken protective film has a hydrophobic surface.

In yet another embodiment, the protective film may double as a hydrophobic layer. For example, the wells may be located in the top substrate and separated from the gap by the protective film, doubling as a hydrophobic layer. The protective film may be punctured during loading of droplets into the gap, e.g., by an awl, scribe or other component configured to puncture or weaken protective film, permitting droplets to flow through the punctured region and into the gap where they are subject to droplet operations. In certain embodiments, the awl, scribe or other component configured to puncture or weaken protective film has a hydrophobic surface.

In an alternative embodiment, the top substrate and bottom substrate are provided bound together, and separated to provide a droplet operations gap. In this embodiment, the droplets 315 would be forced by the plungers 325 into the gap, where they would be subject to droplet operations using electrodes associated with the top member 110 and/or the bottom member 105.

Figure 3B:
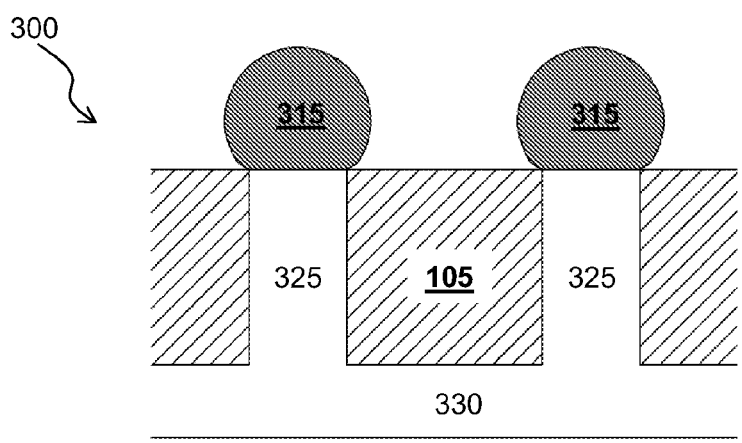
Figure 3C:
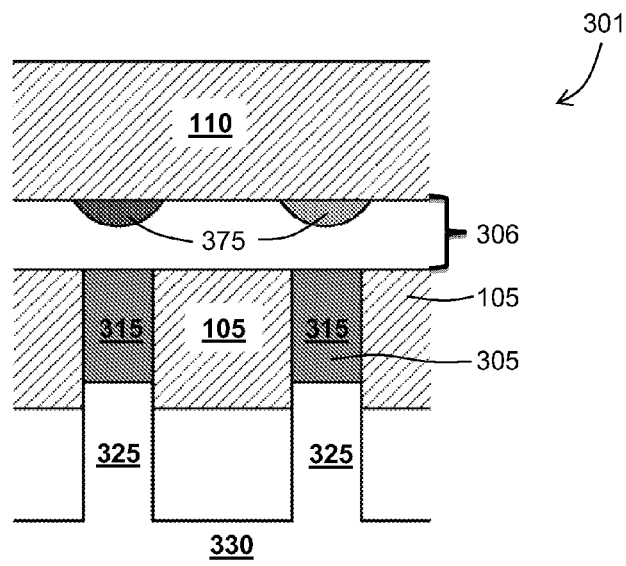
Figure 3D:
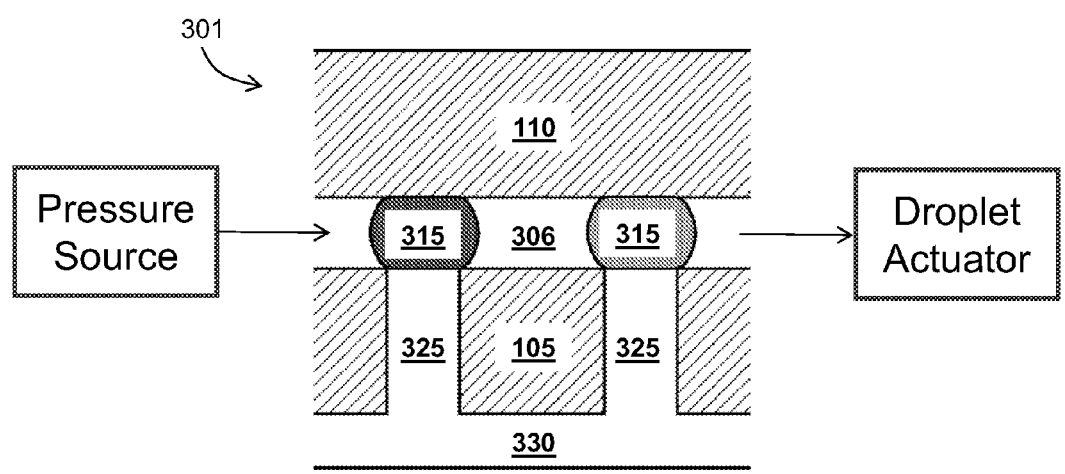

FIGS. 3C and 3D illustrates a length-wise cross sectional view 301 of a segment of top member 110 juxtaposed with a cross sectional view 300 of a segment of bottom member 105 described with reference to FIG. 3B. As shown in FIG. 3C, top member 110 includes dried reagent 375 affixed thereto. When droplet 315 is forced out of its opening and into contact with dried reagent 375, droplet 315 combines with dried reagent 375 to yield a fully constituted reagent, as illustrated in FIG. 3D.

Figure 3E:
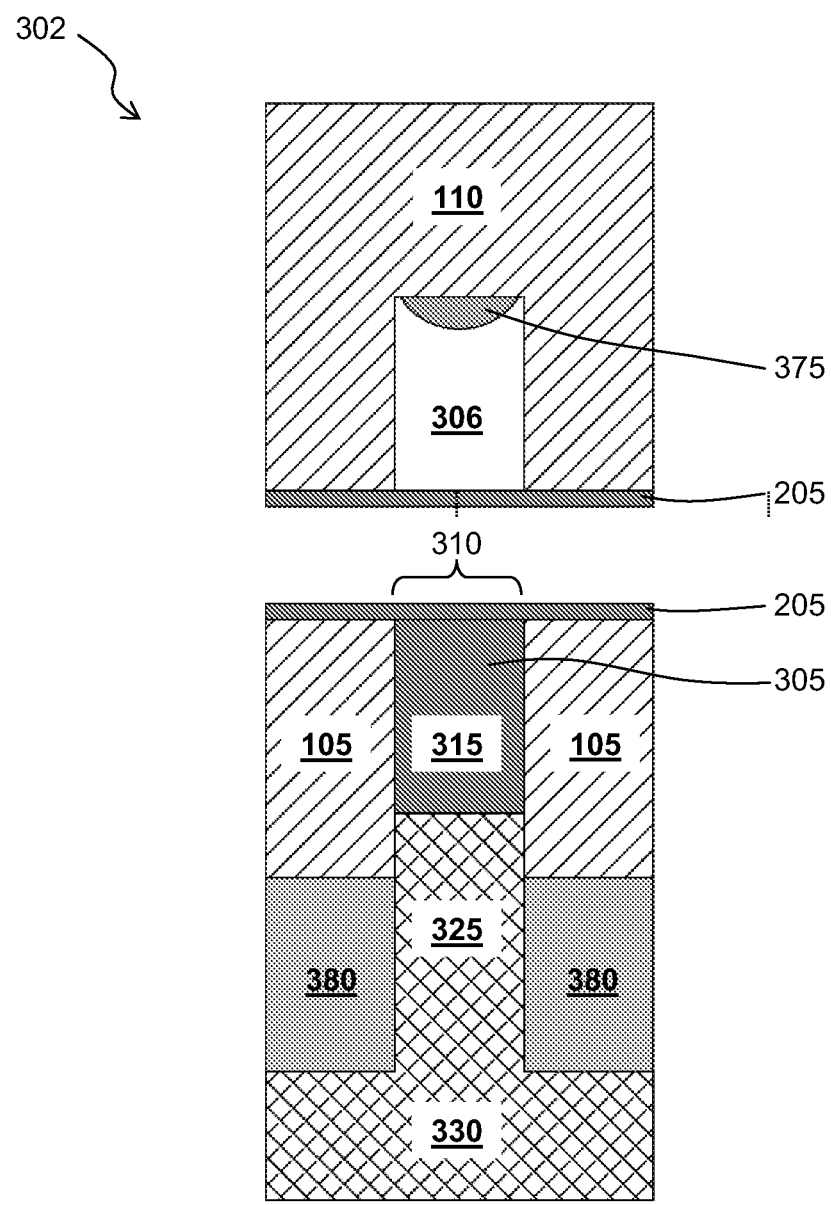

FIG. 3E illustrates an end-wise cross-sectional view of reagent storage cassette 302 showing top member 110 juxtaposed with bottom member 105. Top member 110 includes channel 306, which may be any type of liquid path. Bottom member 105 includes reservoirs 305 formed therein. Film 205 seals channel 306 and reservoir 305. Reservoir 305 includes a liquid, such as a sample or a reagent or a calibrant. Cassette 302 may include multiple reservoirs. Channel 306 may include one or more dried, concentrated or viscous, solid or semi-solidened reagents 375. Each dried, concentrated or viscous, solid or semi-solidened reagent 375 may be aligned with a corresponding reservoir 305, such that when liquid 315 is caused to flow into channel 306, each dried reagent 375 is combined with a droplet of liquid 315 to yield a constituted reagent. Reservoir 305 is associated with plungers 325 and plunger depressor 330. Plunger depressor 330 is configured to permit a user to force plungers 325 into reservoir 305, thereby forcing droplets 315 out of openings 310 and into channel 306. Reservoir 305 is thus bounded and substantially sealed by substrate 105 along opening 310, film 205 and plunger 325. In some embodiments, compressible material 380 may be provided between plunger compressor 330 and bottom member 105 to retain plunger 325 in place during storage and shipment.

In operation, film 205 may be removed. Plunger 325 may be forced into reservoir 305, thereby forcing liquid 315 into channel 306. A series of such liquids 315 may be forced into channel 306, thereby forming a series of droplets separated by a filler fluid. In cases where the reagent storage cassette is provided as an integral part of a droplet actuator cartridge, droplets 315 may be transported and from the reagent storage cassette into another region of the cartridge. For example, reagent droplets 315 may be transported from the reagent storage cassette into a droplet operations gap of a droplet actuator. Similarly, droplets 315 may be transported from the reagent storage cassette into a reservoir of a droplet actuator, from where they may be transported through a liquid path into a droplet operations gap of a droplet actuator. In the droplet operations gap, droplets 315 and/or sub-droplets dispensed therefrom may be subjected to droplet operations. For example, the droplet operations may be part of a droplet operations protocol which is designed to use droplets 315 to perform an assay.

In some embodiments, a pressure source may provide pressure for forcing droplets from the reagent storage cassette into a droplet actuator, or into another region of a droplet actuator cassette. As illustrated in FIG. 3D, a pressure source may forced droplets 315 through channel 306 and into the droplet actuator. Channel 306 may be in any configuration, for example, it may be linear or curvilinear. Channel 306 may be provided generally in a common plane with a droplet operations gap, such that droplets 315 may flow along a common plane through channel 306 and into the droplet operations gap. Alternatively, channel 306 may be provided in a different plane than the plane of the droplet operations gap. For example, channel 306 may be located in a plane which is separate, but parallel to the playing of the droplet operations gap. A liquid passage may connect channel 306 to the droplet operations gap, such that the pressure source may cause the droplets 315 to flow through channel 306, through the connecting liquid passage, and into the droplet operations gap. In yet another embodiment, the channel 306 need not be parallel to the droplet operations gap, e.g., the channel may be in a position relative to the droplet operations gap which establishes an angle which is between 0 and 180°.

In one embodiment, pressure may be applied to the contents of channel 306, thereby forcing droplets and filler fluid into a droplet operations gap of the droplet actuator. Alternatively, a vacuum source may be used to pull the contents of channel 306 into a droplet operations gap of a droplet actuator. Further, channel 306 may itself be associated with electrodes capable of effecting forces suitable for causing the transport of droplets 315 along the path of channel 306. Such electrodes may, for example, form a path having one or more electrode members which are adjacent to electrode members in a droplet operations gap of a droplet actuator. In this manner, the electrodes may be used to transport one or more droplets through channel 306, and from channel 306 into a droplet operations gap of a droplet actuator.

Figure 4:
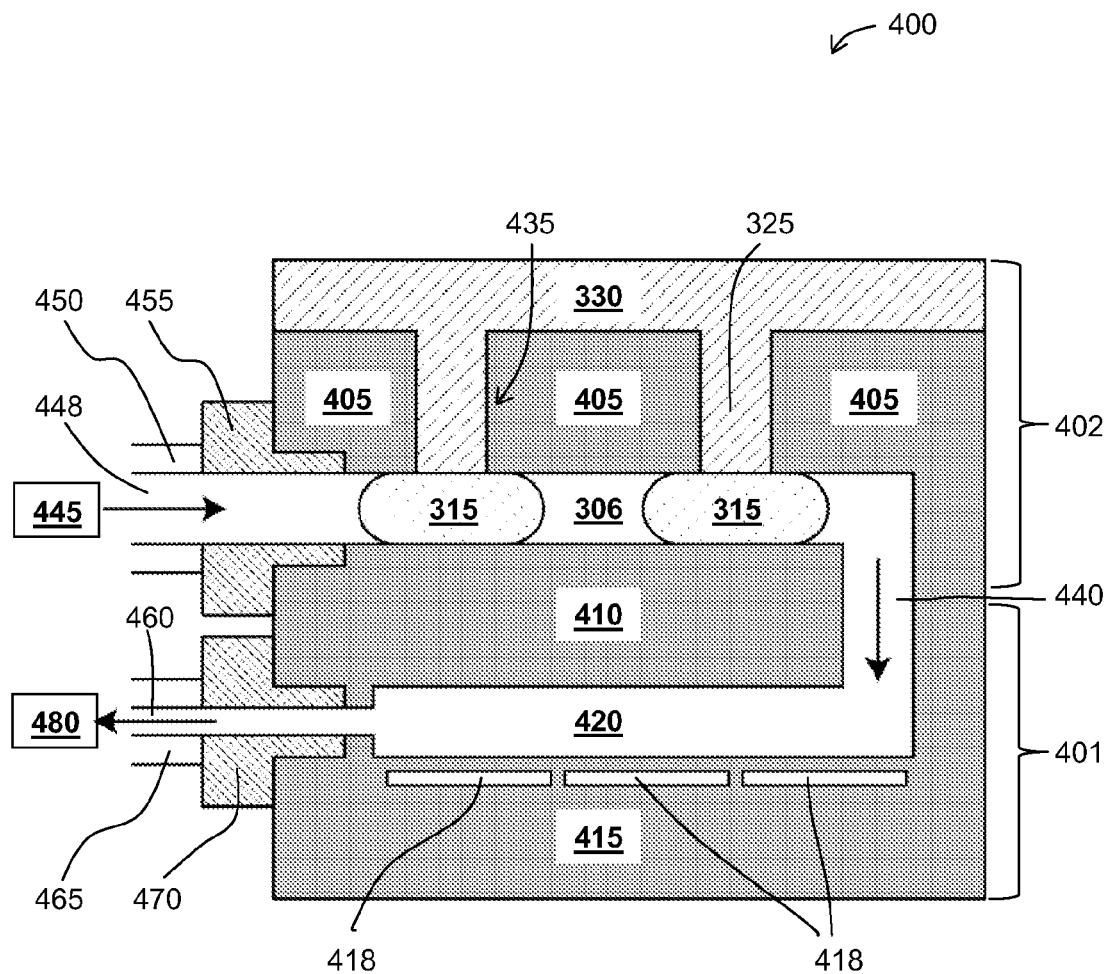
FIG. 4 illustrates another embodiment of the invention in which a droplet actuator cartridge is provided with a droplet actuator portion an integral reagent cassette portion.

FIG. 4 illustrates another embodiment of the invention in which a droplet actuator cartridge 400 is provided with a droplet actuator portion 401 and an integral reagent cassette portion 402. In the embodiment illustrated, droplet actuator portion 401 includes top substrate 410 separated from bottom substrate 415 by droplet operations gap 420. Bottom substrate 415 includes electrodes 418 arranged for conducting one of more droplet operations in droplet operations gap 420. It will also be appreciated that one or more droplet operations and/or reference electrodes may be associated with top substrate 410 and/or bottom substrate 415. Reagent cassette portion 402 includes bottom substrate 410, which is the same as top substrate 410 of droplet actuator portion 401. Reagent cassette portion 402 also includes top substrate 405, which includes reservoirs 435 formed therein. As illustrated, plungers 325 are inserted into reservoirs 435. Channel 306 is formed in top substrate 405 and/or bottom substrate 410. Channel 306 is connected to droplet actuator gap 420 by liquid path 440. Channel 306 may also be coupled to a pressure source 445 configured for providing pressure into channel 306. Pressure source 445 may be coupled to channel 306 by a liquid path 448 established, for example, by capillary tube 450 and associated fitting 455. Similarly, an output flow path 460 may be coupled to droplet operations gap 420; the coupling may, for example, be established by a capillary tube 465 and associated fitting 470. In this manner, a liquid path is established from pressure source 445 through liquid path 448, through channel 306, through connecting liquid path 440, through droplet operations gap 420, and through exit liquid path 460. In some cases, rather than a pressure source 445, a vacuum source 480 may be coupled via liquid path 460 to droplet operations gap 420. In operation, droplets 315 may be stored in reservoirs 435. A film (not shown) may be provided over openings to reservoirs 435 to retain droplets 315 therein. As noted above, the film may be scored in order to facilitate breaking of the film upon application of pressure thereto by insertion of plungers 325. Alternatively, a puncturing device may be employed, e.g., as illustrated below with respect to FIG. 6. In any case, plungers 325 may be forced into reservoirs 435, thereby forcing droplets 315 into channel 306. Pressure from pressure source 445 and/or vacuum from vacuum source 480 may be used to cause droplets 315 to flow through channel 306, through liquid path 440, and into droplet operations gap 420 where such droplets may be subject to droplet operations mediated by electrodes 418. In an alternative embodiment, droplet operations and/or reference electrodes may be associated with surfaces adjacent to channel 306 and/or connecting liquid path 440, and droplets 315 may be transported into droplet operations gap using one or more droplet operations facilitated by such electrodes. The figure is illustrative, and many other embodiments are possible. For example, FIG. 4 can be considered as a top view (top plate not shown and 410 serves as only a gasket with no electrodes) where the plungers are inserted within the gap of the droplet actuator and electrodes 418 move to underneath the channel 420 while 415 serves as a gasket.

Figure 5A:
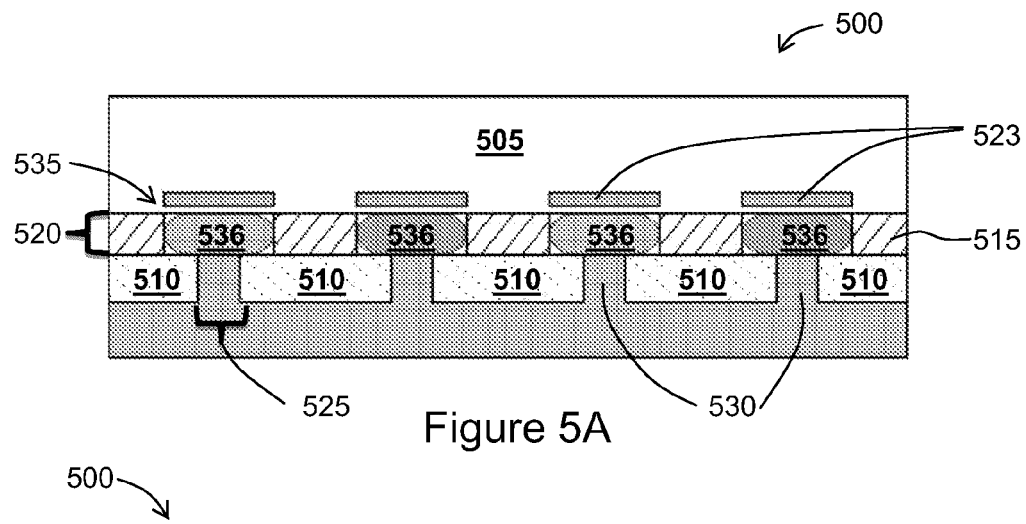
FIGS. 5A and 5B illustrate a side cross-sectional view and a top view, respectively, of a droplet actuator configured to supply droplets into reservoirs in a droplet operations gap.
Figure 5B:
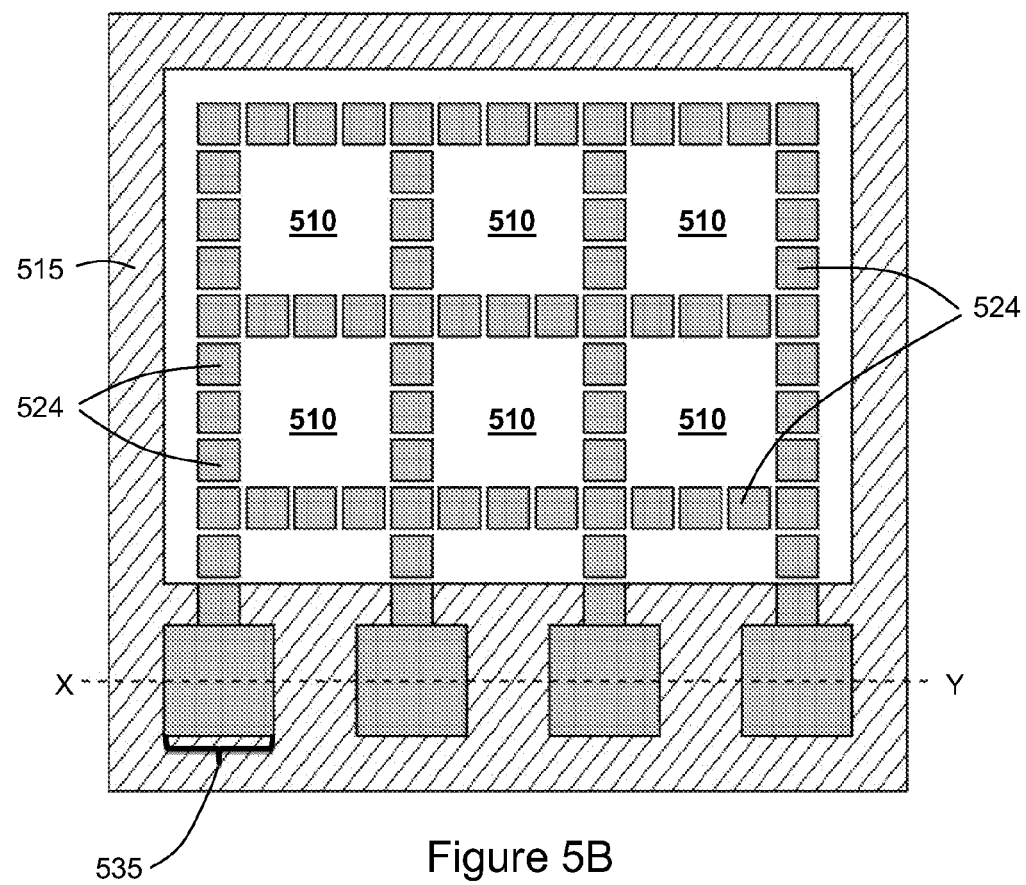

FIGS. 5A and 5B illustrate a side cross-sectional view and a top view, respectively, of a droplet actuator 500 according to the invention. Droplet actuator 500 is like droplet actuator 400, except that rather than forcing droplets into a channel, which is used to supply droplets into a droplet operations gap, droplet actuator 500 supplies droplets directly into reservoirs in a droplet operations gap. One or more sub-droplets may be dispensed from the reservoirs. Droplet actuator 500 includes top substrate 505 and bottom substrate 510, separated by gasket 515 to form gap 520. Top substrate 505 includes droplet operations electrodes 523, though it will be appreciated that as described elsewhere herein, in an alternative embodiment, droplet operations electrodes 523 may be supplied on bottom substrate 510 rather than top substrate 505. Bottom substrate 510 also includes reservoirs 525 into which plungers 530 are inserted. Gasket 515 also forms reservoirs 535 in droplet operations gap 520. Each reservoir 535 includes an electrode 523 associated with top substrate 505 and aligned with reservoir 535. Adjacent to each electrode 523 is a path of droplet operations electrodes 524. The paths of droplet operations electrodes 524 are arranged in a network of paths. It will be appreciated that the network of paths illustrated in FIG. 5B is illustrative only, and that a wide variety of similar such networks is possible within the scope of the invention. FIG. 5A shows droplets 536, including one droplet in each reservoir 535. As illustrated, the droplets have been forced in the place using plungers 530, i.e., by forcing plungers 530 into reservoirs 525. In operation, droplet actuator 500 may include a protective film as described herein, which may be removed and/or punctured prior to forcing droplets 536 into place within reservoirs 535. Ideally, the top surface of each plunger is hydrophobic or is coated with a hydrophobic material in order to facilitate droplet operations conducted using electrodes 523 and 524. Further, the surface of reservoir 525 and/or reservoir 535 may also be hydrophobic or coated with a hydrophobic material.

Figure 6A:
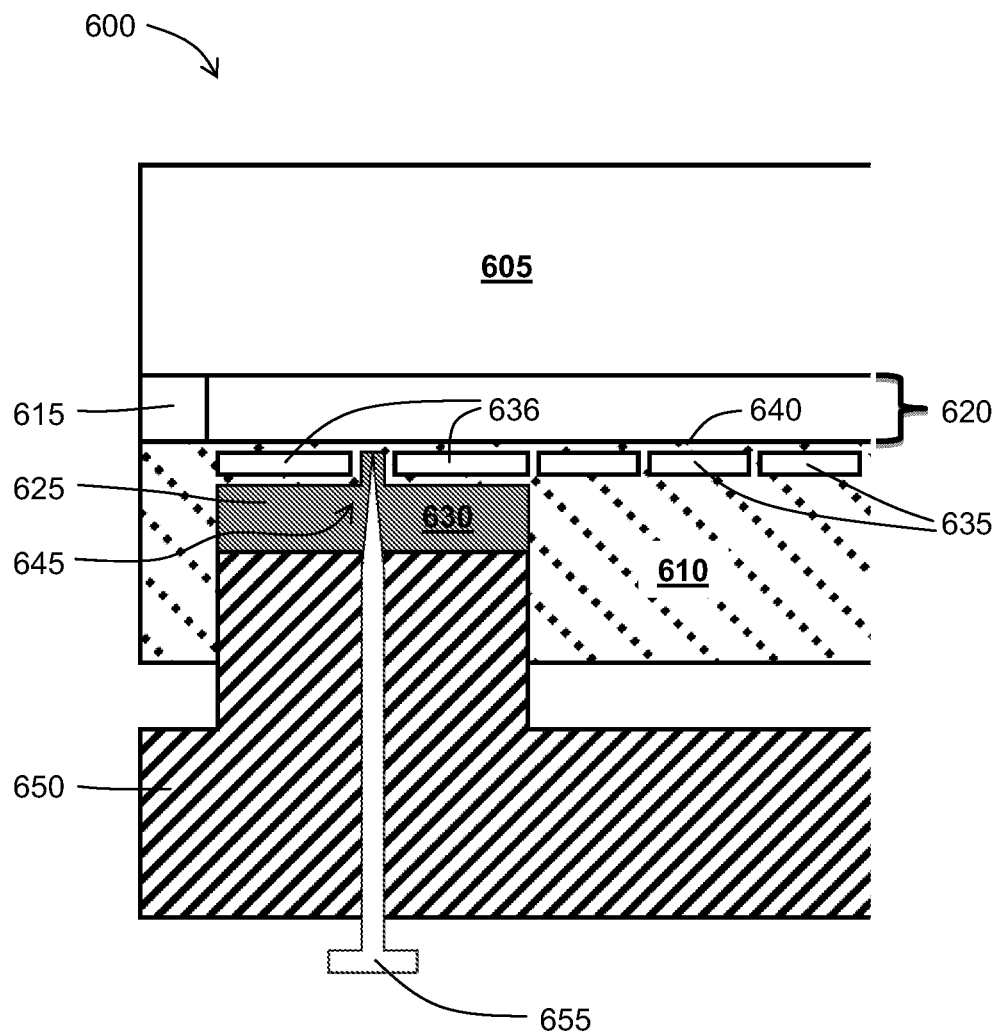
FIGS. 6A, 6B, 6C, 6D, 6E, and 6F illustrate another aspect of the invention in which a plunger is used to force liquid into the droplet operations gap of a droplet actuator.

FIGS. 6A, 6B, 6C, 6D, 6E, and 6F illustrate another aspect of the invention in which a plunger is used to force liquid into the droplet operations gap of a droplet actuator. As illustrated in FIG. 6A, droplet actuator 600 includes a top substrate 605 and a bottom substrate 610 separated by gasket 615 the form drop operations gap 620. Reservoir 625 is formed on bottom substrate 610. As illustrated, reservoir 625 includes a liquid 630, which may, for example, include reagent and/or sample. Bottom substrate 610 further includes electrodes 635 arranged for conducting droplet operations in the droplet operations gap. Bottom substrate 610 further includes an electrode 636, which includes an opening 637 therein. FIG. 6A shows liquid 630 in reservoir 625 outside the droplet operations gap 620, prior to being forced by plunger 650 into the droplet operations gap 620.

Figure 6B:
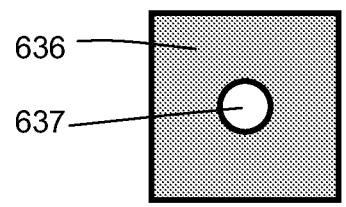

FIG. 6B shows a top view of electrode 636. Opening 637 is shown as being centrally located, but it will be appreciated that the opening may be provided in any region of electrode 636. Further, in an alternative embodiment, no opening is provided in electrode 636, and instead, an opening providing a liquid path into the droplet operations gap is provided adjacent to electrode 636. It will also be appreciated that while the opening is shown as being generally circular, any shape is suitable. Moreover, while a single opening is shown, multiple openings may be provided. Opening 637 provides a liquid path 645 from reservoir 625 into droplet operations gap 620.

Bottom substrate 610 further includes a dielectric layer 640 atop electrodes 635 and 636. Dielectric layer 640 blocks the liquid path. Various examples of a dielectric layer are as described above with respect to aspects in which protective film 205 is a dielectric layer. A hydrophobic layer may also be provided atop dielectric layer 640. Droplet actuator 600 also includes a plunger 650, which extends into reservoir 625, and seals liquid 630 therein. Plunger 650 includes an awl 655 arranged for puncturing dielectric layer 640 to open liquid path 645, thereby permitting liquid 630 to flow through liquid path 645 and into droplet operations gap 620. As illustrated, awl 655 is inserted through an opening in plunger 650 and aligned to puncture dielectric layer 640 through opening 637.

Figure 6C:
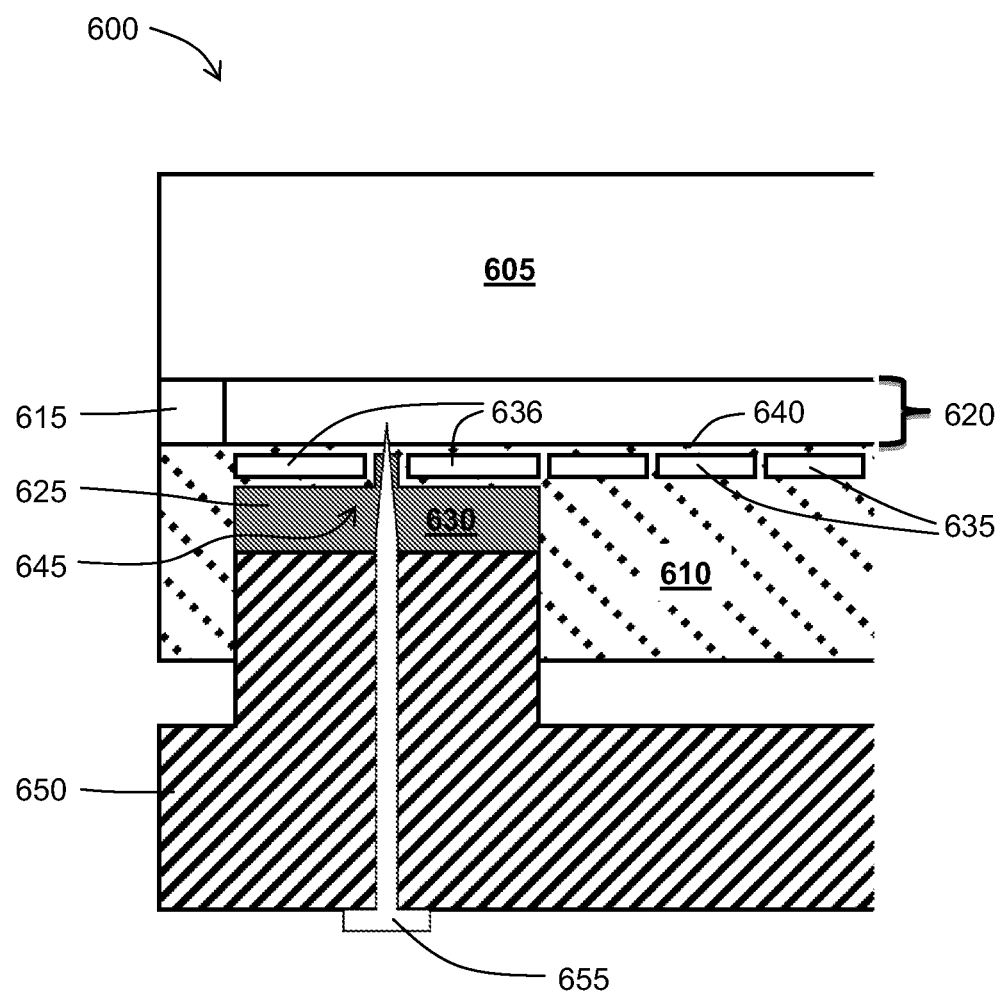

Puncturing of dielectric layer 640 is illustrated in FIG. 6C. On puncturing dielectric layer 640, plunger 650 may be forced into reservoir 625, thereby forcing liquid 630 through liquid path 645 into droplet operations gap 620.

Figure 6D:
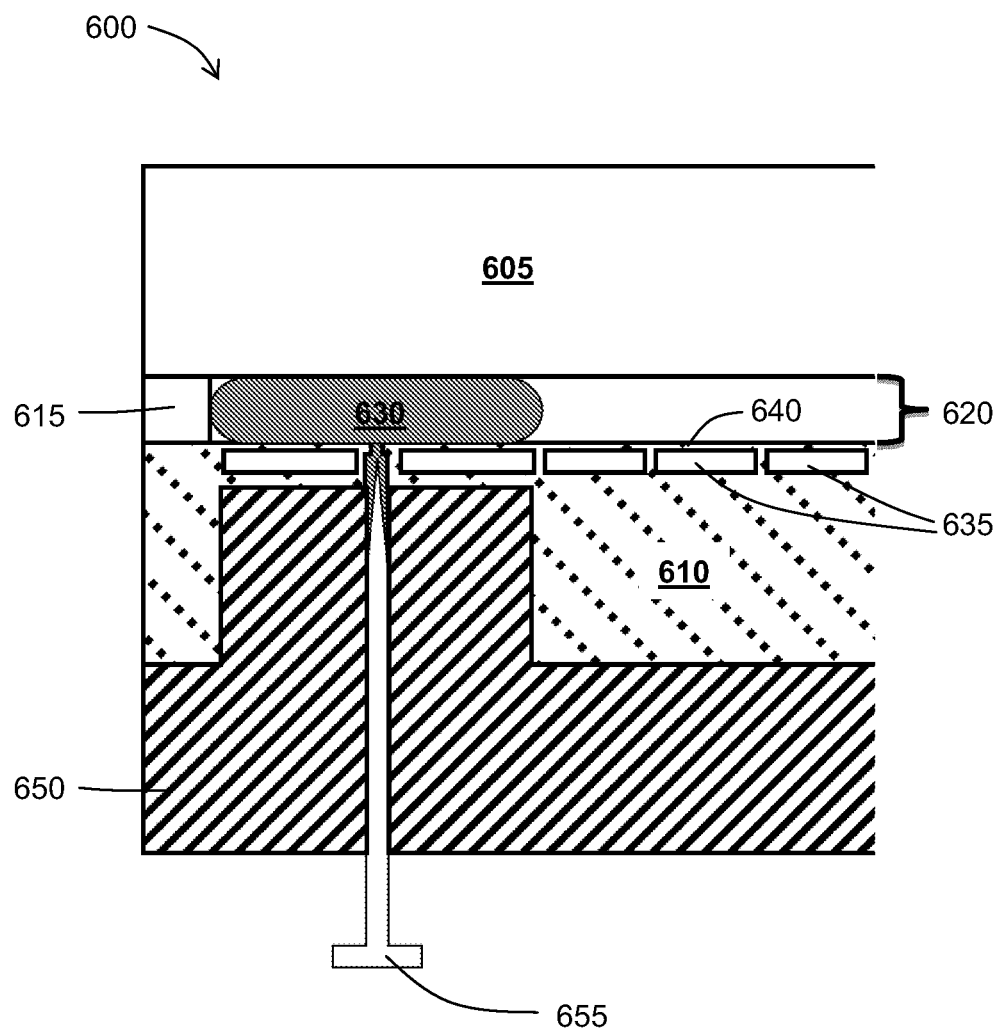

FIG. 6D illustrates plunger 650 in a fully inserted position, and shows liquid 630 situated in droplet operations gap 620 atop electrode 636. From this position, droplets may be dispensed from liquid 630 using electrodes 635 and 636. Awl 655 is shown in a retracted position in which the tip of awl 655 is removed from the punctured region of dielectric 640 in order to permit liquid to flow with reduced obstruction through liquid path 645.

Figure 6E:
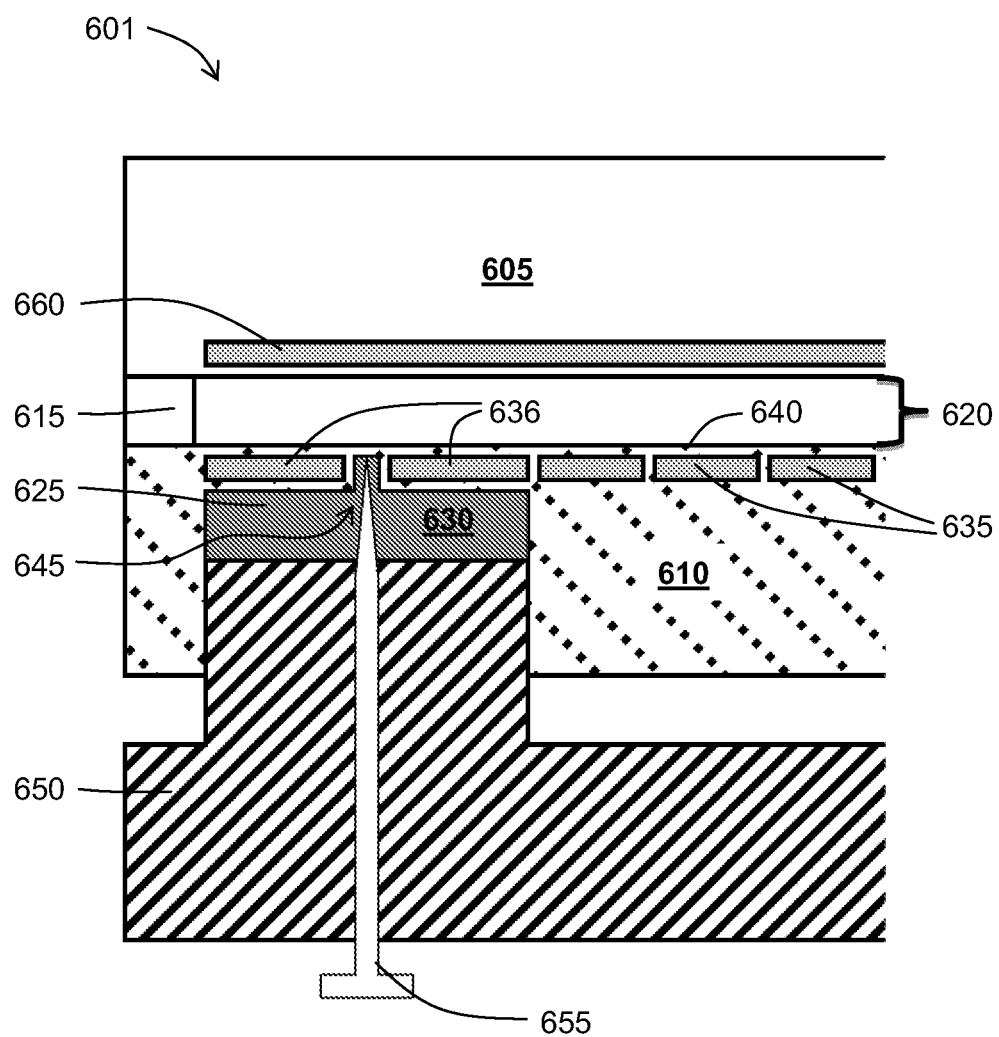

FIG. 6E shows droplet actuator 601, which is like droplet actuator 600, except that in droplet actuator 601, a single electrode 660 is provided on top substrate 605. Electrode 660 may serve as a reference electrode. In one embodiment, top substrate 605 is made from a transparent material, such as glass or plastic, while electrode 660 is also made from a transparent electrode material, such as indium tin oxide.

Figure 6F:
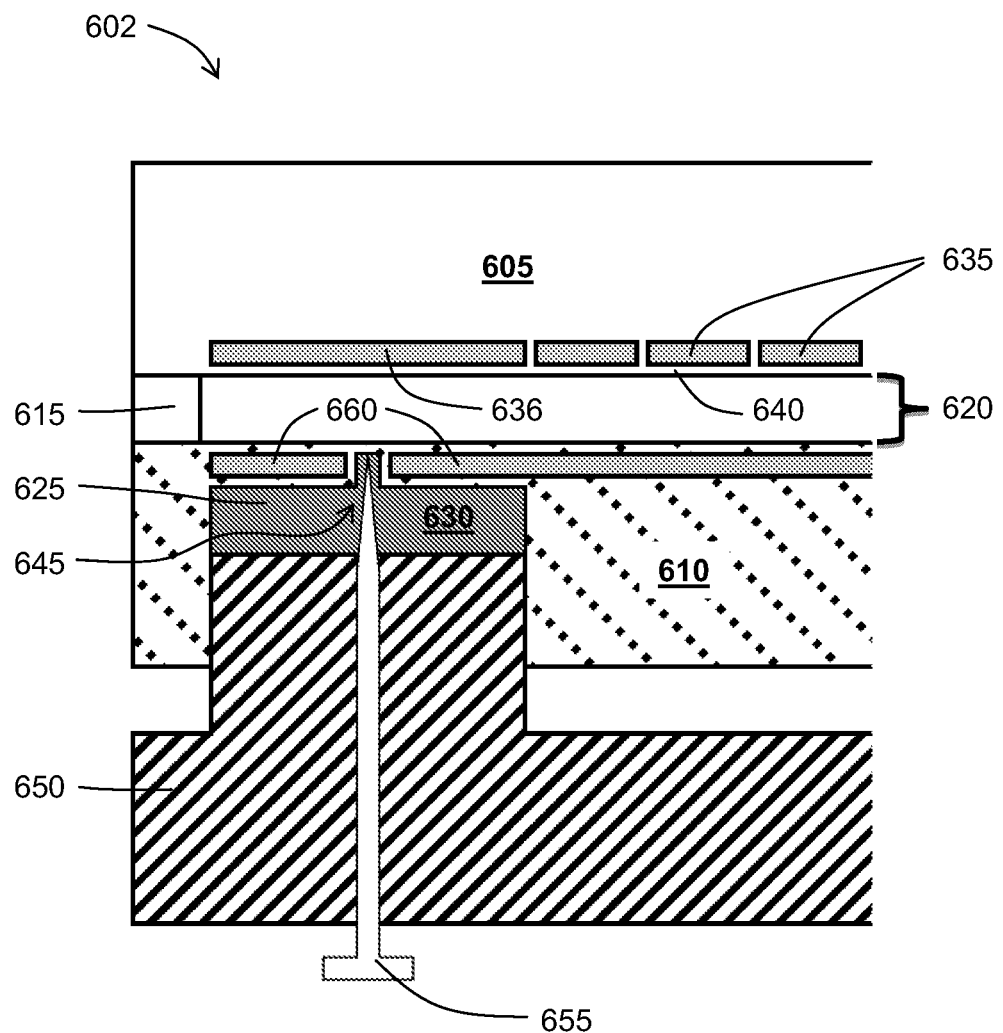

FIG. 6F shows droplet actuator 602, which is like droplet actuator 601 in FIG. 6E, except that in droplet actuator 602, a reservoir electrode 636 and droplet operations electrodes 635 are provided on top substrate 605, while ground or reference electrode 660 is provided on bottom substrate 610. Fluid 630 flows into droplet operations gap 620 through liquid path 645, which includes an opening 637 in ground electrode 660.

In other embodiments, the plunger 650 is not required and only the awl/needle 655 is utilized. As shown in FIG. 6D, plunger 650 serves as a fixed element and an integral part of bottom substrate 610 and in some cases they both may be the same element. The needle 655 in this case may be actuated during the action of loading the cartridge. The needle puncturing the dielectric 640 and part of the electrode 636 may be hydrophilic so that upon puncturing the liquid automatically is drawn onto electrode 636. In another embodiment, the needle and the reservoir arrangement could be on the top plate 605.

Figure 7:
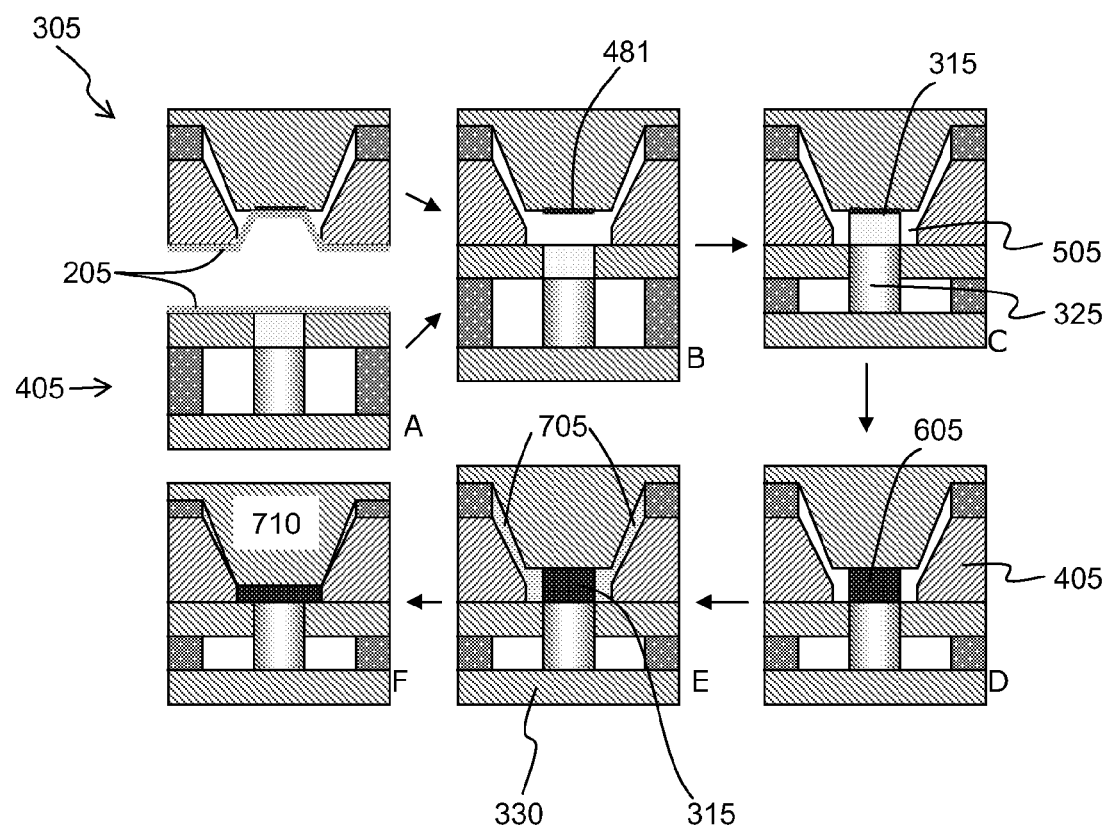
FIG. 7 illustrates an alternative embodiment of the reagent cassette of the invention including a first channel into which droplets are loaded, and a second channel for flowing liquid filler fluid around the droplets in the first channel.

FIG. 7 illustrates an alternative embodiment of the reagent cassette of the invention. In addition to the components already described, this embodiment includes a channel 705 for flowing an immiscible liquid filler fluid around droplets 315 and/or droplets 605. Further, top member includes a top plunger member 710, which may be used to agitate droplet 315 in the presence of dried reagent 481 to promote mixing. Top plunger member 710 may be associated with a sonicator arranged to vibrate top plunger member 710 and thereby promote mixing of dried reagent 481 in droplet 315.

Steps A-F illustrate the following: Step A shows top member 305 and bottom member 405 with protective film 205 in place, protecting droplets 315 and dried reagent 481. Step B shows top member 305 and bottom member 405 with protective film 205 removed, and top member 305 and bottom member 405 fitted together. Step C shows plunger 325 compressed to force droplet 315 into channel 505. Step D shows droplet 315 mixed with dried reagent 418. Step E shows filler fluid flowed through channels 705 into space in channel 505 surrounding droplets 315. Step F shows compression of plunger member 710 to compress droplet 315, e.g., to cause mixing of droplet 315.

Various embodiments may include a filler fluid reservoir in association with channel 705 and/or channel 505 for flowing oil into channel 505. In other embodiments, droplets 315 may include beads and/or dried reagents may include beads which dissolve into droplets 315. Beads may, for example, have affinity for target analytes or compounds that interfere with assay chemistry. Some embodiments may include vents from channel 705 and/or channel 505 for venting bubbles prior to loading droplets onto a droplet actuator or other microfluidic device. Protective films may be made from any material which is suitably non-reactive with reagents contacting the films. Examples include aluminum and various polymeric films. Dried reagents for use in the cassette may be prepared using methods known to one of skill in the art, such as commercial off-the-shelf (COTS) equipment and well-established procedures.

7.2 Flow Through Bead Handling and Washing Techniques

The invention also provides devices, techniques and systems for conducting flow through bead handling and washing. For example, the invention provides techniques for splitting droplets in a flow-through system, compartmentalizing beads in droplets in a flow-through system, and washing droplets in a flow-through system.

Figure 8:
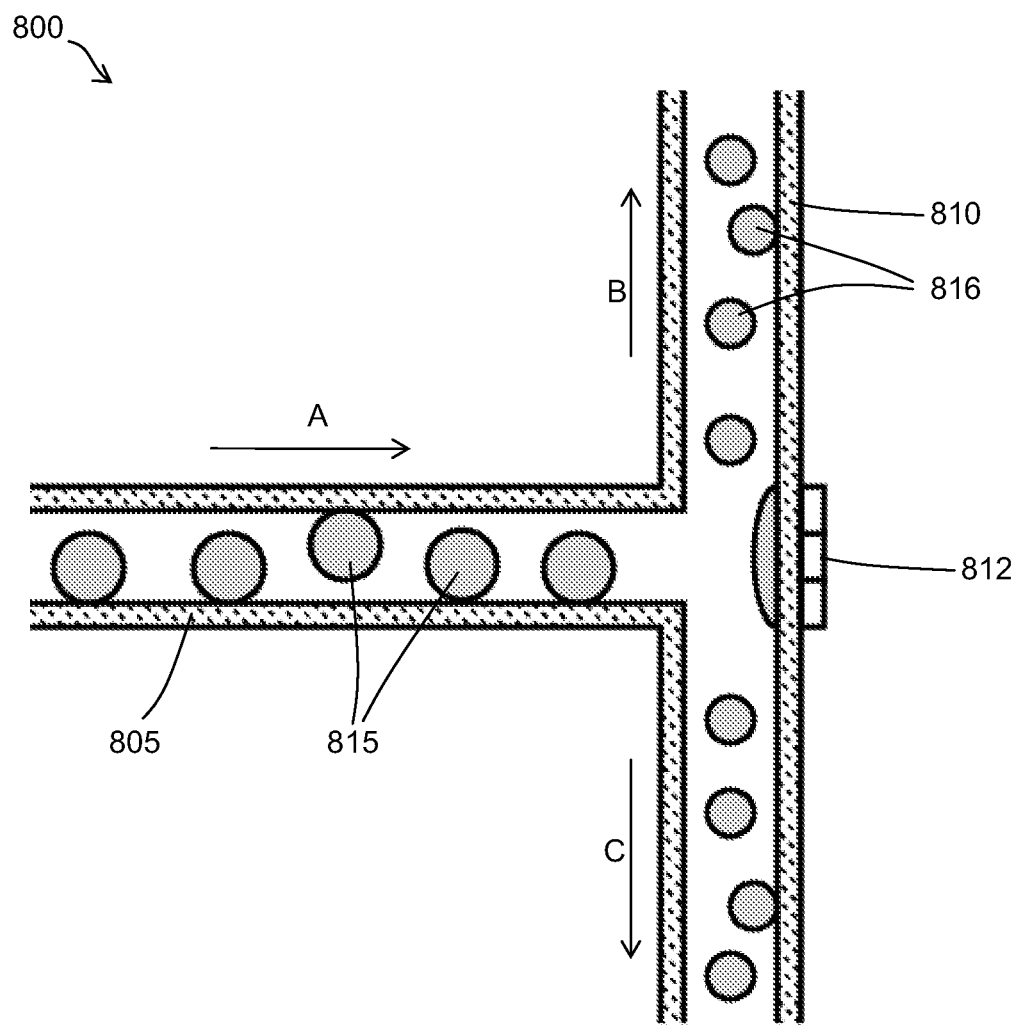
FIG. 8 illustrates a flow-through system that makes use of droplet operations for splitting droplets.

FIG. 8 illustrates a flow-through system 800 that makes use of droplet operations for splitting droplets. Flow-through system 800 includes channel 805 which intersects with channel 810. A set of electrodes 812 are associated with channel 810 at a position which is approximately opposite to an entry point of channel 805 into channel 810. The internal walls of channels 805 and 810 are hydrophobic. Channels 805 and 810 are filled with a liquid filler fluid which is substantially immiscible with parent droplets 815. Parent droplets 815 flow through channel 805 in the direction of arrow A. When electrodes 812 are activated, the internal wall of channel 810 in the region of electrodes 812 behaves in hydrophilic manner. When a parent droplet 815 impacts the electrode-associated region, the droplet spreads to conform to the shape of the activated electrodes. When an intermediate electrode is deactivated, the droplet splits into two sub-droplets 816. In the embodiment illustrated, the two sub-droplets 816 flow into channel 810 in opposite directions, as illustrated by arrows B and C. In operation, by controlling the flow of filler fluid through channels 805 and 810, droplets 815 may be sequentially contacted with electrodes 812, electrode 812 may be used to split each droplet into two sub-droplets 816, and sub-droplets 816 may be flowed into channel 810, as indicated. In an alternative embodiment, it will be appreciated that a flow may be established in channel 810 which causes sub-droplets 816 to flow in the same direction, i.e., arrows B and C may indicate a flow in a common direction, rather than opposite directions.

Figure 9:
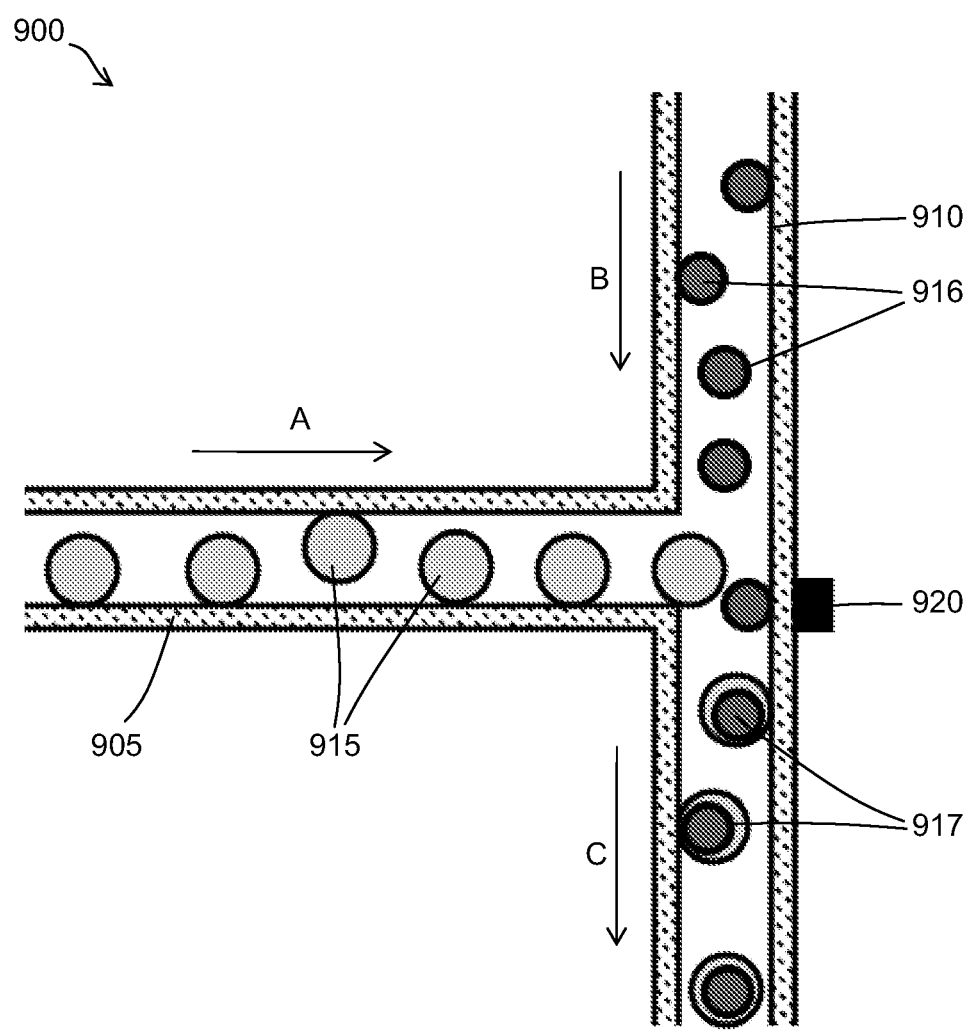
FIG. 9 illustrates a flow-through system configured for adding beads to droplets.

FIG. 9 illustrates a flow-through system 900 configured for adding beads to droplets. System 900 includes channel 905 which intersects with channel 910. A liquid filler fluid in channel 905 flows in the direction of arrow A. A liquid filler fluid in channel 910 flows in the direction of arrow B. Droplets 915 are provided in channel 905. The liquid filler fluid in channel 905 is substantially immiscible with droplets 915. Droplets 915 flow through channel 905 into channel 910 at a velocity sufficient to cause them to impact a region on the wall of channel 910. The various dimensions of channel 905, channel 910 as it enters the intersection between the two channels, and channel 910 as it exits the intersection between the two channels, as well as the angle of intersection and the velocity of filler fluid flow through the respective channels may be adjusted as needed to achieve the pre-selected droplet impact on the wall of channel 910. A magnet 920 is associated with channel 910 at a position which is approximately the point of impact of droplets 915 on the wall of channel 910. The magnet may be adjustable in order to align it with the appropriate location at which droplets 915 impact the wall of channel 910. The magnet may be an electromagnet, which may be switched on and off. The magnet may be a permanent magnet, which is movable, e.g., generally in the direction of the axis indicated by arrow A. Beads 916 are provided in the filler fluid which flows through channel 910. Beads 916 may be hydrophilic and may be provided in a hydrophobic filler fluid. As each bead comes into proximity with magnet 920, the bead is substantially immobilized on magnet 920. When a droplet 915 impacts a bead 916 immobilized on magnet 920, bead 916 is engulfed by the droplet, yielding bead containing droplet 917. The bead-containing droplet 917 may continue to flow through channel 910 in the direction of arrow C. Various techniques may be used to separate bead containing droplet 917 from the magnet 920 to permit bead containing droplet 917 to continue to flow-through channel 910. For example, the surface tension of droplet 915 may be selected to overcome the attractive force of magnet 920 on the bead, as the bead containing droplet 917 is forced through channel 910 by the flowing filler fluid. In this embodiment, it is not necessary to remove or deactivate magnet 920. In another embodiment, magnet 920 is an electromagnet, and the electromagnet is switched off to release the bead-containing droplet 917. In yet another embodiment, magnet 920 is removable, and magnet 920 is physically moved away from channel 910 in order to permit the release of bead containing droplet. The spacing of droplets 915 and beads 916 may be adjusted in order to achieve a pre-selected number of beads and each droplet. For example, several beads may be permitted to collect at magnet 920 between each droplet 915 in order to provide droplets with multiple beads. Droplets potentially containing beads may be tested downstream, and sorted to exclude any droplets which lack beads or which lack the pre-selected number of beads. Sorting may, for example, be based on optical properties and/or electrical properties of the bead-containing droplets.

Figure 10:
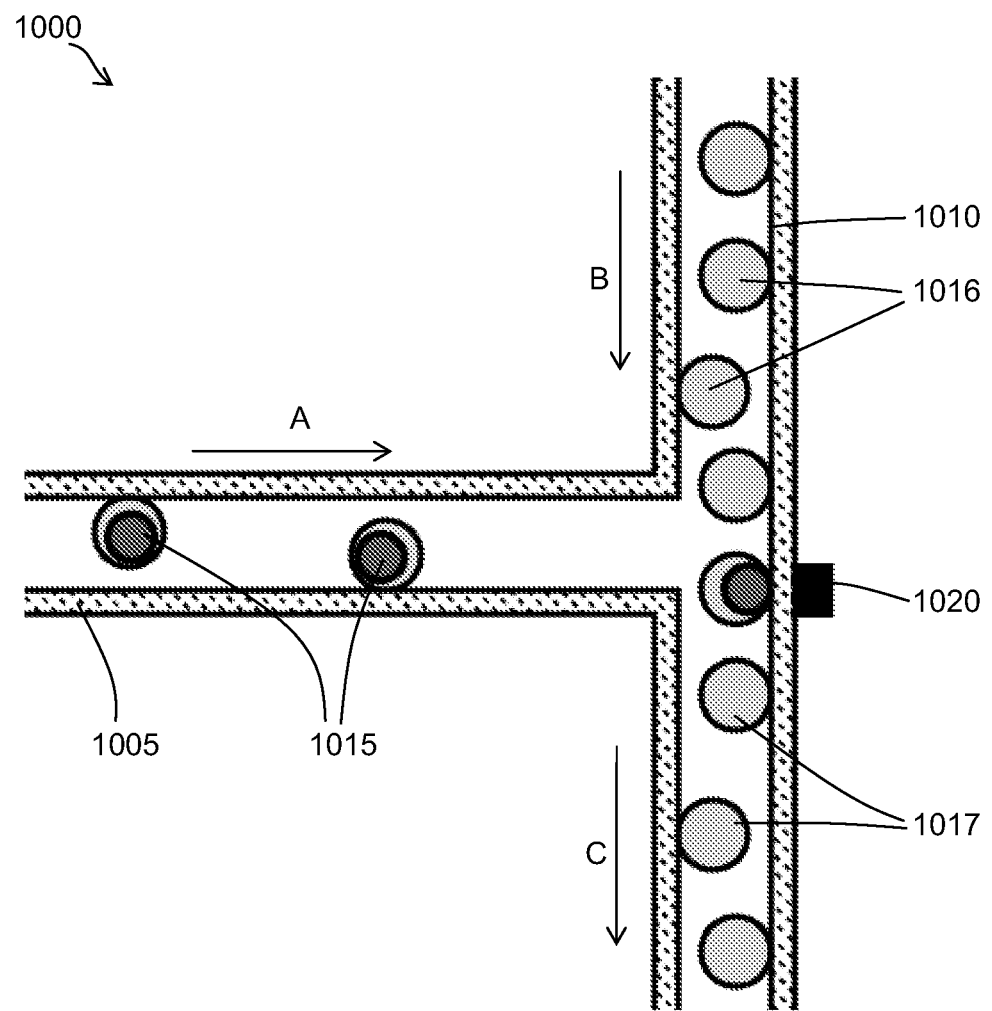
FIG. 10 illustrates a flow-through system that makes use of droplet operations to wash beads in droplets.

FIG. 10 illustrates a flow-through system 1000 which makes use of droplet operations to wash beads in droplets. Flow-through system 1000 includes channel 1005, which intersects with channel 1010. A liquid filler fluid in channel 1005 flows in the direction of arrow A. A liquid filler fluid in channel 1010 flows in the direction of arrow B. Bead-containing droplets 1015 are provided in channel 1005. Wash droplets 1016 are provided in channel 1010. Wash droplets 1016 may include a wash buffer. It will also be appreciated that in an alternative embodiment, rather than washing the beads, the method is used to concentrate one or more substances onto the beads. In such other embodiment, wash droplets 1016 may be replaced with sample droplets or other droplets including droplets including one or more target substances for which the beads have affinity. In yet another embodiment, rather than a single magnet 1020 attracting bead-containing droplet 1015 to the wall of channel 1010, one or more magnets may be provided around channel 1010 and arranged to substantially immobilized the bead within the channel, but away from the wall of the channel. The size of channel 1010 at magnet 1020 may be selected to ensure that wash droplets 1016 impact immobilized bead containing droplet 1015 as they flow past magnet 1020 or other magnet arrangement. The velocity of impact is selected to cause droplets 1016 to impact droplet 1015, merge with droplet 1015, followed by a breaking off of a new droplet 1017 moving in the direction of arrow C. In this manner, by sequentially merging the bead containing droplet with a wash droplet in and breaking off a separate droplet, the liquid surrounding the bead-containing droplet maybe be depleted of unwanted substances. Upon completion of the wash cycle, when the depletion of unwanted substances is calculated to have been achieved based on the number of wash droplets passed across the bead, the bead containing droplet may be released to continue to flow-through channel 1010. Downstream, the bead containing droplets may be separated from the used wash droplets 1017. Thus, the invention provides a technique for washing beads in a flow-through operation, wherein a bead containing droplet is immobilized using a magnet, and one of more wash droplets are caused to impact and merge with the bead-containing droplet, and wherein the filler fluid flowing through the channel is at a velocity sufficient to cause one or more droplets to break off of the combined droplet, thereby leaving a bead containing droplet with a reduced amount of one or more substances relative to the starting bead-containing droplet. Similarly, the invention provides a technique for concentrating a substance on beads in a flow-through operation, wherein a bead containing droplet is immobilized using a magnet in a channel, and one of more droplets including a target substance are caused to impact and merge with the immobilized bead-containing droplet, thereby causing a bead in the bead-containing droplet having affinity for the target substance to concentrate target substance thereon. As with the washing operation, the filler fluid flowing through the channel may cause one or more droplets to break off of the combined droplet, thereby leaving a bead containing droplet with an increased amount of one or more substances concentrated on the bead relative to the starting bead-containing droplet.

The various sizes of channels 1005 and 1010, as well as the angle of intersection between the two channels, may be adjusted in order to improve efficiency of the washing operation. Multiple beads may also be present in droplets 1015. The ratio of spacing and velocity of bead containing droplets 1015 flowing through channel 1005 relative to the spacing and velocity of wash droplets or sample droplets flowing through channel 1010 may be adjusted to achieve the pre-selected effect. In yet another embodiment, channel 1010 may include a series of sample droplets for concentrating sample onto the immobilized bead, followed by a series of wash droplets for washing the immobilized bead. In an alternative embodiment, the splitting off of wash droplets following merging of the wash droplets with the immobilized beat-containing droplet may be facilitated by droplet operations mediated by electrodes, e.g. as described above with reference to FIG. 8.

In the various flow-through embodiments described herein, it is possible for droplets to be sorted to select out a pre-selected subset of droplets from the overall droplet population. For example, droplets may be sorted as described in Link et al., US Patent Publication No. 20080014518, entitled "Microfluidic Devices and Methods of Use Thereof," published on Jan. 17, 2008, the entire disclosure of which is incorporated herein by reference for its teaching concerning sorting of droplets in microfluidic devices. Further, once droplets of interest are isolated, the droplets may be flowed onto a droplet actuator of the invention for further analysis. For example, a subset of droplets of interest from a flow-through droplet sorting operation may be flowed into a droplet operations gap of a droplet actuator where they are subject to droplet operations mediated by electrodes. Similarly, a subset of droplets of interest from a flow-through droplet sorting operation may be flowed into a reservoir of the droplet actuator, which reservoir is coupled by a liquid path to a droplet operations gap of a droplet actuator, such that the droplets of interest may be transported from the reservoir into the droplet operations gap where they may be subject to droplet operations mediated by electrodes. In one embodiment, multiple droplets of interest are pooled together in a reservoir of a droplet actuator prior to being subjected to droplet operations in a droplet operations gap of the droplet actuator.

7.3 Techniques Using Viscous, Solid, or Semi-Solid Samples

The invention provides droplet actuator devices, techniques and systems for making and using droplet actuators to process viscous, solid or semi-solid samples. For example, the invention provides a technique for processing viscous, semisolid, and/or solid samples. Target substances of interest are extracted from the viscous, solid or semi-solid sample, and then processed using standard droplet operations.

Figure 11A:
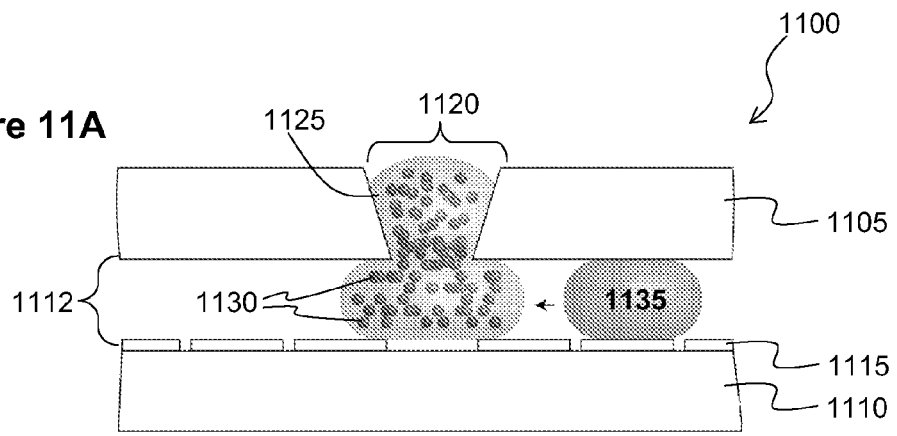
FIGS. 11A, 11B, and 11C illustrate a section of a droplet actuator and a method of processing a viscous, solid or semi-solid sample on a droplet actuator.
Figure 11B:
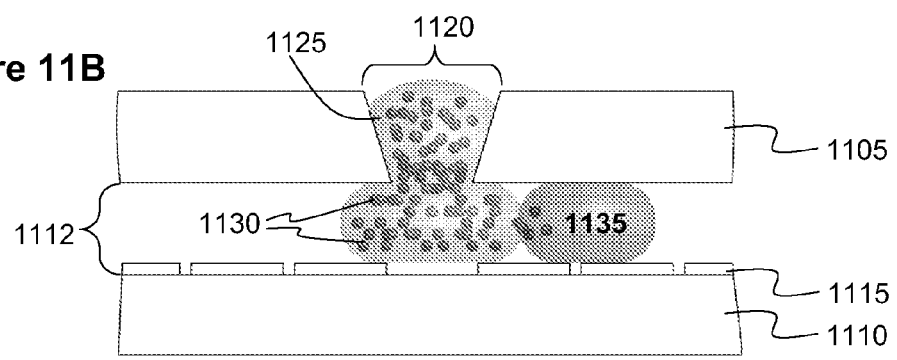
Figure 11C:
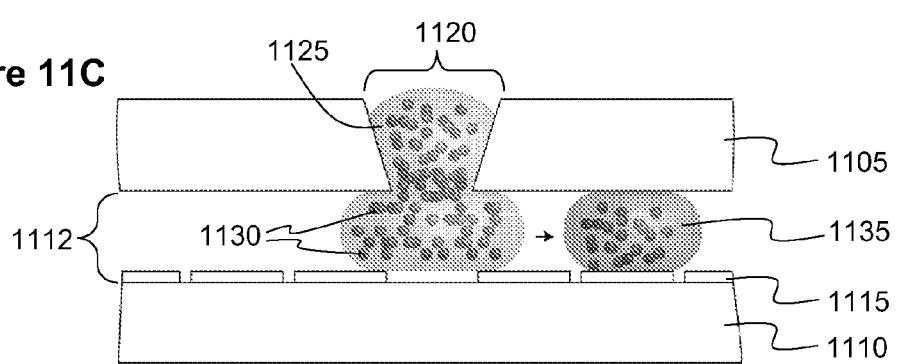

FIGS. 11A, 11B, and 11C illustrate a section of a droplet actuator 1100 and a method of processing a viscous, solid or semi-solid sample on a droplet actuator. Droplet actuator 1100 includes a top substrate 1105 and a bottom substrate 1110 separated by droplet operations gap 1112. In certain embodiments, top substrate 1105 may be omitted. Droplet operations electrodes 1115 (e.g., electrowetting electrodes) and reference electrodes (not shown) are associated with top substrate 1105 and/or bottom substrate 1110. Droplet operations electrodes 1115 are configured for conducting one or more droplet operations in droplet operations gap 1112. Top substrate 1105 includes an opening 1120 therein for loading sample 1125 into droplet operations gap 1112. Sample 1125 includes one or more target substances 1130. As illustrated in FIG. 11A, droplet 1135 is positioned in droplet operations gap 1112 atop one or more droplet operations electrodes 1115. FIG. 11B shows droplet 1135 being transported into contact with sample 1125, such that one or more target substances 1130 is dissolved into droplet 1135. Transport of droplet 1135 may be effected using one or more droplet operations. For example, in one embodiment, transport is effected by sequentially activating/deactivating electrodes 1115. Droplet 1135 may be transported away from sample 1125 via droplet operations as shown in 11C. Droplet 1135 that potentially included one or more target substances may be used as input for conducting one or more assays to identify and/or quantify one or more target substances 1130. In one embodiment, sample 1125 is sufficiently viscous, semi-solid, or solid in order to permit droplet 1135 to contact sample 1125 and be transported away from sample 1125 without being substantially mixed with sample 1125.

FIGS. 11A, 11B, and 11C illustrate a general principle in which a micro or nano liquid is transported into contact with a viscous or solid sample for collection of a target substance and then transported away. As illustrated, using one or more droplet operations, droplet 1135 contacts sample 1125, which brings droplet 1135 into lateral contact with sample 1125. However, it will be appreciated that sample 1125 may be positioned at any angle relative to droplet 1135, e.g., above or below droplet 1135. For example, sample 1125 may project only slightly into droplet operations gap 1112, in which case, droplet 1135 may be transported along a path of electrodes underneath sample 1125. In this example, contact is between the top of droplet 1135 and the bottom of sample 1125. Alternatively, sample 1125 may be exposed to droplet operations gap 1112 and droplet 1135 via an opening (not shown) in bottom substrate 1110.

The methods of the invention are particularly suitable for tests involving viscous, solid or semi-solid samples. Samples may, for example, be environmental samples, process samples, or biological samples. Examples of suitable samples include sputum, coagulated blood, animal tissue samples, plant tissue samples, soil samples, rock samples, and the like. In some cases, samples are sufficiently viscous, semi-solid or solid to permit a droplet to contact the sample and be transported away from the sample without being substantially mixed with the sample. Further, the sample may include foreign matter, such as a matrix (e.g., a swab) used to collect the sample. For example, when a droplet of sputum is loaded, it may not be readily transportable using droplet operations then a droplet that lyses sputum can be brought in contact with sputum. After incubation and preferably some agitation of the lysis droplet, the sputum will be liquefied rendering it to be transportable using droplet operations.

Droplet 1135 may be aqueous or non-aqueous. In one embodiment, droplet 1135 is an aqueous buffer established at a pH which is suitable for dissolving sample 1125. Droplet 1135 may also include one or more reagents. The chemical characteristics of droplet 1135 may be adjusted to render droplet 1135 suitable for acquiring one or more target substances 1130. In one example, droplet 1135 includes a lysis buffer solution. A lysis buffer solution is used to lyse cells for use in assays involving target substances, which are sub-components of the cells. In some embodiments, droplet 1135 includes one or more beads, e.g., magnetically responsive or non-magnetically responsive beads. Examples of suitable magnetically responsive beads are described in U.S. Pat. No. 7,205,160, entitled "Multiplex flow assays preferably with magnetic particles as solid phase," granted on Apr. 17, 2007. The beads may have an affinity for one or more target substances or contaminants. For example, the beads may have affinity for target cells, protein, DNA, and/or antigens. In one example, the beads may have an affinity for one or more target substances 1130 from the sample 1125 of interest.

Examples of droplet actuator techniques for immobilizing magnetic beads and/or non-magnetic beads are described in the foregoing international patent applications and in Sista, et al., U.S. Patent Application Nos. 60/900,653, entitled "Immobilization of Magnetically-responsive Beads During Droplet Operations," filed on Feb. 9, 2007; Sista et al., U.S. Patent Application No. 60/969,736, entitled "Droplet Actuator Assay Improvements," filed on Sep. 4, 2007; and Allen et al., U.S. Patent Application No. 60/957,717, entitled "Bead Washing Using Physical Barriers," filed on Aug. 24, 2007; the entire disclosures of which are incorporated herein by reference.

7.4 Gel Electrophoresis Techniques

The invention provides droplet actuator devices including a gel for use in gel electrophoresis, along with techniques and systems for conducting gel electrophoresis on a droplet actuator. The gel electrophoresis techniques of the invention are useful for separating substances present in a droplet on a droplet actuator. For example, the invention is useful for separating complex biomolecules (e.g., proteins and/or nucleic acids) using an electric current applied to a gel matrix on a droplet actuator. The gel matrix may, for example, be a cross-linked polymer whose composition and porosity are selected based on the specific weight (e.g., molecular weight) and composition of the substances being analyzed. In one embodiment, the gel may be composed of different concentrations of acrylamide and a cross-linker to produce different-sized mesh networks of polyacrylamide. Polyacrylamide may be used to separate and analyze proteins or small nucleic acids (e.g., DNA, RNA, or oligonucleotides). In another embodiment, the gel may be composed of a purified agarose matrix. Agarose gels may be used to separate larger nucleic acids and/or complex biomolecules.

The methods of the invention make use of gel electrophoresis on a droplet actuator for analytical purposes (e.g., separation and quantitation of a specific target(s)). In another embodiment, gel electrophoresis may be used as a preparative technique (e.g., for isolation of a specific target(s)) prior to use of other assay techniques for further characterization of a substance. Other assay techniques may, for example, include PCR, cloning, nucleic acid sequencing, immunoassays, enzymatic assays, exposure to sensors, etc. In another embodiment, a "capture" droplet may be used to capture a target droplet as it elutes off the gel slug as a fraction collector, e.g. using the techniques described with reference to FIG. 11.

Figure 12A:
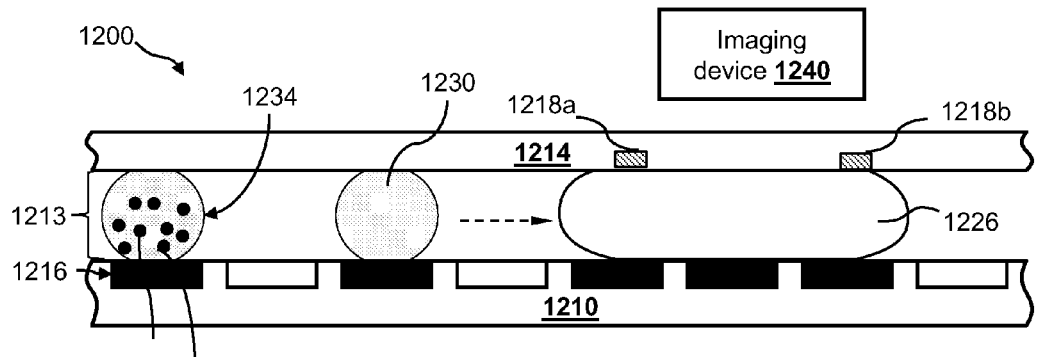
FIGS. 12A, 12B, and 12C illustrate a section of a droplet actuator and a process of separating and analyzing a sample using gel electrophoresis.
Figure 12B:
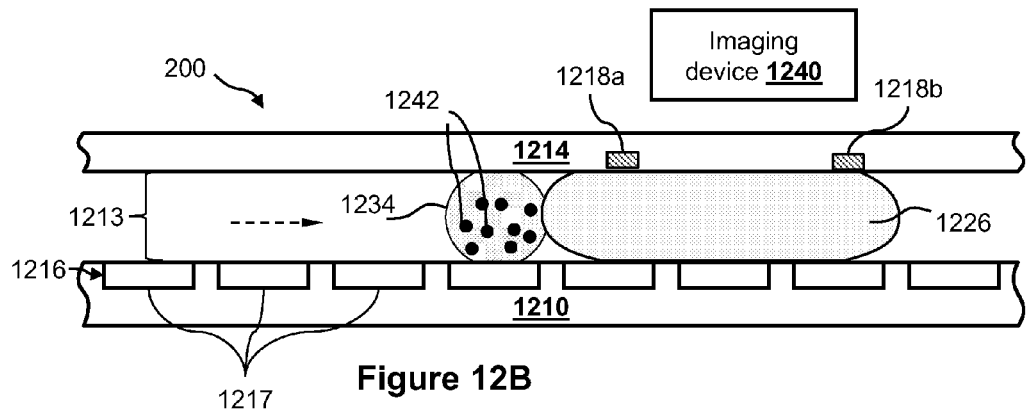
Figure 12C:
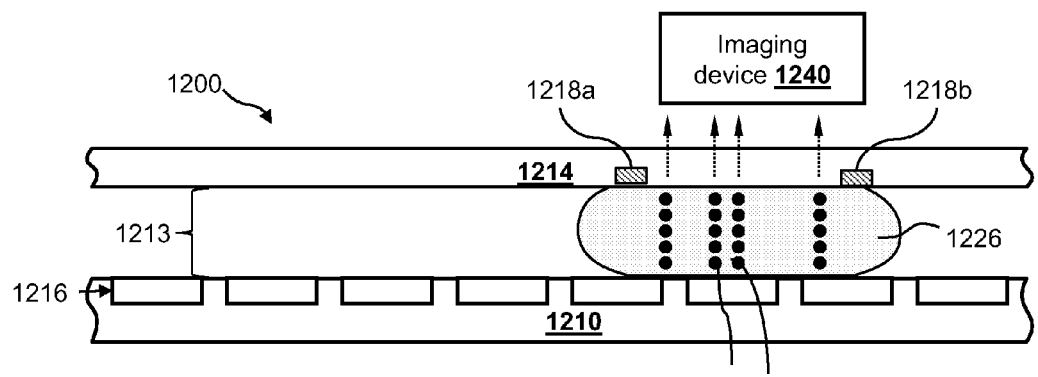

FIGS. 12A, 12B, and 12C illustrate a section of droplet actuator 1200 and a process of separating and analyzing a sample using gel electrophoresis. Droplet actuator 1200 may include bottom substrate 1210 separated from top substrate 1214 by droplet operations gap 1213. Path 1216 of droplet operations electrodes 1217 is arranged on bottom substrate 1210; however, it will be appreciated that droplet operations electrodes and/or ground electrodes may be associated with top substrate 1214 and/or bottom substrate 1210. Droplet operations electrodes 1217 may, for example, be electrowetting electrodes. Electrophoresis electrodes 1218a and 1218b, are arranged on top substrate 1214, but may be on either or both substrates. One of electrodes 1218a and 1218b may be a negative electrode, while the other may be a positive electrode.

Droplet operations gap 1213 may be provided with one or more gel droplets 1226 and one or more catalyst droplets 1230, although in some cases neither a catalyst nor a catalyst droplet are required. In some cases, the catalyst may just be photoinitiation. Gel droplets 1226 may typically be from about 1× to about 5× or larger droplets. A 3× droplet, for example, has a footprint that is approximately 3 times the area of one droplet operations electrode 1217. Gel droplet 1226 may, for example, include reagents suitable for forming a polyacrylamide gel, such as acrylamide, bis-acrylamide, and buffer. Gel droplet 1226 remains in a liquid form until polymerization of the acrylamide is initiated by the addition of a catalyst. Catalyst droplet 1230 contains the chemical reagents required to accelerate polymerization of gel droplet 1226. For example, catalyst droplet 1230 may include N,N,N,N-Tetramethyl-Ethylenediamine (TEMED) and ammonium persulfate to accelerate polymerization of the acrylamide in gel droplet 1226.

Droplet operations gap 1213 may be provided with one or more sample droplets, e.g., sample droplet 1234. Sample droplet 1234 includes one or more target substances 1242 to be evaluated. Target substances 1242 may, for example, be fluorescently labeled proteins or nucleic acids. To evaluate target substances 1242, an imaging device 1240 is associated with droplet actuator 1200. Imaging device 1240 may be used to capture digital images of substances separated in gel droplet 1226, such as labeled proteins or nucleic acids. In some cases, imaging device 1240 may capture images through top substrate 1214, which may be, for example, a glass or a plastic plate that is substantially transparent.

FIG. 12A shows a first step in which droplet operations may be executed in order to form a gel for conducting gel electrophoresis on droplet actuator 1200. Activated electrodes are shown in black. Using one or more droplet operations, gel droplet 1226 may be elongated along several droplet operations electrodes in contact with electrophoresis electrodes 1218a and 1218b. Catalyst droplet 1230 may be transported using one or more droplet operations into contact with gel droplet 1226. Catalyst droplet 1230 and gel droplet 1226 merge, initiating polymerization in gel droplet 1226 to form the gel matrix for electrophoresis. FIG. 12B shows a second step in which sample droplet 1234 is transported into contact with the polymerized gel droplet 1226. FIG. 12C shows a third step in which an electrical potential (e.g., about 40 to about 100 volts) may be applied to gel droplet 1226 via electrophoresis electrodes 1218a and 1218b. In some cases, electrode 1218a might directly contact droplet 1234. The electrical current causes target substances 1242 in sample droplet 1234 to electrophorese into and through gel droplet 1226. Separation of target substances 1242 in gel droplet 1226 is typically determined by charge such that different molecules will move at different rates. As an example, target substances 1242 may be negatively charged (e.g., nucleic acids) and migrate from electrophoresis electrode 1218a (i.e., negative electrode) toward electrophoresis electrode 1218b (i.e., positive electrode). Imaging device 1240 may be used to capture an image of separated target substances 1242 in gel droplet 1226 and/or as they elute off the end of gel droplet 1226. The captured image may be used to identify and/or quantitate different target substances 1242 in sample 1234.

It will be appreciated that the method of the invention also provides a generic method of forming a polymerized structure in a droplet operations gap of a droplet actuator. The method may include using one or more droplet operations to form a first droplet into a pre-selected shape, and to contact the first droplet with a second droplet to cause polymerization of the combined droplets. One of the first droplet and/or second droplet may be a polymer droplet, while the other of the first droplet and/or second droplet may be a catalyst droplet. In addition to use for forming gels for electrophoresis, the method may be used to provide a physical obstacle on a droplet actuator. The physical obstacle may, for example, be useful for sealing off a region of the droplet actuator. In one embodiment a droplet actuator is provided that includes a barrier in the droplet operations gap establishing two regions on the droplet actuator. An opening is provided in the barrier, and electrodes are arranged for transporting droplets through the opening. When it is desirable to close the opening, a polymer droplet is polymerized in the opening. For example, a polymer droplet may be transported into the opening. A catalyst droplet may be combined with the polymer droplet in the opening. Upon polymerization, the opening may be substantially closed.

7.5 Fluidics System for Loading Droplet Actuator

The invention provides a fluidics system and technique for using the system for loading liquids onto a droplet actuator. The invention also provides droplet actuators loaded using the fluidics system and method of the invention and methods of using such droplet actuators to conduct droplet operations. In some embodiments, the loading provides a droplet actuator in which the droplet operations gap or a reagent storage channel is fully filled with filler fluid and reagents that is substantially lacking in air bubbles.

FIG. 13A-13I are schematic diagrams of fluidics system 1300 for loading liquid receptacle, such as a channel or droplet operations gap of a droplet actuator, with liquid. Fluidics system 1300 may include an arrangement of one or more valves, one or more pumps, one or more capillaries, and one or more liquid supply vessels; all fluidly connected. Additionally, a droplet actuator may be fluidly connected to fluidics system 1300, such that liquid may be flowed from fluidics system 1300 into a liquid receptacle of droplet actuator 1320.

Fluidics system 1300 includes a plurality of valves, illustrated here as pinch valves (PV): PV1, PV2, PV3, PV4, and PV5. A pinch valve is a valve in which a flexible tube is pinched between one or two moving external elements in order to stop the flow through the tube.

Figure 13A:
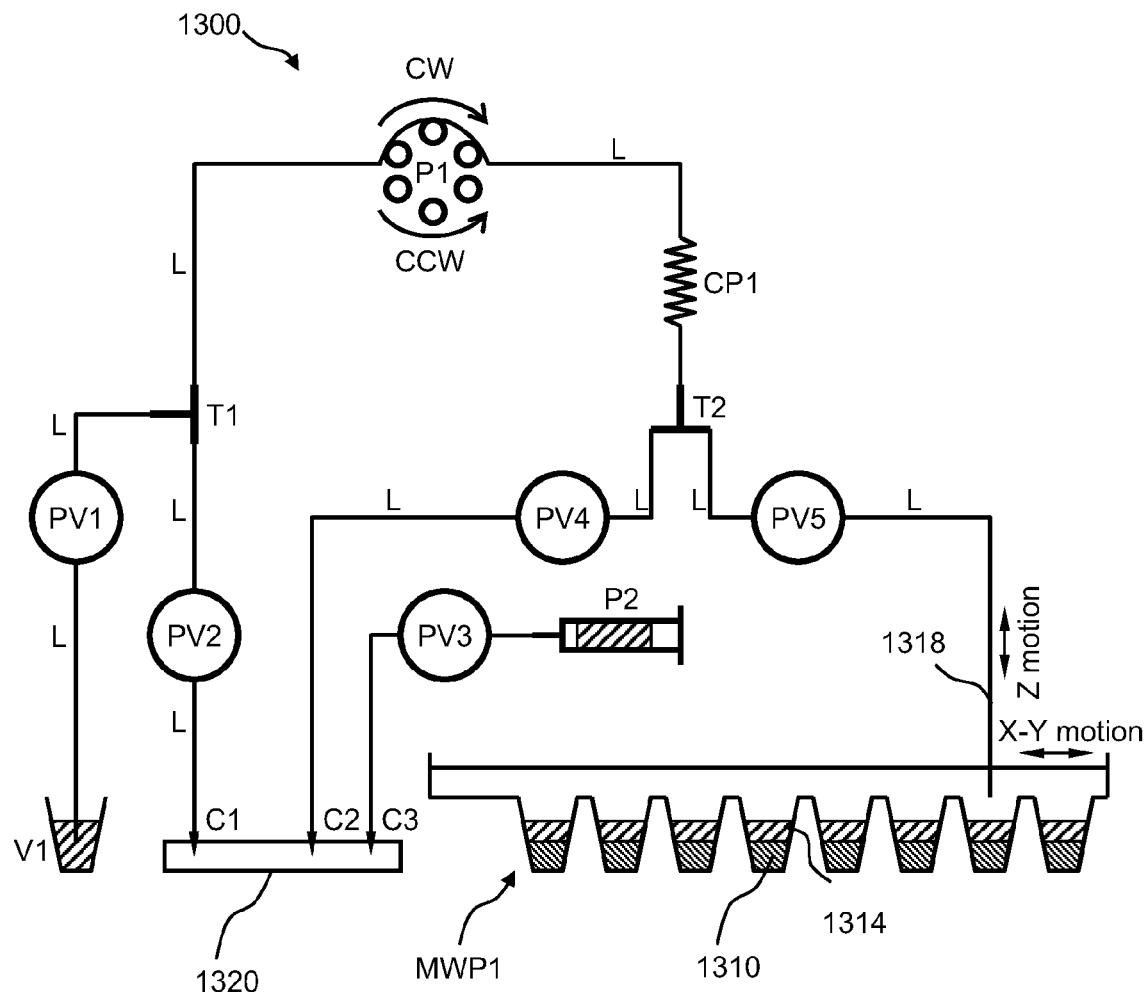
FIGS. 13A, 13B, 13C, 13D, 13E, 13F, 13G, 13H, and 13I are schematic diagrams of fluidics system for loading liquid receptacle, such as a channel or droplet operations gap of a droplet actuator, with liquid.

Fluidics system 1300 includes one or more pumps, illustrated here as peristaltic pump P1. In a peristaltic pump, liquid is contained within a flexible tube fitted inside a circular pump casing. A rotor with one or more of rollers, shoes, or wipers that are attached to the external circumference compresses the flexible tube. As the rotor turns, the part of tube under compression closes, which forces the liquid to be pumped to move through the tube. Referring to FIG. 13A, peristaltic pump P1 may controlled to operate in a clockwise (CW) and counter clockwise (CCW) direction. The peristaltic pump may be replaced with any suitable pump type, such as gear pumps, progressing cavity pumps, roots-type pumps, reciprocating-type pumps, double-diaphragm pumps, peristaltic pumps, kinetic pumps, centrifugal pumps, eductor-jet pumps, etc.

Fluidics system 1300 also includes a pump, such as syringe pump P2. Syringe pump includes a cylinder that holds a quantity of liquid, such as filler fluid (e.g., silicone oil), which is expelled by a piston. The piston may be advanced or retracted by a motor (not shown) connected thereto, in order to provide smooth pulseless flow.

Fluidics system 1300 includes a liquid supply vessel V1, which is, for example, any vessel for holding a quantity of liquid, such as filler fluid (e.g., silicone oil).

Fluidics system 1300 includes another liquid supply, illustrated here as a multi-well plate (MWP). MWP1 contains, for example, multiple reservoirs including reagents 1310 (and/or sample) under a layer of filler fluid 1314 (e.g., silicone oil). A mechanically or robotically controlled supply line 1318 may be manipulated in the X, Y, and Z directions in order to access a certain one of the multiple fluids that are contained in MWP1. In an alternative embodiment, multiple supply lines may be provided extending into the MWP1 reservoirs from the top, or through an opening in the reservoirs, such as opening in the bottom of the reservoirs.

Fluidics system 1300 includes a capillary CP1, which is a small diameter tube of any pre-selected length, depending on the pre-selected quantity of liquid to be contained therein. Various liquid lines L fluidly connect the parts of the invention.

Fluidics system 1300 may include droplet actuator 1320, which is the droplet actuator to be loaded by fluidics system 1300. Droplet actuator 1320 is fluidly connected to fluidics system 1300 via one or more liquid input/output ports. The ports provide a fluid path from an exterior of the droplet actuator into a droplet operations gap of the droplet actuator or into another reservoir in the droplet actuator, such as a channel reservoir. In one example, the droplet operations gap of droplet actuator 1320 is fluidly connected to fluidics system 1300 via ports C1, C2, and C3. In some cases, the ports may provide access to one or more channels within droplet actuator 1320, and the one or more channels are used to supply filler fluids and/or reagents into a droplet operations gap of droplet actuator 1320.

Referring again to FIG. 13A, the elements of fluidics system 1300 are fluidly connected as follows. A liquid line L fluidly connects vessel V1 to one opening of valve PV1. A liquid line L fluidly connects to the opposite opening of valve PV1 to an opening of T-connection T1. A liquid line L fluidly connects a first branch of T1 to an opening of valve PV2. A liquid line L fluidly connects the opposite opening of valve PV2 to port C1 of droplet actuator 1320. A liquid line L fluidly connects a second branch of T1 to one opening of peristaltic pump P1. A liquid line L fluidly connects to the opposite opening of peristaltic pump P1 to one opening of capillary CP1. A liquid line L fluidly connects the opposite opening of capillary CP1 to a T-connection, T2. A liquid line L fluidly connects a first branch of T2 to one opening of valve PV4. A liquid line L fluidly connects the opposite opening of valve PV4 to port C2 of droplet actuator 1320. A liquid line L fluidly connects a second branch of T2 to one opening of valve PV5. A liquid line L fluidly connects the opposite opening of valve PV5 to supply line 1318 that fluidly connects to MWP1. An input/output port of syringe pump P2 fluidly connects to port C3 of droplet actuator 1320 through valve PV3. Note that all liquid lines of fluidics system 1300 may be capillaries and that capillary CP1 may be formed of an extended length of capillary that couples peristaltic pump P1 and junction T2.

Fluidics system 1300 of FIG. 13A is exemplary only, other system variations are possible. For example, syringe pump P2 may be replaced with other types of pumps. Alternatively, fluidics system 1300 may include a single pump only. An exemplary method of purging air from fluidics system 1300 and droplet actuator 1320 and filling fluidics system 1300 and droplet actuator 1320 with substantially bubble-free liquid is described with reference to FIGS. 13B-13I.

Purging Fluidics System—Step 1

Figure 13B:
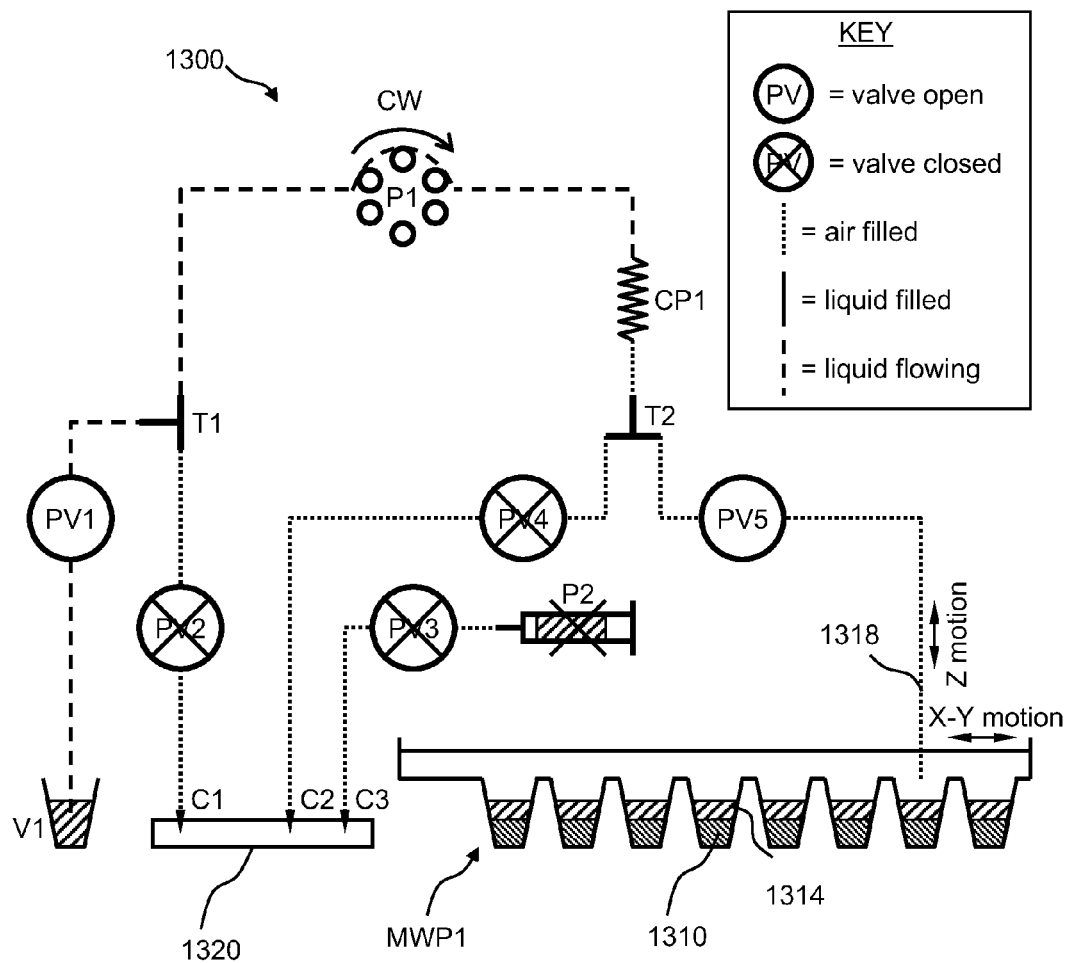

FIG. 13B, with reference to Table 1 below, illustrates a purging step in which valves PV1 and PV5 are open, valves PV2, PV3, and PV4 are closed, peristaltic pump P1 is activated in the CW direction, and syringe pump P2 is stopped. This arrangement establishes a flow of liquid from vessel V1, through valve PV1, through peristaltic pump P1, and into capillary CP1. Liquid displaces air in the path from vessel V1 to capillary CP1. Air is vented through valve PV5 to supply line 1318. Upon completion of this step, a quantity of liquid from vessel V1 that is sufficient to fill the liquid line between T1 and port C1 of droplet actuator 1320 is contained in capillary CP1.

TABLE 1

| PV1 | PV2 | PV3 | PV4 | PV5 | P1 | P2 |
|---|---|---|---|---|---|---|
| OPEN | CLOSED | CLOSED | CLOSED | OPEN | CW | STOP |

Purging Fluidics System—Step 2

Figure 13C:
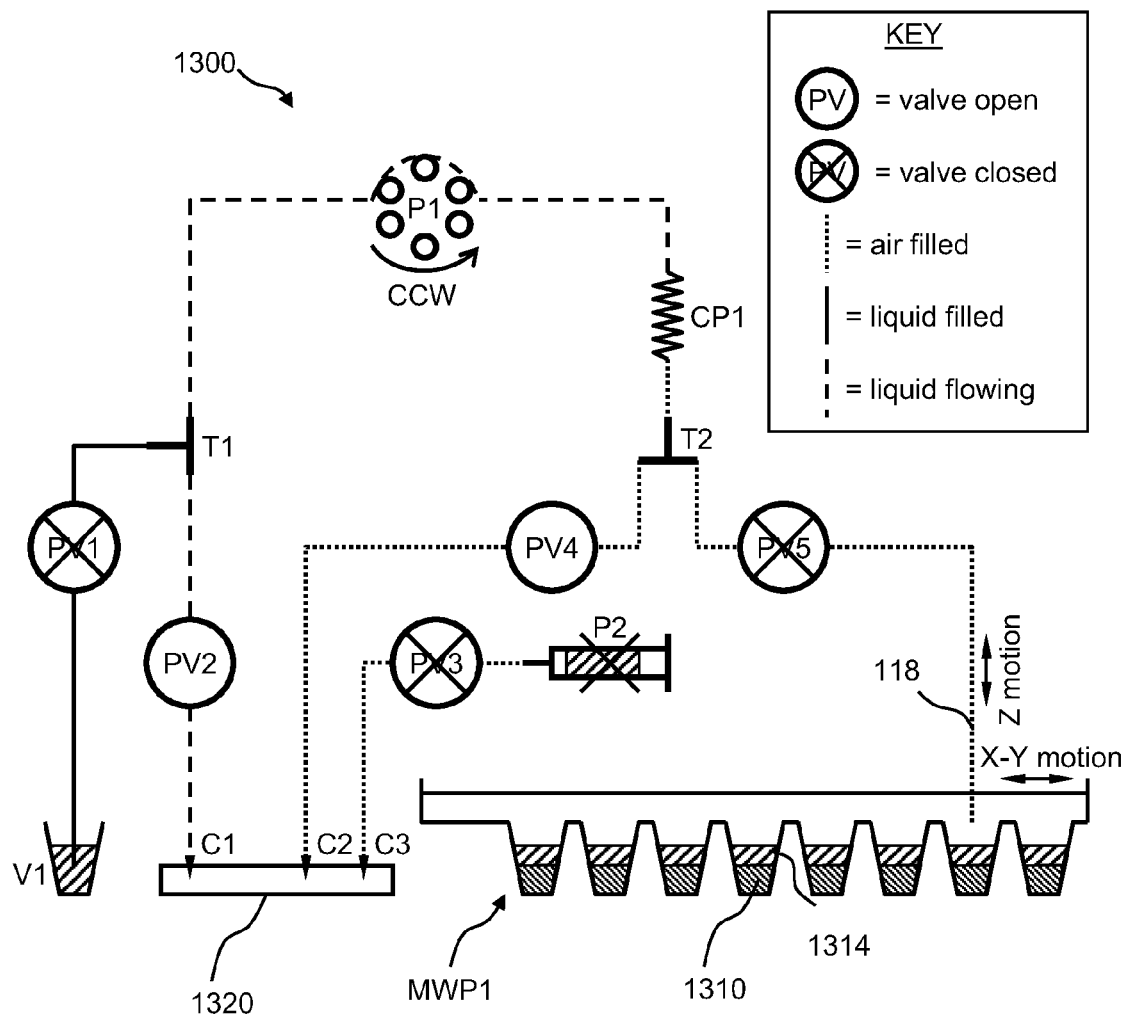

FIG. 13C, with reference to Table 2 below, illustrates a second purging step in which valves PV2 and PV4 are open, valves PV1, PV3, and PV5 are closed, peristaltic pump P1 is activated in the CCW direction, and syringe pump P2 is stopped. This arrangement establishes a flow of liquid from capillary CP1, through peristaltic pump P1, through valve PV2, and into port C1 of droplet actuator 1320. Liquid displaces air in the path from T1 to port C1 of droplet actuator 1320. Air is vented through port C2 of droplet actuator 1320 and through valve PV4.

TABLE 2

| PV1 | PV2 | PV3 | PV4 | PV5 | P1 | P2 |
|---|---|---|---|---|---|---|
| CLOSED | OPEN | CLOSED | OPEN | CLOSED | CCW | STOP |

Purging Fluidics System—Step 3

Figure 13D:
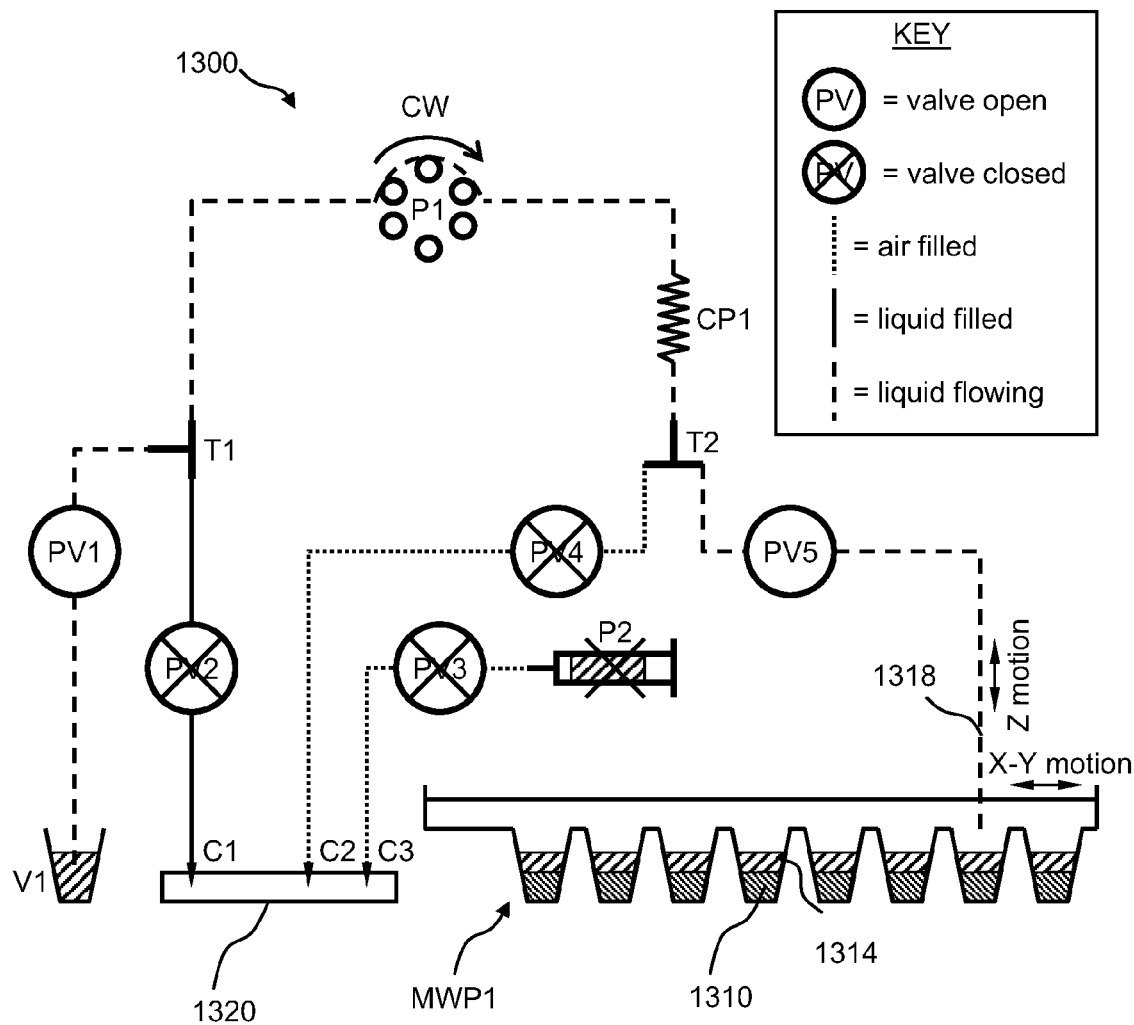

FIG. 13D, with reference to Table 3 below, illustrates a third purging step in which valves PV1 and PV5 are open, valves PV2, PV3, and PV4 are closed, peristaltic pump P1 is activated in the CW direction, and syringe pump P2 is stopped. This arrangement establishes a flow of liquid from vessel V1, through valve PV1, through peristaltic pump P1, through capillary CP1, through one branch of T2, through valve PV5, and through supply line 1318 to MWP1. Liquid displaces air in the path from vessel V1 to MWP1. Air is vented through supply line 1318 to MWP1.

TABLE 3

| PV1 | PV2 | PV3 | PV4 | PV5 | P1 | P2 |
|---|---|---|---|---|---|---|
| OPEN | CLOSED | CLOSED | CLOSED | OPEN | CW | STOP |

Purging Fluidics System—Step 4

Figure 13E:
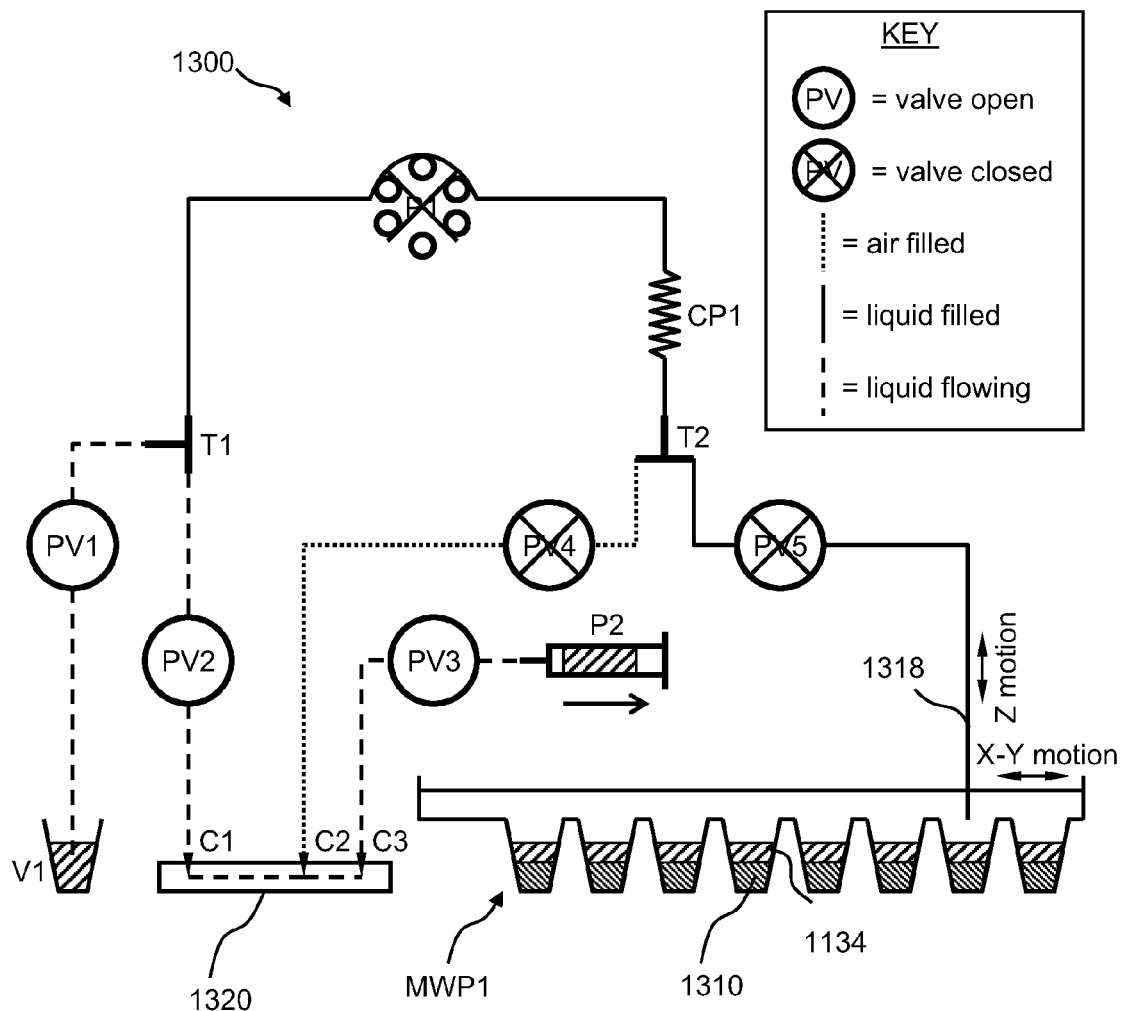

FIG. 13E, with reference to Table 4 below, illustrates a fourth purging step in which valves PV1, PV2, and PV3 are open, valves PV4 and PV5 are closed, peristaltic pump P1 is stopped (i.e., pump P1 acts as a closed valve), and syringe pump P2 is activated in a direction selected to pull liquid from fluidics system 1300. This arrangement establishes a flow of liquid from vessel V1, through valve PV1, through T1, through valve PV2, through droplet actuator 1320 from port C1 to port C3, through valve PV3, and into the cylinder of syringe pump P2. Liquid displaces air in the path from vessel V1 to syringe pump P2. Droplet actuator 1320 is purged of air. Air is drawn into syringe pump P2.

TABLE 4

| PV1 | PV2 | PV3 | PV4 | PV5 | P1 | P2 |
|---|---|---|---|---|---|---|
| OPEN | OPEN | OPEN | CLOSED | CLOSED | STOP | PULL |

Purging Fluidics System—Step 5

Figure 13F:
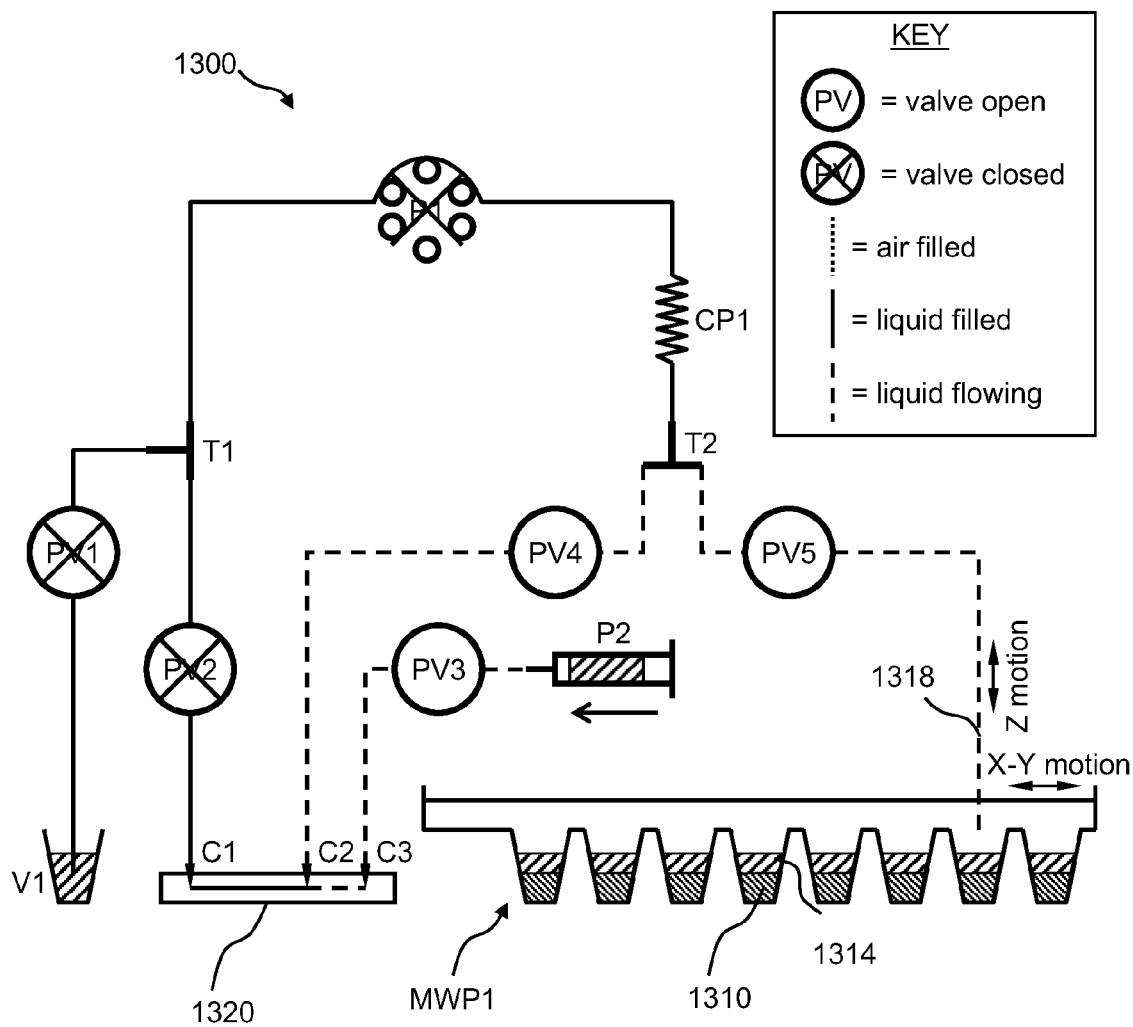

FIG. 13F, with reference to Table 5 below, illustrates a fifth purging step in which valves PV3, PV4, and PV5 are open, valves PV1 and PV2 are closed, peristaltic pump P1 is stopped (i.e., pump P1 acts as a closed valve), and syringe pump P2 is activated in a direction to push liquid into fluidics system 1300. This arrangement establishes a flow of liquid from syringe pump P2, through valve PV3, through droplet actuator 1320 from port C3 to port C2, through valve PV4, through T2, through valve PV5, and through supply line 1318 to MWP1. Liquid displaces air in the path from syringe pump P2 to MWP1. Air is vented through supply line 1318 to MWP1.

TABLE 5

| PV1 | PV2 | PV3 | PV4 | PV5 | P1 | P2 |
|---|---|---|---|---|---|---|
| CLOSED | CLOSED | OPEN | OPEN | OPEN | STOP | PUSH |

At the completion of this step, all air has been purged from fluidics system 1300, and droplet actuator 1320. All liquid lines and elements of fluidics system 1300 and all channels of droplet actuator 1320 are filled with liquid and substantially free of air bubbles.

Loading Droplet Actuator—Step 1

Figure 13G:
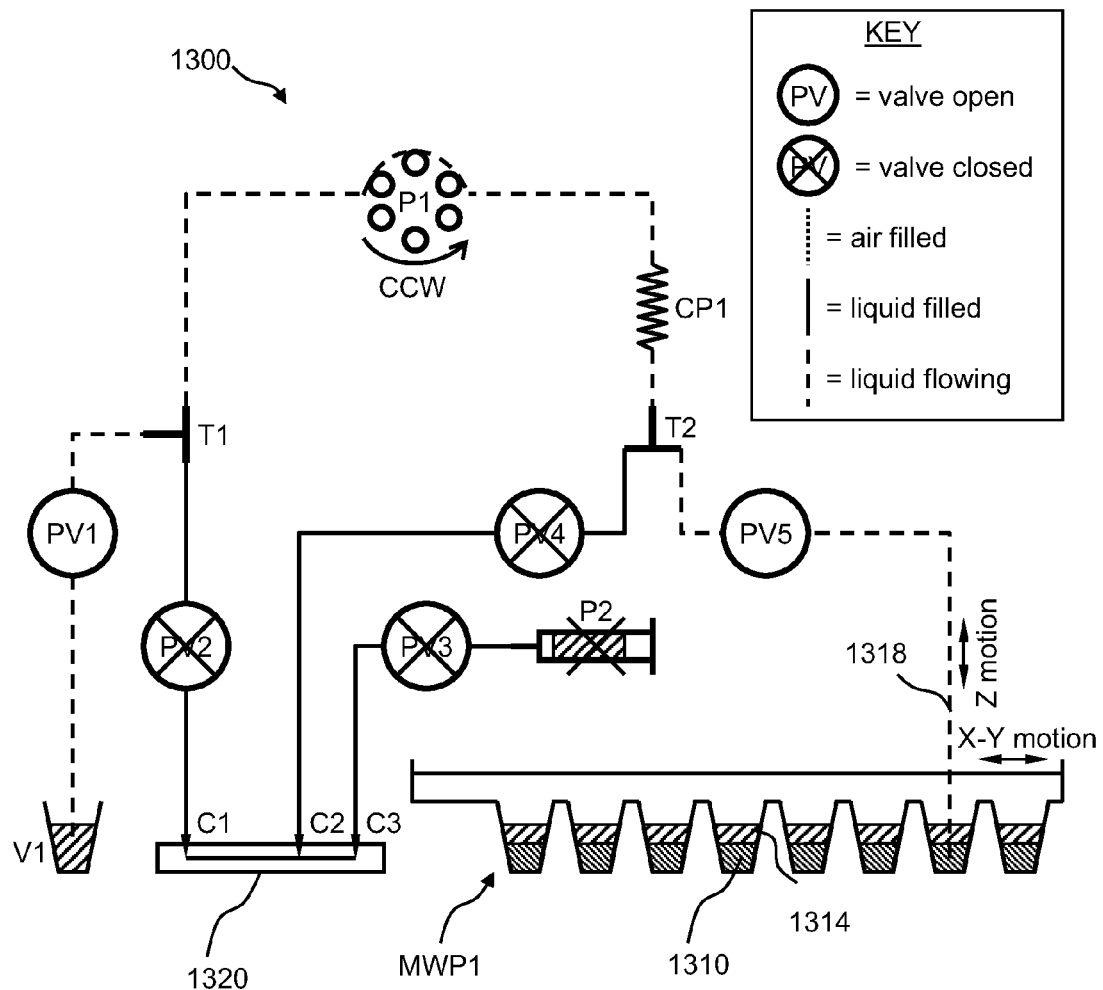

FIG. 13G, with reference to Table 6 below, illustrates an exemplary first step in a method of loading a droplet actuator. Fluidics system 1300 has two pumps, peristaltic pump P1 and syringe pump P2, that are available for loading reagents into droplet actuator 1320. Peristaltic pump P1 of fluidics system 1300 is used for loading reagents into droplet actuator 1320. Valves PV1 and PV5 are open, valves PV2, PV3, and PV4 are closed, peristaltic pump P1 is activated in the CCW direction, and syringe pump P2 is stopped. Additionally, using the xyz-motion, supply line 1318 is inserted into a well of MWP1 that contains the pre-selected reagent 1310. A certain amount of reagent 1310 is drawn from MWP1 in a flow loop through peristaltic pump P1 and toward vessel V1, as indicated in FIG. 13G. Subsequently, supply line 1318 is lifted out of reagent 1310 and into filler fluid 1314 and a certain amount of filler fluid 1314 is drawn from MWP1. In some embodiments, supply line 1318 may oscillate up and down in the well to create multiple slugs. A train of reagent slugs that are separated by filler fluid flows toward capillary CP1. When the entire train of reagent slugs is present within CP1, peristaltic pump P1 is stopped.

TABLE 6

| PV1 | PV2 | PV3 | PV4 | PV5 | P1 | P2 |
|---|---|---|---|---|---|---|
| OPEN | CLOSED | CLOSED | CLOSED | OPEN | CCW | STOP |

Loading Droplet Actuator—Step 2

Figure 13H:
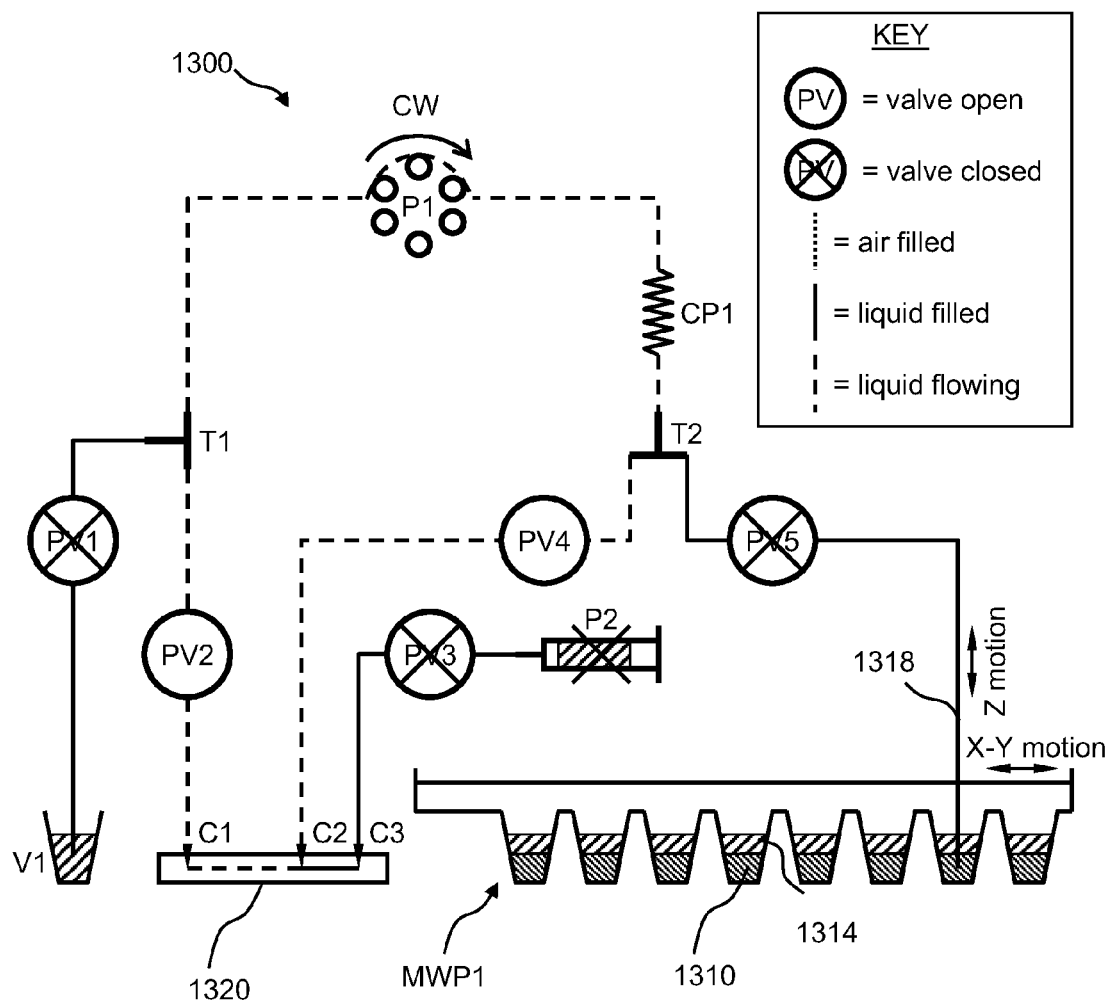

FIG. 13H, with reference to Table 7 below, illustrates an exemplary next step in a method of loading a droplet actuator. Fluidics system 1300 has two pumps, peristaltic pump P1 and syringe pump P2, that are available for loading reagents into droplet actuator 1320. Peristaltic pump P1 of fluidics system 1300 is used for loading reagents into droplet actuator 1320. Valves PV2 and PV4 are open, valves PV1, PV3, and PV5 are closed, peristaltic pump P1 is activated in the CW direction, and syringe pump P2 is stopped. This arrangement establishes a flow loop through droplet actuator 1320 that includes peristaltic pump P1 and capillary CP1, as indicated in FIG. 13H. The train of reagent slugs within capillary CP1 flows into droplet actuator 1320, from port C2 toward port C1, and droplet actuator 1320 is, thus, loaded with the pre-selected reagent and ready for operation.

TABLE 7

| PV1 | PV2 | PV3 | PV4 | PV5 | P1 | P2 |
|---|---|---|---|---|---|---|
| CLOSED | OPEN | CLOSED | OPEN | CLOSED | CW | STOP |

Direct Dispensing Method of Loading a Droplet actuator

Figure 13I:
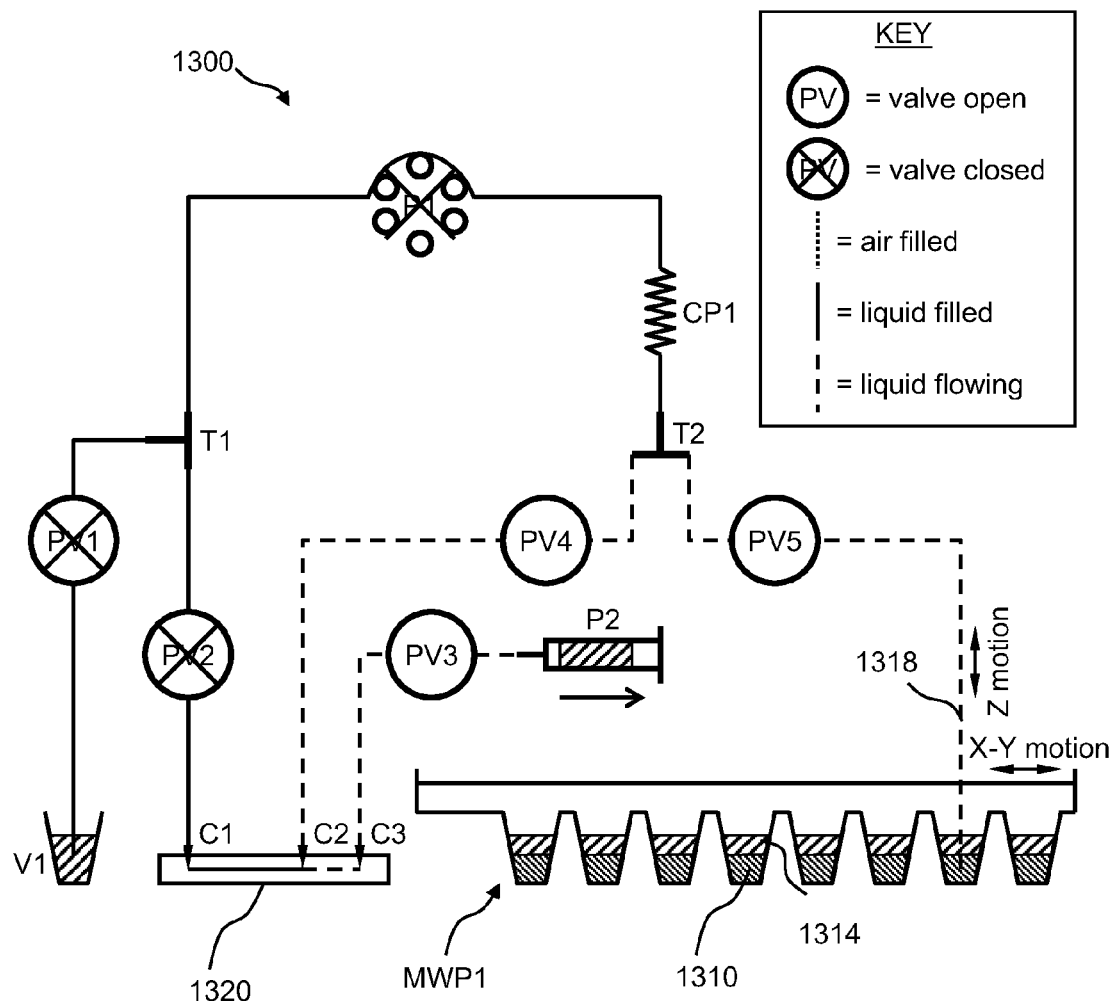

FIG. 13I, with reference to Table 8 below illustrates another step in a method of loading a droplet actuator. Fluidics system 1300 has two pumps, peristaltic pump P1 and syringe pump P2, that are available for loading reagents into droplet actuator 1320. Syringe pump P2 of fluidics system 100 is used for loading reagents into droplet actuator 1320. Valves PV3, PV4, and PV5 are open, valve PV1 is closed, PV2 is optionally closed, peristaltic pump P1 is stopped (i.e., pump P1 acts as a closed valve), and syringe pump P2 is activated in a direction to pull liquid from fluidics system 1300. Additionally, using the xyz motion, supply line 1318 is inserted into a pre-selected well of MWP1 that contains the pre-selected reagent 1310. A certain amount of reagent 1310 is drawn from MWP1 in a flow loop through droplet actuator 1320 from port C2 to port C3 and toward syringe pump P2, as indicated in FIG. 13I. In one example, syringe pump P2 is used for loading a large volume reagent slug from MWP1 into droplet actuator 1320.

TABLE 8

| PV1 | PV2 | PV3 | PV4 | PV5 | P1 | P2 |
|---|---|---|---|---|---|---|
| CLOSED | CLOSED | OPEN | OPEN | OPEN | STOP | PULL |

Figure 14A:
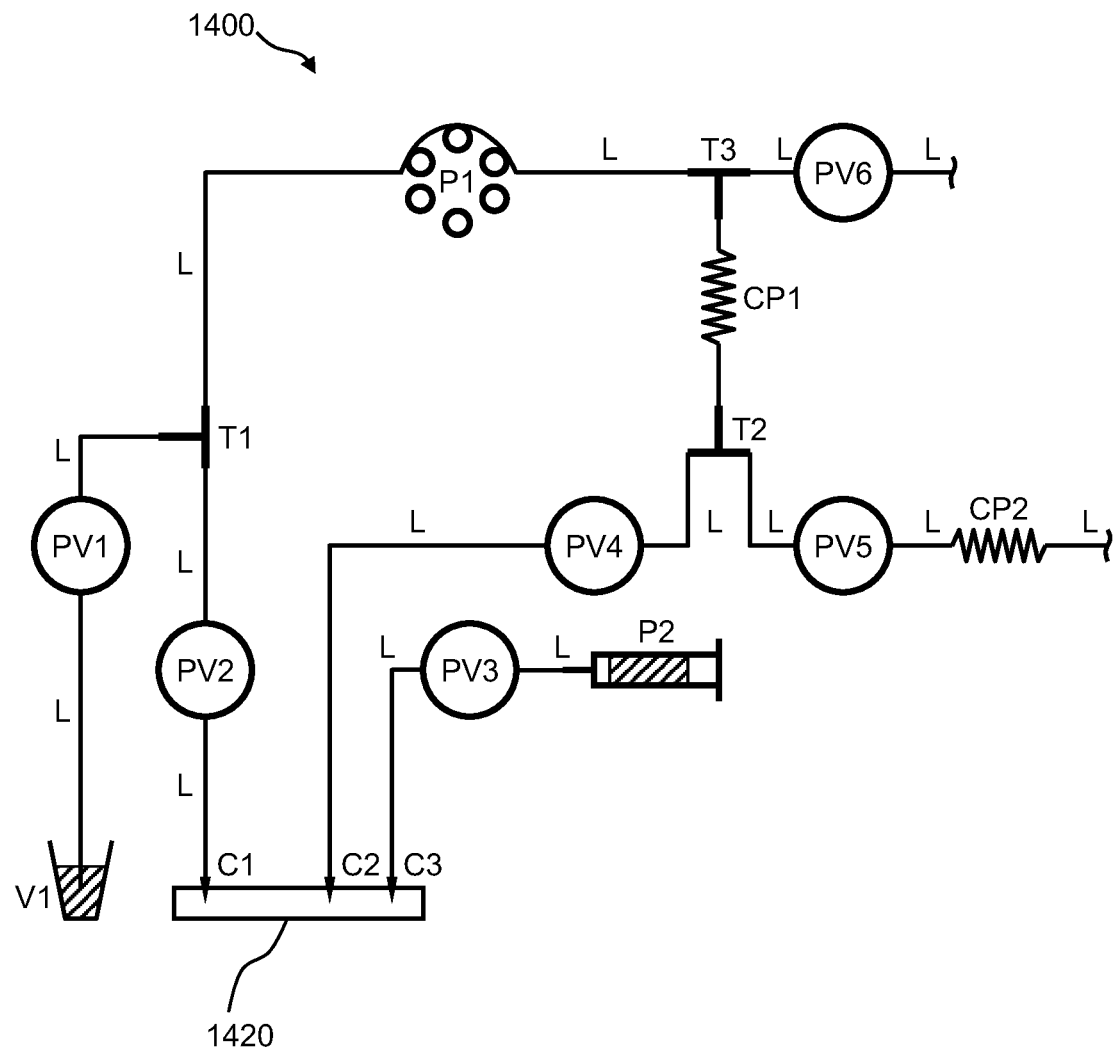
FIGS. 14A, 14B, 14C, 14D, 14E, and 14F are schematic diagrams of another fluidics system for loading liquid receptacle, such as a channel or droplet operations gap of a droplet actuator, with liquid.

FIGS. 14A-14F are schematic diagrams of an example of another fluidics system 1400 for loading a droplet actuator with liquid. With reference to FIG. 14A, fluidics system 1400 may include any arrangement of one or more valves, one or more pumps, one or more capillaries, and one or more liquid supply vessels; all fluidly connected. A droplet actuator to be loaded is fluidly connected to fluidics system 1400. In one example, fluidics system 1400 is substantially the same as fluidics system 1300, except that a vent path that includes a pinch valve PV6 is provided between peristaltic pump P1 and capillary CP1, and MWP1 is replaced with a capillary CP2, which is preloaded with a certain train of reagent slugs. Note that, like fluidics system 1300, all liquid lines L of fluidics system 1400 may be capillaries or other tubes and that capillary CP1 may be an extended length of capillary that couples peristaltic pump P1 and junction T2. Similarly, capillary CP2 may be formed of an extended length of capillary coupled to pinch valve P5.

Fluidics system 1400 is exemplary only, other system variations are possible within the scope of the invention. For example, syringe pump P2 may be replaced with other types of pumps. Alternatively, fluidics system 1400 may include a single pump only.

Purging Air from Fluidics System—Step 1

Figure 14B:
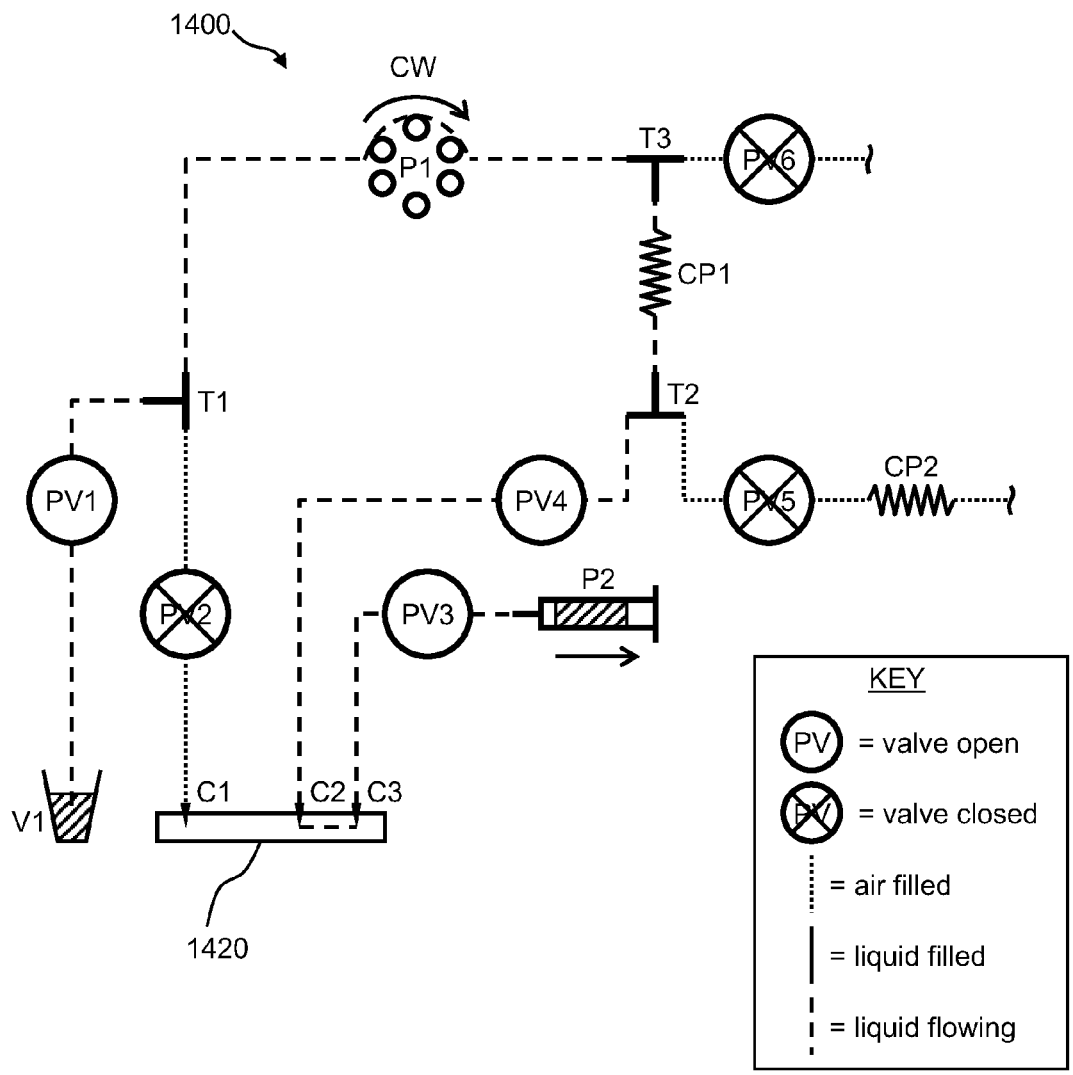

FIG. 14B, with reference to Table 9 below, illustrates a first purging step, in which valve PV1 is optionally open, valves PV3 and PV4 are open, valves PV2, PV5, and PV6 are closed, peristaltic pump P1 is activated in the CW direction, and syringe pump P2 is activated in a direction to pull liquid from fluidics system 1400. By using peristaltic pump P1 and syringe pump P2 simultaneously, liquid is drawn from vessel V1, through valve PV1, through peristaltic pump P1, through capillary CP1, through valve PV4, through droplet actuator 1420, through valve PV3, and into syringe pump P2. Liquid displaces air in the path from vessel V1 to syringe pump P2. Air is drawn into syringe pump P2.

TABLE 9

| PV1 | PV2 | PV3 | PV4 | PV5 | PV6 | P1 | P2 |
|---|---|---|---|---|---|---|---|
| OPEN | CLOSED | OPEN | OPEN | CLOSED | CLOSED | CW | PULL |

Purging Air from Fluidics System—Step 2

Figure 14C:
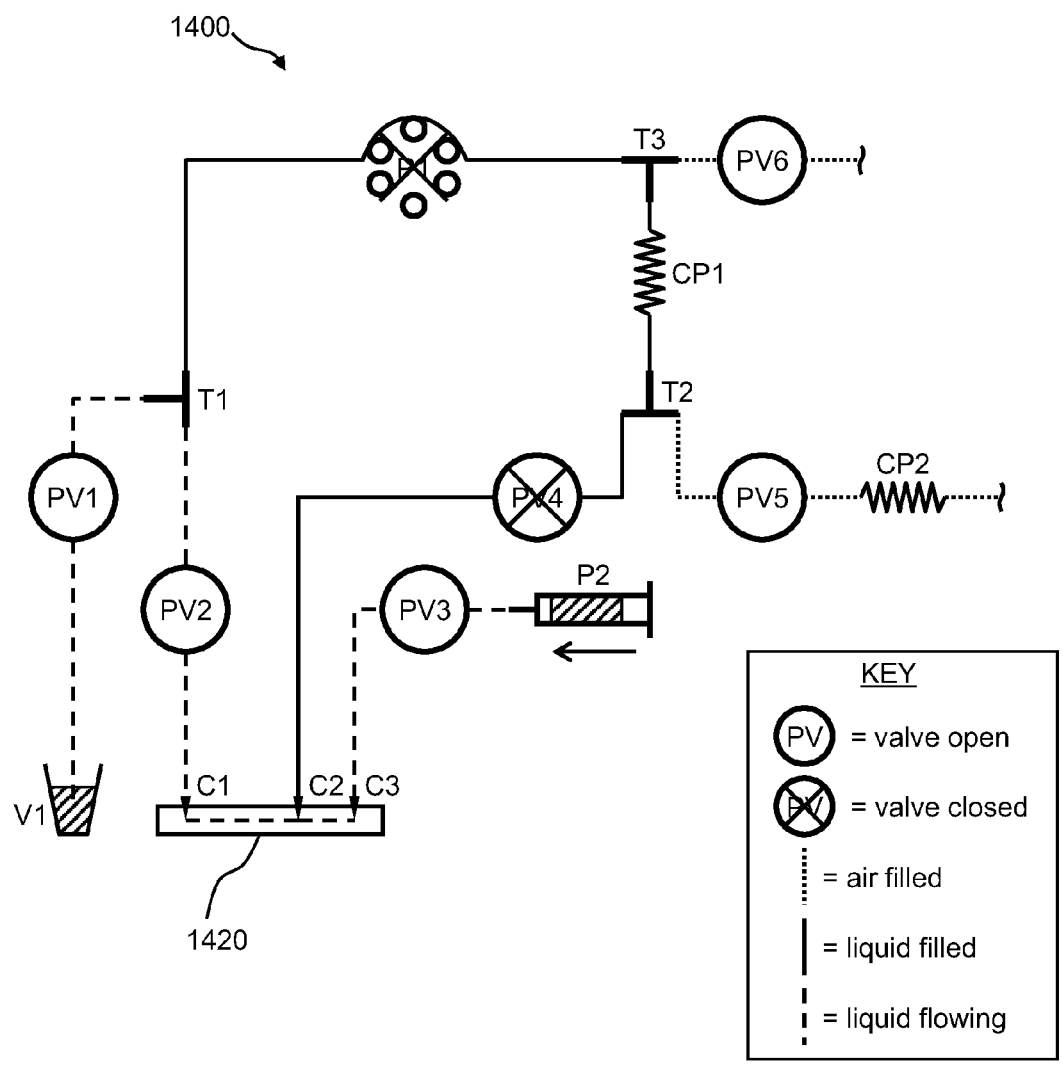

FIG. 14C, with reference to Table 10 below, illustrates a second purging step, in which valves PV1, PV2, PV3, PV5, and PV6 are open, valve PV4 is closed, peristaltic pump P1 is stopped (i.e., pump P1 acts as a closed valve), and syringe pump P2 is activated in a direction to push liquid into fluidics system 1400. This arrangement establishes a flow of liquid from syringe pump P2, through droplet actuator 1420 from port C3 to port C1, through valve PV2, through T1, through valve PV1, and into vessel V1, as indicated in FIG. 14C. Liquid displaces air in the path from syringe pump P2 to vessel V1. Air is vented at vessel V1.

TABLE 10

| PV1 | PV2 | PV3 | PV4 | PV5 | PV6 | P1 | P2 |
|---|---|---|---|---|---|---|---|
| OPEN | OPEN | OPEN | CLOSED | OPEN | OPEN | STOP | PUSH |

Purging Air from Fluidics System—Step 3

Figure 14D:
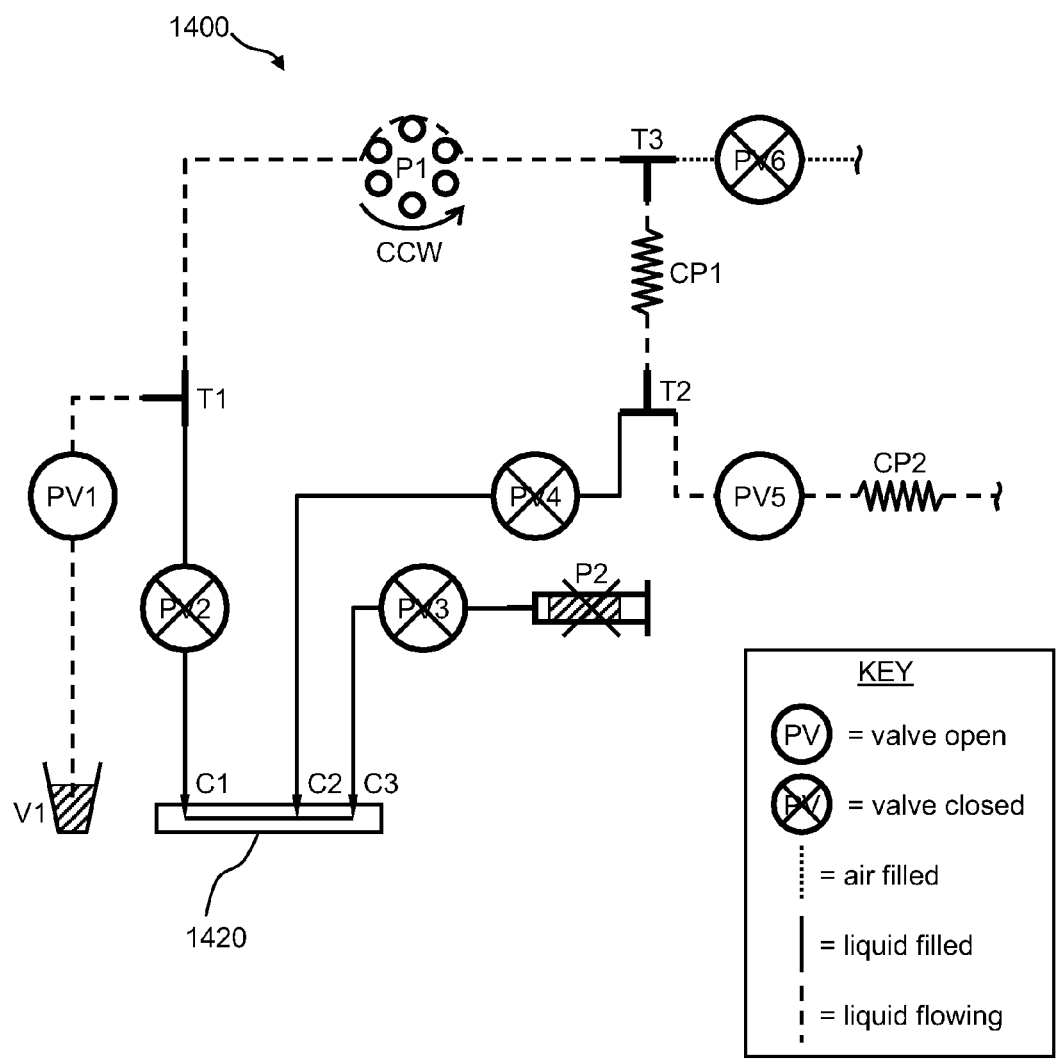

FIG. 14D, with reference to Table 11 below, illustrates a third purging step, in which valves PV1 and PV5 are open, valves PV2, PV3, PV4, and PV6 are closed, peristaltic pump P1 is activated in the CCW direction, and syringe pump P2 is stopped. Peristaltic pump P1 pumps liquid from capillary CP2, through valve PV5, and through T2. Peristaltic pump P1 is operated until such time that any air that precedes the train of reagent slugs from preloaded capillary CP2 is trapped between peristaltic pump P1 and T3.

TABLE 11

| PV1 | PV2 | PV3 | PV4 | PV5 | PV6 | P1 | P2 |
|---|---|---|---|---|---|---|---|
| OPEN | CLOSED | CLOSED | CLOSED | OPEN | CLOSED | CCW | STOP |

Purging Air from Fluidics System—Step 4

Figure 14E:
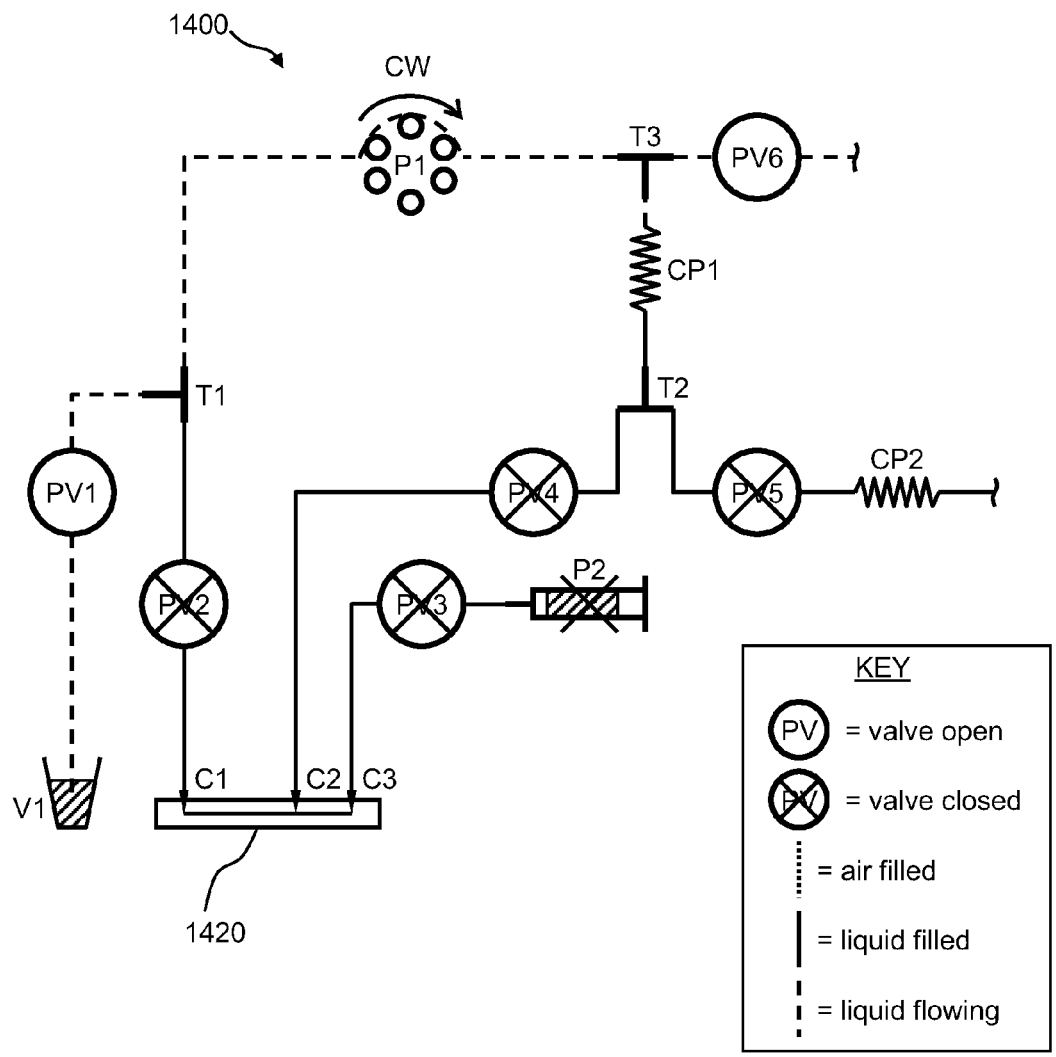

FIG. 14E, with reference to Table 12 below, illustrates a fourth purging step, in which valves PV1 and PV6 are open, valves PV2, PV3, PV4, and PV5 are closed, peristaltic pump P1 is activated in the CW direction, and syringe pump P2 is stopped. This arrangement establishes a flow of liquid between vessel V1 and valve PV6, which is the vent path. Pump P1 pushes air trapped between peristaltic pump P1 and T3 through PV6, through which air is vented from fluidics system 1400.

TABLE 12

| PV1 | PV2 | PV3 | PV4 | PV5 | PV6 | P1 | P2 |
|---|---|---|---|---|---|---|---|
| OPEN | CLOSED | CLOSED | CLOSED | CLOSED | OPEN | CW | STOP |

At the completion of this step, all air has been purged from fluidics system 1400 and droplet actuator 1420, as all liquid lines and elements of fluidics system 1400 and all channels of droplet actuator 1420 are filled with liquid and substantially free of air bubbles.

Loading a Droplet Actuator

Figure 14F:
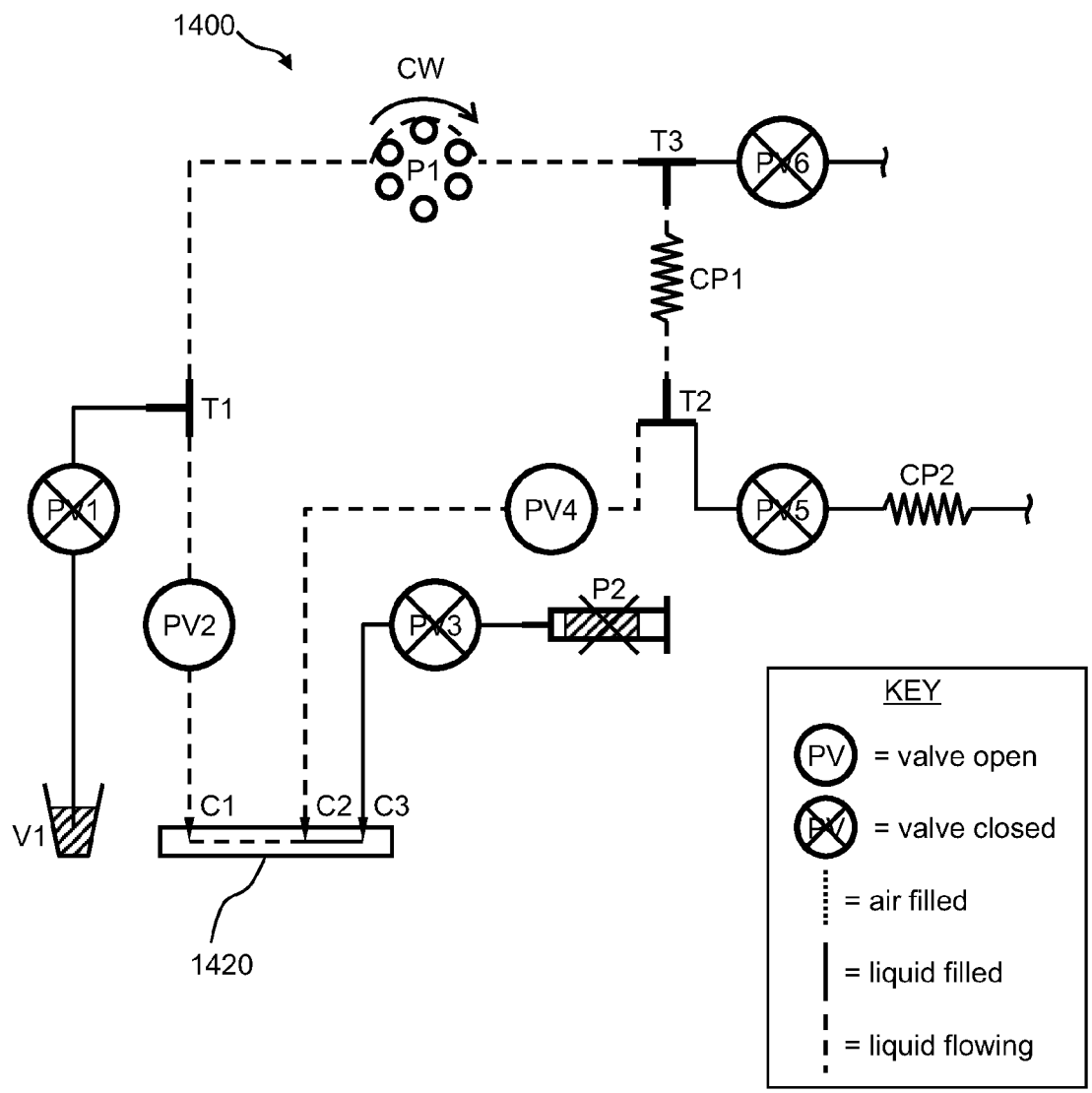

FIG. 14F, with reference to Table 13 below illustrates a step in a method of loading a droplet actuator. Valves PV2 and PV4 are open, and valves PV1, PV3, PV5, and PV6 are closed, peristaltic pump P1 is activated in the CW direction, and syringe pump P2 is stopped. Because fluidics system 1400 contains all filler fluid and reagent slugs necessary for the operation of droplet actuator 1420, the pumping action of peristaltic pump P1 moves the train of reagent slugs into droplet actuator 1420, from port C2 to port C1, as indicated in FIG. 14F.

TABLE 13

| PV1 | PV2 | PV3 | PV4 | PV5 | PV6 | P1 | P2 |
|---|---|---|---|---|---|---|---|
| CLOSED | OPEN | CLOSED | OPEN | CLOSED | CLOSED | CW | STOP |

7.6 Sample Processing

The invention provides a droplet actuator device and methods for processing samples for use on a droplet actuator device. For example, the invention provides methods of processing samples for conducting genetic analysis of microbiological organisms in a biological sample. The device and methods of the invention may be used to detect and identify microorganisms such as bacteria, viruses, and/or fungi in a biological sample. Examples of biological samples include, blood, plasma, serum, isolated microorganisms, nucleic acid spiked into an assay buffer, other samples described herein, and other known sample types. In various embodiments, the invention provides for droplet actuator-based sample preparation and nucleic acid analysis. The device and methods of the invention may, in one embodiment, be used for rapid and accurate identification of atypical bacteria that have specific treatment implications, such as selection of effective antibiotics and length of therapy. For example, in the immunosuppressed population the ability to distinguish between bacteria, viruses, and fungi both rapidly and accurately will be life-saving.

7.6.1 Sample Preprocessing

The invention provides a droplet actuator device and methods for pre-processing samples prior to introduction of the samples onto a droplet actuator. Prior to transfer of sample to the droplet actuator, the sample may be combined with magnetic beads having affinity for analytes (e.g., DNA and/or RNA) of interest. The analytes of interest may be bound to the magnetically responsive capture beads. The magnetically responsive beads may be concentrated in a small part of the processed sample volume. The reduced sample volume that contains the magnetically responsive beads may be loaded onto the droplet actuator. For example, volume reduction may be from about >1 milliliter (mL) to about <10 microliters (µL).

The droplet actuator may be provided as part of a system which is programmed to execute analysis protocols using electrical fields to perform droplet operations. For example, in a real-time PCR assay, thermocycling is accomplished by transporting reaction droplets through isothermal temperature zones within the droplet actuator rather than by cycling the heaters ("flow-through" PCR). This and other PCR approaches are described in Pollack et al., International Patent Application No. PCT/US 06/47486, entitled "Droplet-Based Biochemistry," filed on Dec. 11, 2006, the entire disclosure of which is incorporated herein by reference.

The droplet actuator may be electrically coupled with the system using mating alignment features to ensure proper positioning. The mating alignment features align the droplet actuator with various functional elements, such as heaters, magnets, and detection elements, that are aligned with specific regions of droplet actuator. A sample is loaded into the sample well. The sample well may be sealed before the analysis protocol can be started. Once the analysis protocol is started, it proceeds to completion without requiring operator intervention. Using one or more droplet operations, the sample is combined in the cassette with appropriate reagents, such as lysis buffer, capture buffer, and capture beads, as required by the analysis protocol. Meanwhile the droplet actuator is primed for performing the final assay (e.g., real-time PCR).

The low thermal mass of the droplets combined with the speed and agility with which they can be positioned using one or more droplet operations enables extremely rapid and precise thermal profiles to be achieved. The inventors have successfully implemented real-time PCR in microfluidic format, which includes tests for bacterial and fungal pathogens (*Bacillus anthracis, Franciscella tularensis, Candida albicans, Mycoplasma pneumoniae, Eschericia coli*, Methicillin-resistant *Staphylococcus aureus* (MRSA)), human gene targets (RPL4, CFTR, PCNA) and RNA.

Figure 15A:
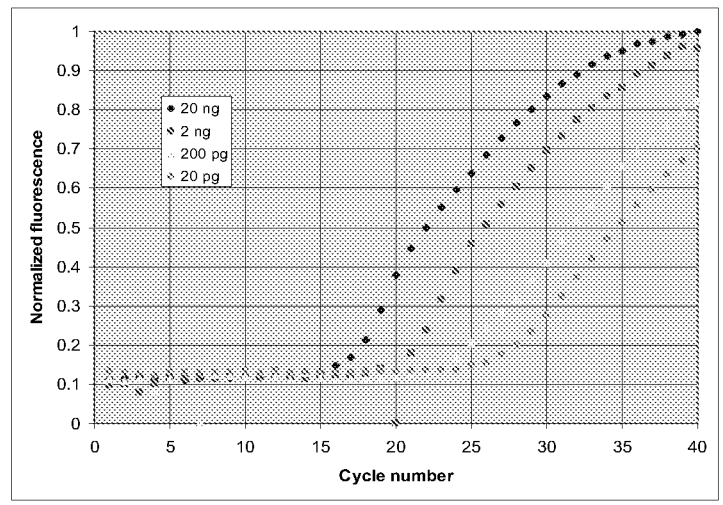
FIG. 15A shows a plot of real-time PCR data for detection of MRSA using digital microfluidics.
Figure 15B:
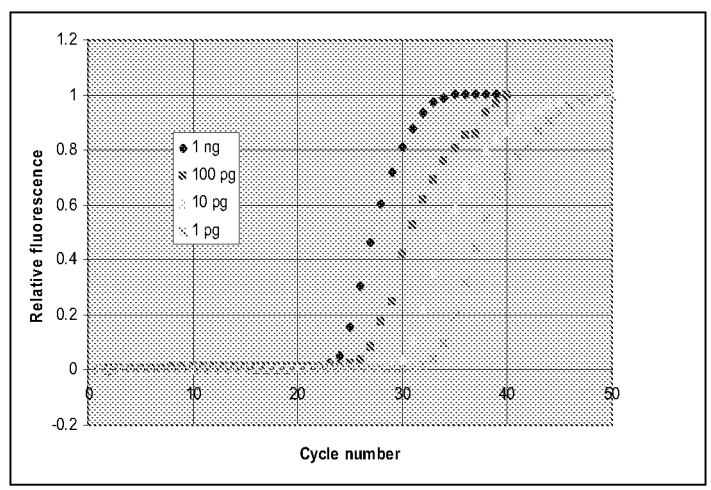
FIG. 15B shows a plot of real-time PCR data for detection of Bacillus anthracia using digital microfluidics.

FIG. 15A shows a plot of real-time PCR data for detection of MRSA using digital microfluidics. FIG. 15B shows a plot of real-time PCR data for detection of *Bacillus anthracis* using digital microfluidics.

Referring to FIG. 15A, for detection of MRSA by real-time PCR, a forward primer mecii574 (5'-GTC AAA AAT CAT GAA CCT CAT TAC TTA TG-3') and reverse primer Xsau325 (5'-GGA TCA AAC GGC CTG CAC A-3') were used to amplify a 176 bp fragment of *Staphylococcus aureus* genomic DNA (ATCC #700699D-5). The 50 µl PCR mix was comprised of 20 mM Tris HCl (pH 8.4), 50 mM KCl, 200 µM dNTPs, 1 µM of each primer, 2× Evagreen (Biotium), 6.125U of KAPA2G Fast DNA polymerase (Kapa Biosystems). This mix was adjusted to 50 µl with H20 and approximately 1-2 µL of this mixture was loaded in one of the droplet actuator reservoirs.

The protocol performed on the droplet actuator was to dispense two (450 mL) droplets from the reservoir and combine them to form a single (900 mL) reaction droplet. When sample and reagent are provided separately one droplet would be for the sample and the other droplet would be for the 2× reaction mixture. The droplets are then transported to the 95° C. zone and, following an initial activation step, the droplets are cycled between the 60° C. and 95° C. zones 40 times. A fluorescence reading was taken at the end of each extension cycle within the 60° C. zone. The two positions were spanned by 16 electrodes and the droplets were typically transferred at a rate of 20 electrodes per second, thus the time to transfer the droplet between the two thermal zones was approximately 750 milliseconds (ms). Real-time PCR curves obtained for 10-fold dilutions of MRSA genomic DNA concentration exhibited roughly the expected 3.3 cycle separation. The results were confirmed by gel analysis of the amplified product collected from the droplet actuator (not shown). In all cases the amplified product was of the expected length and no by-products were observed.

Referring to FIG. 15B, an experiment was also conducted to evaluate detection of *Bacillus anthracis* (anthrax) using digital microfluidic PCR. These experiments were performed using an early version of a droplet actuator and instrument and were not optimized for speed. Genomic DNA (chromosomal & plasmids) and primers targeted against *B. anthracis* protective antigen were provided from a commercially available kit (Idaho Technology, Salt Lake City, Utah) and combined with a similar reaction mixture to that described above for detection of MRSA. These experiments were performed with varying amounts of the DNA (i.e., 1 ng, 100 pg, 10 pg, 1 pg genomic DNA) added into the reactions which were amplified on the droplet actuator. Cycling conditions were 10 sec at 95° C. and 60 sec at 60° C. times 40 cycles. The data demonstrate the expected quantitation with detection down to 1 pg of genomic DNA.

7.6.2 Capture, Concentration and Elution of Nucleic Acids

The invention provides droplet actuator devices, techniques and systems for capturing, concentrating and/or eluting nucleic acids.

Figure 16:
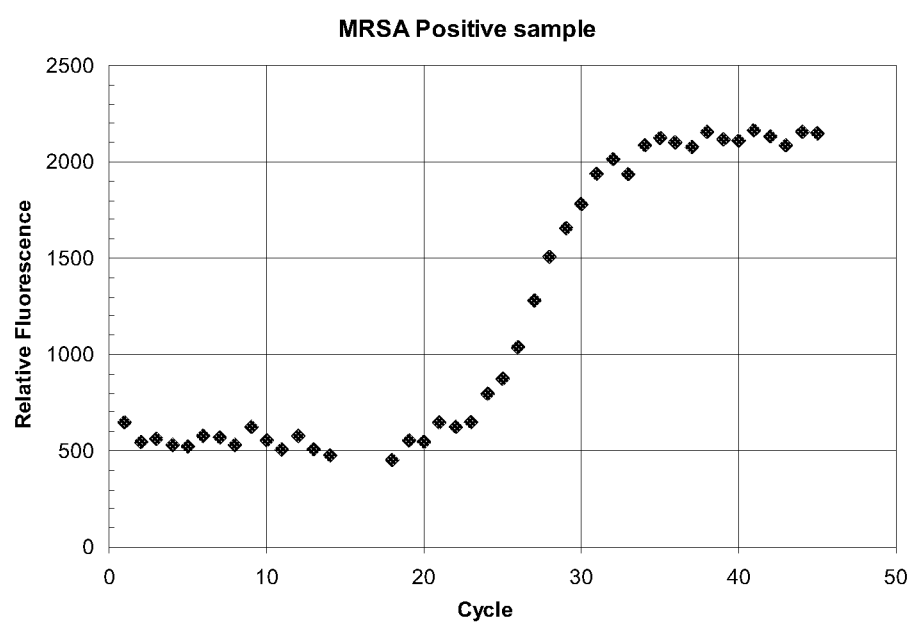
FIG. 16 shows a plot resulting from amplification of MRSA genomic DNA captured, concentrated and eluted on a droplet actuator.

FIG. 16 shows a plot resulting from amplification of MRSA genomic DNA captured, concentrated and eluted on a droplet actuator. In operation, a droplet actuator is electrically coupled to the instrument (not shown). A suspension of magnetically responsive beads that contain captured DNA in a lysis solution was loaded into a sample reservoir of the droplet actuator. In an alternative embodiment, the lysis solution that contains MRSA genomic DNA may be provided as a droplet on a droplet actuator and combined with the bead-containing droplet on the droplet actuator. A permanent magnet located in close proximity to the droplet actuator is used to collect the magnetically responsive beads at the bottom of the well. A single droplet is dispensed from the sample reservoir. The single droplet contains substantially all of the magnetically responsive beads from the original sample, effectively concentrating the beads by a factor of about 50 or more. The droplet is then transported to a wash station where the magnetically responsive beads are magnetically immobilized and repeatedly washed. For about the last several washes, the wash fluid is switched to an elution buffer. The droplets that contain eluted DNA are accumulated within another reservoir. The purified DNA droplet is subsequently dispensed from the reservoir and mixed with multiple sets of PCR reagent droplets. The droplets are transported to the heater zone of the deck and flow-through real-time PCR is performed.

As a proof of concept, genomic MRSA DNA was added to several mL of cell lysis solution that contained DNA-capture magnetically responsive beads. The beads were then concentrated off-actuator and transferred in 15 µL of solution to the sample well of the droplet actuator. The beads were further concentrated into a single (~300 mL) DNA capture droplet. The DNA capture droplet was washed using a merge-and-split protocol with 8 droplets of TE buffer (pH 7.0) and then eluted with 12 droplets of TE buffer (pH 8.5) into a reservoir. Droplets of purified DNA were then dispensed and mixed in a 1:1 ratio with a real-time PCR mix.

Data indicate that sample concentration, elution, and detection were successfully performed on a droplet actuator.

7.6.3 Sample Preparation on a Droplet Actuator

On-actuator preparation of biological samples provides a method for sensitive isolation of nucleic acids using one or more droplet operations to perform separation protocols. Droplet actuator-based sample preparation includes lysis (when necessary) of a sample, capture of nucleic acids (e.g., on magnetically responsive beads), pre-concentration of nucleic acids, a washing of captured nucleic acids to remove unbound material prior to analysis. The flexibility and programmability of the droplet actuator provides for variation in the order in which sample and reagents may be combined during sample preparation.

In one embodiment, a sample droplet may be combined using one or more droplet operations with a lysis buffer droplet in order to yield a lysed sample droplet in which nucleic acid has been released. A droplet that includes magnetically responsive capture beads may be combined with the lysed sample droplet in order to bind nucleic acid, yielding a nucleic acid capture droplet in which nucleic acid is bound to the magnetically responsive beads. The nucleic acid capture droplet may be transported using one or more droplet operations into the presence of a magnet and washed using a merge-and-split wash protocol to remove unbound material, yielding a washed bead-containing droplet substantially lacking in unbound material. In some applications, the washed bead-containing droplet may be merged with an elution buffer droplet to elute the nucleic acid, yielding a bead-containing elution droplet. The bead-containing elution droplet may be transported using one or more droplet operations into a thermal zone in order to promote release of the nucleic acid. In other applications, the washed bead-containing droplet may be transported using one or more droplet operations into a thermal zone to promote release of the nucleic acid. The eluted nucleic acid contained in the droplet surrounding the magnetically responsive beads may then be transported away from the magnetically responsive beads for further processing, e.g., PCR analysis.

In an alternative embodiment, a lysis buffer droplet that includes magnetically responsive beads may be combined using one or more droplet operations with a sample droplet to yield a nucleic acid capture droplet in which nucleic acid is bound to the magnetically responsive beads.

In yet another embodiment, a sample droplet that includes magnetically responsive beads may be combined using one or more droplet operations with a lysis buffer droplet to yield a nucleic acid capture droplet in which nucleic acid is bound to the magnetically responsive beads.

In yet another embodiment, a sample droplet may be combined using one or more droplet operations with a lysis buffer droplet in order to yield a lysed sample droplet. A wash buffer droplet that includes magnetically responsive beads may be combined with the lysed sample droplet in order to yield a nucleic acid capture droplet in which nucleic acid is bound to the magnetically responsive beads.

In yet another embodiment, magnetically responsive beads may be pre-concentrated prior to being loaded on the droplet actuator. For example, as the result of off-actuator processing, analytes in (e.g., nucleic acid) may be captured on magnetically responsive beads. The magnetically responsive beads may, for example, be provided in the sample, a lysis solution, or a wash solution. This approach permits the beads to be assembled into a volume which is a small part of the total sample volume. This small volume of beads may then be loaded onto the droplet actuator, e.g., into a reservoir for on-actuator dispensing. Dispensing may result in the production of a number of unit-sized, bead-containing droplets. The magnetic capture beads may be further consolidated, as needed, on the droplet actuator for conducting a droplet-based assay protocol.

7.6.4 Preparation of Viral RNA

Viral RNA may be prepared using, for example, Dynabeads SILANE viral NA from Dynal. A droplet including Proteinase K and a viral sample may be combined using one or more droplet operations with a lysis buffer droplet to yield a lysed sample droplet in which RNA has been released. A droplet including magnetically responsive Dynabeads may be combined with the lysed sample droplet to bind RNA, yielding an RNA capture droplet in which RNA is bound to the Dynabeads. The RNA capture droplet may be transported using one or more droplet operations into the presence of a magnet and washed using a merge-and-split wash protocol to remove unbound material, yielding a washed bead-containing droplet substantially lacking in unbound material. A droplet including elution buffer may be merged with the washed bead-containing droplet to elute RNA, yielding a bead-containing elution droplet. The bead-containing elution droplet may be transported using one or more droplet operations into a thermal zone to promote release of RNA from the Dynabeads, e.g., by heating to approximately 70° C. The eluted RNA contained in the droplet surrounding the Dynabeads may then be transported away from the Dynabeads for further processing, e.g., for execution of a droplet based RT-PCR protocol. Viral DNA may be prepared using, for example, Dynabeads SILANE viral NA from Dynal.

7.6.5 Preparation of Bacterial Genomic DNA

Bacterial genomic DNA, such as genomic DNA from *Bacillus anthracis*, may be prepared using beads having an affinity for DNA. For example, Dynabeads DNA DIRECT from Dynal may be used. A droplet including lysis buffer and magnetically responsive Dynabeads may be combined using one or more droplet operations with a bacterial sample to yield a lysed sample droplet in which released DNA is bound to the Dynabeads. The DNA capture droplet may be transported using one or more droplet operations into the presence of a magnet and washed using a merge-and-split wash protocol to remove unbound material, yielding a washed bead-containing droplet substantially lacking in unbound material. A droplet including resuspension buffer may be merged with the washed bead-containing droplet, yielding a DNA/bead-containing droplet. The DNA/bead-containing droplet is ready for further processing, e.g., for execution of a droplet based PCR protocol. Alternatively, the DNA/bead-containing droplet may be transported using one or more droplet operations into a thermal zone to promote release of DNA from the Dynabeads, e.g., by heating to approximately 65° C. The eluted DNA contained in the droplet surrounding the Dynabeads may then be transported away from the Dynabeads for further processing, e.g., for execution of a droplet based PCR protocol.

7.7 Droplet Actuator Systems

The invention provides droplet actuators with storage and/or transmission devices useful for controlling and/or monitoring distribution and/or use of droplet actuators. The invention also provides networked systems and methods of using such networked systems for controlling and/or monitoring distribution and/or use of droplet actuators.

Figure 17:
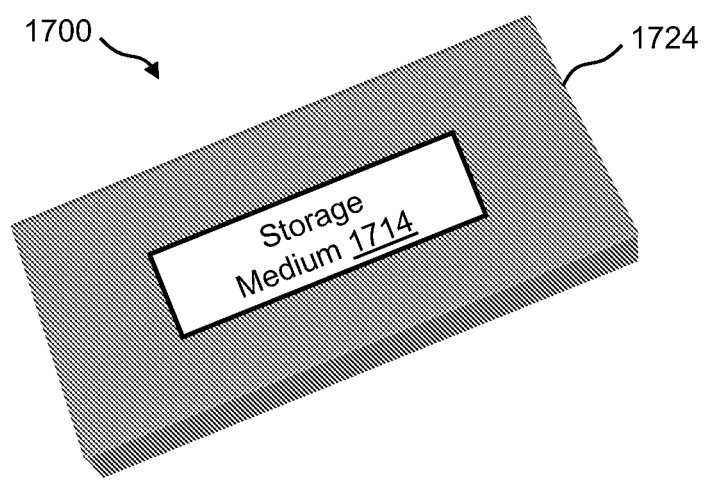
FIG. 17 illustrates a droplet actuator device of the invention, including a droplet actuator with an electronic storage and/or transmission element.

FIG. 17 illustrates a droplet actuator device 1700 of the invention. Droplet actuator device 1700 includes droplet actuator 1724. Droplet actuator 1724 includes an electronic storage and/or transmission element 1714. Electronic storage and/or transmission element 1714 may be affixed to and/or incorporated in droplet actuator 1724 or affixed to and/or incorporated in a cartridge incorporating droplet actuator 1724. Storage and/or transmission element 1714 may, for example, include semiconductor memory, magnetic storage, optical storage, and/or other available forms of computer readable data storage. Storage and/or transmission element 1714 may be volatile or non-volatile. Examples of specific storage and/or transmission elements 1714 include radio-frequency identification (RFID) tags, read-only memory (ROM), random access memory (RAM), electrically erasable programmable read-only memory (EEPROM) (such as flash memory), and magnetic stripes.

In one embodiment, the storage and/or transmission element includes an RFID tag. The RFID tag may be affixed to and/or incorporated in the droplet actuator or droplet actuator cartridge. For example, where the substrate of the droplet actuator is made from a printed circuit board (PCB), the RFID tag may also be mounted on the PCB. The RFID tag may provide for wireless identification of the droplet actuator. For example, the RFID tag may transmit a unique identifier for each droplet actuator. RFID monitors, such as those manufactured by Texas Instruments (Dallas, Tex.), may track the location and use of the droplet actuator. In one embodiment, the invention provides a system in which a subject's RFID and a droplet actuator's RFID are scanned at a subject's bedside into a system which matches the subject with the droplet actuator. The subject's sample may be loaded onto the droplet actuator, for example, into a droplet actuator reservoir and/or into the droplet operations gap of the droplet actuator. The droplet actuator may be mounted on an instrument and used to execute an assay using the sample. Upon completion of the assay, assay results may be automatically associated with the subject. In some embodiments, the information may be automatically added to the laboratory information system or hospital information system or the subject's electronic medical records. Similar methods may be used in testing applications outside of the medical field.

In another example, the storage and/or transmission element includes a memory device, such as a random access memory (RAM) device, read-only memory (ROM) device, or a flash drive. For example, such a droplet actuator may be provided in the form of a peripheral connect device, such as a USB device, that plugs into a computer to power the droplet actuator and permit data exchange between the computer and the device. As another example, the droplet actuator can also be connected and powered by a personal digital assistant (PDA) or a smartphone or a mobile phone. Identifying information from the droplet actuator may be read by the computer, and output information from the assay may be stored on the computer and/or the USB device.

In another embodiment, the invention provides a system for conducting environmental studies, such as studies relating to pollution and/or biological or chemical warfare agents. The device may include a droplet actuator in an instrument associated with the droplet actuator including elements required to power the droplet actuator and/or control the droplet actuator. The system may also include elements for gathering other information, such as temperature, humidity, GPS location, and the like. Information including the results of the assay and the other information may be transmitted to a networked computer. Information including the results the assay and the other information may alternatively be stored on the droplet actuator device and information from multiple devices may be transported to an uploading station where the information may be aggregated onto a computer or a computer network.

In one embodiment, the invention provides a system for detecting and tracking the extent of a chemical or biological attack or release of a dangerous chemical. Droplet actuators may be installed at various locations throughout a target region, for example, on buildings, farms, water supply sources, buoys, weather balloons, etc. Droplet actuators may be installed on mobile devices, such as mobile robotic devices, airplanes, unmanned drones, and vehicle fleets (such as police cars, school buses, ambulances, military vehicles, oceangoing vessels, postal vehicles, commercial vehicles, etc.). Droplet actuators may be associated with GPS systems for determining coordinates of the droplet actuators when samples are taken. Tests may be executed using the droplet actuator devices, and results may be transmitted back to a central location, along with sample collection location information, for aggregation and analysis.

Figure 18:
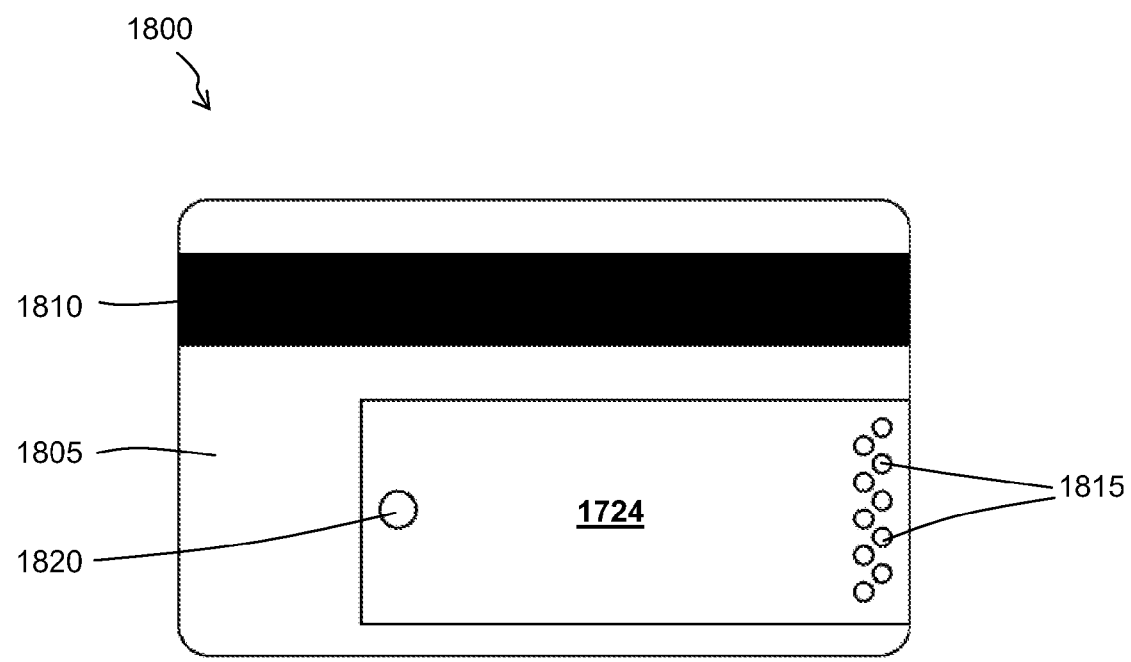
FIG. 18 illustrates another droplet actuator device of the invention, including a droplet actuator with an electronic storage and/or transmission element, where the electronic storage and/or transmission element includes a magnetic stripe card.

FIG. 18 illustrates another embodiment, droplet actuator 1724 is provided as part of a magnetic stripe card device 1800. Card device 1800 includes a card 1805 with a magnetic stripe 1810 affixed thereto for receiving and storing data. A droplet actuator 1724 is also affixed to the card. Droplet actuator 1724 may include electrical contacts 1815 for electrically coupling droplet actuator 1724 to an instrument. Alternatively, droplet actuator 1724 may be electrically connected to wires on card 1805. Wires on card 1805 may terminate in contacts, and these contacts may be electrically coupled to electrical contacts on the instrument so that the droplet actuator may be controlled by the instrument. Droplet actuator 1724 may include an opening 1820 or loading mechanism for loading a sample into droplet actuator 1724 in a manner which subjects the sample to droplet operations mediated by electrodes coupled to the electrical contacts and controlled by the instrument to which the card/droplet actuator is electrically coupled.

In some embodiments, the card may have the shape and size of a standard credit card, and magnetic stripe 1810 may have a location on card 1805 which is similar to the location of the magnetic stripe on a standard credit card. Magnetic stripe 1810 may be, for example, any magnetic stripe capable of storing data, such as those commonly used on magnetic stripe cards (e.g., credit cards, identity cards, and transportation tickets). Magnetic stripe 1810 may be read by physical contact and swiping past a reading head (not shown), as is well known. In one embodiment, the instrument is configured so that magnetic stripe 1810 may be read as the card is inserted into the instrument. Further, information from the assay may be written to magnetic stripe 1810 during and/or following the completion of the assay.

The instrument may be configured in a manner similar to an automated teller machine, in which the card is inserted by a user, a card reader device transports the card into an operational position in which the card electrical contacts are coupled to the instrument. Establishing the card in operational position may be controlled by a card insertion device and/or may be manually controlled. Further, in operational position, any detection region or window on the droplet actuator may be aligned with a detector on the instrument. In operational position, the instrument may control the execution of an assay on the droplet actuator, and then read and store information to and from the magnetic stripe. Information from magnetic stripe 1810 may be read by a magnetic stripe reader. An assay may be conducted, and information pertaining to assay results may be written to magnetic stripe 1810. The instrument may be coupled to a network and may upload results from the assay to the network, e.g., into an electronic medical record system. The instrument may include an output device, such as a display and/or printer, which outputs information pertaining to assay results. In another embodiment, a magnetic stripe reader/writer at a subject's bedside is used to associate card 1800 with a specific subject, e.g., by reading a card identifier from magnetic stripe 1810 and copying the identifier into a subject record and/or by writing a subject identifier onto card 1800. Magnetic stripe 1810 may also include information about the expiration date of card device 1800, information about the assay type, instructions for a user for electronic display by the instrument, and software instructions for controlling the assay or selecting a software protocol on the instrument for controlling the assay. Further, printed material on card device 1800 may also include information about the expiration date of card device 1800, information about the assay type, instructions for a user. In an alternative embodiment, the card is a smart card containing an integrated circuit actuator. The card may have metal contacts connecting the card physically to the reader. Similarly, the card may be a contactless card that uses a magnetic field or radio frequency (RFID) for proximity reading. A battery supply may be included on the card for self-contained execution of an assay.

As noted, the invention provides a droplet actuator with electronic storage and/or transmission element. Information that may be stored and/or transmitted by the electronic storage and/or transmission element includes, for example, sample identification information, test identification information (such as assay type), and subject identification information. Examples of subject identification information include medical history information, subject contact information, insurance information, and test results information. In short, the information may include any data of interest suited for the application in which it is used. Systems that use the droplet actuators of the invention that have data storage capability may, for example, provide the advantage of automated tracking, automated distribution, reduction in medical errors, and/or improved anonymity.

Figure 19:
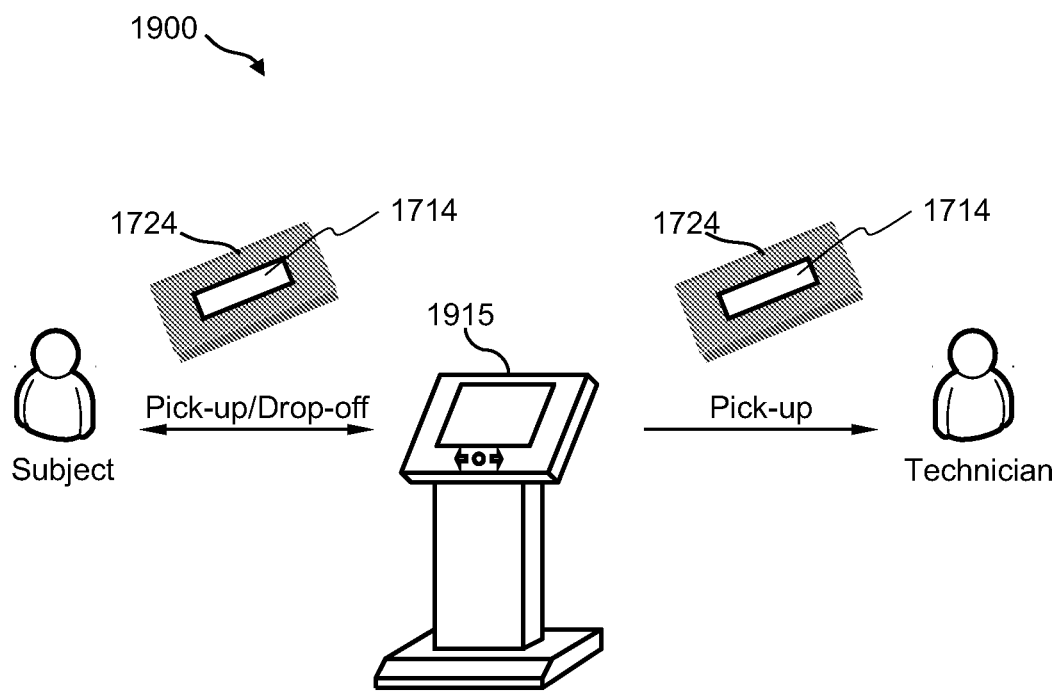
FIG. 19 is a functional diagram of a sample collection and analysis system of the invention.

FIG. 19 is a functional diagram of a sample collection and analysis system 1900 of the invention. System 1900 utilizes droplet actuators 1724 of the invention that have data storage components 1714. In this embodiment, sample collection system 1900 includes one or more kiosks 1915 for dispensing one or more droplet actuators 1724. Kiosks 1915 may be standalone kiosks or may be provided as components of a computer network, such as a wide area network (WAN) or local area network (LAN). Kiosk 1915 may be located, for example, in a pharmacy, grocery store, mall, gas station, doctor's office, hospital, clinic, and/or any convenient location suited for collecting samples. An example method of using system 1900 may include, but is not limited to, the following steps:

Step 1: Using kiosk 1915, a subject obtains a droplet actuator 1724. For example, droplet actuator 1724 may be purchased by the subject using a credit card transaction. Droplet actuator 1724 is dispensed from kiosk 1915. The subject may input identifying information into system 1900 using kiosk 1915. Kiosk 1915 may include a keypad for inputting information, information may be collected from the subject's credit card or insurance card, and/or the subject may be provided with an identification card with information that is readable by kiosk 1915. User information may, for example, include name, address, telephone, insurance information, physician information, etc. System 1900 may associate the subject's identifying information with identifying information from droplet actuator 1724. A user-generated code or a kiosk-generated code may be provided during the transaction. In this way, the purchased droplet actuator 1724 may be associated with subject. This association may be stored locally within kiosk 1915 or, alternatively, the information is transferred to a networked computer via the networked system.

Step 2: The subject or a medical care provider may load a sample on droplet actuator 1724. For example, a urine sample, blood sample, saliva sample, or stool sample may be loaded into a reservoir of droplet actuator 1724. Non-medical samples may also be used, e.g., a drinking water sample, aquarium water sample, a swimming pool water sample, a pond water sample, a plant sample, and the like. Kiosk 1915 may dispense instructions and or sample collection devices for collecting and handling the sample. Droplet actuator 1724 may be sealed to prevent leakage of the sample. Droplet actuator 1724 may be placed in a sealed container to prevent leakage of the sample.

Step 3: The subject may return the droplet actuator 1724 that has a sample therein to the site of kiosk 1915. Droplet actuator 1724 may be inserted into kiosk 1915 via any kind of receiving mechanism, such as a secure slot. Droplet actuator 1724 may be stored in a secure manner within kiosk 1915 until such time that it may be removed by an attendant. Droplet actuator 1724 may be stored in a temperature controlled environment within kiosk 1915. Alternatively, droplet actuator 1724 may be provided to an attendant at the site of the kiosk, at a physician's office or elsewhere. In another embodiment, a mailing label, package, and/or instructions may be dispensed with droplet actuator 1724, and droplet actuator may be mailed to a laboratory for processing.

Step 4: Droplet actuator 1724 is removed from kiosk 1915 by an attendant.

Step 5: Data storage device 1714 of droplet actuator 1724 may be scanned or otherwise read in order to extract the unique identification number and subject information. Alternatively, data storage device 1714 may include only a unique serial number, and the patient information may be stored at the local kiosk 1915 or at a centralized computer electronically coupled to the kiosk. The subject information may thus be matched to the serial number of the droplet actuator 1724. In this way, the droplet actuator 1724 is automatically associated with the certain subject that has provided the sample.

Step 6: Sample within droplet actuator 1724 may be analyzed and the results automatically reported via, for example, telephone, email, and/or the subject accessing the results via kiosk 1915 (e.g., using a code). For example, results may be reported to the subject or the subject's medical care provider.

A similar process may be used in a hospital environment. For example, a subject identifier and droplet actuator identifier may be associated at a subject's bedside or via a hospital supply system. Associated information may be centrally stored and/or stored on storage and/or transmission element 1714 of droplet actuator 1724.

A similar approach may be used for environmental studies, such as testing for contaminants in drinking water. Sample collection devices with unique serial numbers may be mailed to participants in the study. The serial numbers may, for example, be stored in an electronic format, such as an RFID actuator or in a physical format, such as a bar code. Users may load samples into the sample collection devices, and drop off the samples at local collection points (or ship them to a collection point) for analysis. The identifying information may be associated with the user's address. In this manner, certain geographical distributions of drinking water contamination may be identified. In a related embodiment, the users may take the sample collection devices to a kiosk analyzer, which controls droplet operations on the sample collection device and provides an output directly to the user. For example, a user may purchase a drinking water analysis collection device at a store, take it home and load it with a drinking water sample, bring it to a kiosk where it can be plugged in, permit the kiosk to run tests on the drinking water using a droplet actuator device that is part of the sample collection device, and provide the user with an output indicative of certain drinking water contaminants.

In yet another embodiment, kiosk 1915 may be reader instrument, and the user may insert droplet actuator 1724 into a reader slot, and kiosk 1915 may execute an assay using the droplet actuator. For example, a user may bring a water sample from home, obtain a droplet actuator from kiosk 1915, load a droplet of water onto the droplet actuator, electronically couple the droplet actuator to kiosk, whereupon kiosk 1915 executes and assay and provides the user with results. As another example, a sample collection container may be mailed to a user, the user may collect the sample, such as a water sample, take the sample to kiosk 1915, obtain a droplet actuator from kiosk 1915, load a droplet of water onto the droplet actuator, couple the droplet actuator to kiosk, whereupon kiosk 1915 executes and assay and provides the user with results. Results may also be centrally stored for further analysis. In some cases, kiosk 1915 may be set up to receive biohazardous materials.

Figure 20:
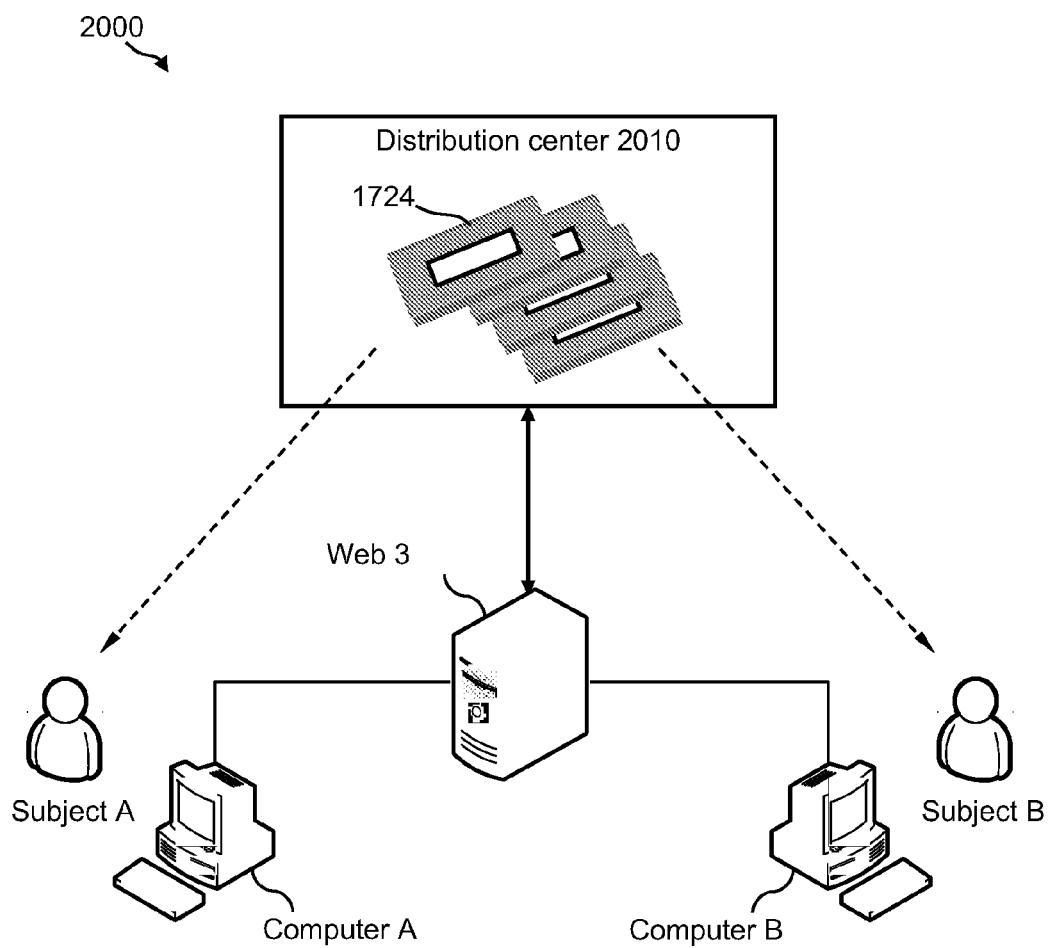
FIG. 20 is a functional diagram of another sample collection and analysis system of the invention.

FIG. 20 is a functional diagram of a sample collection system 2000 of the invention. System 2000 utilizes droplet actuators 1724 with data storage components 1714 (see FIG. 17). Sample collection system 2000 includes distribution center 2010, which may be, for example, a manufacturer facility or a warehouse distribution facility. Distribution center 2010 maintains an inventory of droplet actuators 1724.

A server is provided by which one or more subjects or medical providers may place orders for droplet actuators 1724 via, for example, a computer in a subject's home, a medical care provider's office, pharmacy, clinic, and so on. Using any standard web browser or network interface application, the server facilitates the order placement and payment operations. For each transaction by which droplet actuator 1724 is ordered, an association may be made between droplet actuator identifying information and an ordering party's or subject's identifying information. This association may be provided via credit card information, purchase order number, other subject information such as name, address, email, and telephone, and/or a subject-generated or system-generated code. In this manner, droplet actuator 1724 may be associated with a certain subject. This association may be stored on web server or other networked computer and associated with assay results.

As will be appreciated by one of skill in the art, aspects of the invention may be embodied as a method, system, or computer program product. Accordingly, various aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the invention may be written in an object oriented programming language such as Python, Java, Smalltalk, C++ or the like. However, the computer program code for carrying out operations of the invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Certain aspects of invention are described with reference to various methods and method steps. It will be understood that each method step can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the methods.

The computer program instructions may also be stored in a computer-readable memory that can direct a computer or other programmable data processing apparatus to function in a particular manner, such that the instructions stored in the computer-readable memory produce an article of manufacture including instruction means which implement various aspects of the method steps.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing various functions/acts specified in the methods of the invention.

CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of loading a droplet actuator, the method comprising:
   (a) providing a droplet actuator loading circuit comprising a primary fluid circuit arranged to flow fluid through a fluid path comprising a droplet operations gap of a droplet actuator and an external fluid circuit;
   (b) filling the loading circuit, including the droplet operations gap, with a liquid filler fluid and thereby purging the loading circuit of air, whereby all liquid lines of the primary fluid circuit and the external fluid circuit are filled with the liquid filler fluid and are substantially free of air bubbles;
   (c) flowing a reagent liquid into the external fluid circuit to form droplets in the liquid filler fluid contained therein using valves configured in the primary fluid circuit and/or the reagent fluid path to switch between:
      (i) circulating liquid in the primary fluid circuit; and
      (ii) flowing liquid from the one or more reservoirs comprising reagents and/or filler fluid into the primary fluid circuit; and
   (d) flowing contents of the external fluid circuit into the droplet operations gap of the droplet actuator.

2. The method of claim 1 wherein filling the loading circuit, including the droplet operations gap, with a liquid filler fluid comprises flowing filler fluid into the primary fluid circuit via a filler fluid branch in the primary fluid circuit.

3. The method of claim 2 wherein the filler fluid branch in the primary fluid circuit is situated in the external fluid circuit.

4. The method of claim 1 wherein flowing reagent liquid into the external fluid circuit comprises flowing reagent into the primary fluid circuit via a reagent branch in the primary fluid circuit.

5. The method of claim 4 wherein the reagent branch in the primary fluid circuit is situated in the external fluid circuit.

6. The method of claim 4 further comprising loading different reagent droplets into the external fluid circuit.

7. The method of claim 6 wherein the different reagent droplets are selected by switching the reagent branch from one reservoir to another reservoir.

8. The method of claim 7 wherein the switching is effected by a robotic device configured to move a terminus of the reagent fluid path from one reservoir to another reservoir.

9. The method of claim 1 wherein the flowing of steps (c) and (d) is conducted using a single reversible pump.

10. A method of loading a droplet actuator, the method comprising:
(a) providing a droplet actuator loading circuit comprising a primary fluid circuit arranged to flow fluid through a fluid path comprising a droplet operations gap of a droplet actuator and an external fluid circuit;
(b) filling the loading circuit, including the droplet operations gap, with a liquid filler fluid and thereby purging the loading circuit of air, whereby all liquid lines of the primary fluid circuit and the external fluid circuit are filled with the liquid filler fluid and are substantially free of air bubbles;
(c) flowing a reagent liquid into the external fluid circuit to form droplets in the liquid filler fluid contained therein;
(d) flowing contents of the external fluid circuit into the droplet operations gap of the droplet actuator; and
(e) flowing liquid from the droplet operations gap through an overflow fluid path fluidly coupled into the droplet operations gap.

11. The method of claim 10 wherein flowing liquid from the droplet operations gap through an overflow fluid path comprises pumping the liquid through the overflow path into a reservoir.

12. The method of claim 11 wherein the reservoir and pump together comprise a syringe pump.

13. The method of claim 1 wherein step (b) further comprises filling all channels of the droplet actuator with the liquid filler fluid, whereby all channels of the droplet actuator are substantially free of air bubbles.

14. The method of claim 10 wherein filling the loading circuit, including the droplet operations gap, with a liquid filler fluid comprises flowing filler fluid into the primary fluid circuit via a filler fluid branch in the primary fluid circuit.

15. The method of claim 14 wherein the filler fluid branch in the primary fluid circuit is situated in the external fluid circuit.

16. The method of claim 10 wherein flowing reagent liquid into the external fluid circuit comprises flowing reagent into the primary fluid circuit via a reagent branch in the primary fluid circuit.

17. The method of claim 16 wherein the reagent branch in the primary fluid circuit is situated in the external fluid circuit.

18. The method of claim 16 further comprising loading different reagent droplets into the external fluid circuit.

19. The method of claim 18 wherein the different reagent droplets are selected by switching the reagent branch from one reservoir to another reservoir.

20. The method of claim 19 wherein the switching is effected by a robotic device configured to move a terminus of the reagent fluid path from one reservoir to another reservoir.

21. The method of claim 10 wherein the flowing of steps (c) and (d) is conducted using a single reversible pump.

22. The method of claim 10 wherein step (b) further comprises filling all channels of the droplet actuator with the liquid filler fluid, whereby all channels of the droplet actuator are substantially free of air bubbles.

* * * * *